(12) United States Patent
Dykhuizen et al.

(10) Patent No.: US 11,980,613 B2
(45) Date of Patent: May 14, 2024

(54) METHODS FOR REVERSING HIV LATENCY USING BAF COMPLEX MODULATING COMPOUNDS

(71) Applicant: The Board of Trustees of the Leland Stanford Junior University, Stanford, CA (US)

(72) Inventors: Emily C. Dykhuizen, West Lafayette, IN (US); Gerald R. Crabtree, Woodside, CA (US); Tokameh Mahmoudi, Rotterdam (NL)

(73) Assignees: The Board of Trustees of the Leland Stanford Junior University, Stanford, CA (US); Purdue Research Foundation, West Lafayette, IN (US); Erasmus University Medical Center Rotterdam, Rotterdam (NL)

( * ) Notice: Subject to any disclaimer, the term of this patent is extended or adjusted under 35 U.S.C. 154(b) by 590 days.

(21) Appl. No.: 17/259,107

(22) PCT Filed: Jul. 11, 2019

(86) PCT No.: PCT/US2019/041466
§ 371 (c)(1),
(2) Date: Jan. 8, 2021

(87) PCT Pub. No.: WO2020/014524
PCT Pub. Date: Jan. 16, 2020

(65) Prior Publication Data
US 2021/0315876 A1 Oct. 14, 2021

Related U.S. Application Data

(60) Provisional application No. 62/697,002, filed on Jul. 12, 2018.

(51) Int. Cl.
*A61K 31/4427* (2006.01)
*A61K 31/395* (2006.01)
*A61P 31/18* (2006.01)

(52) U.S. Cl.
CPC ........ *A61K 31/4427* (2013.01); *A61K 31/395* (2013.01); *A61P 31/18* (2018.01)

(58) Field of Classification Search
CPC .... A61K 31/4427; A61K 31/395; A61P 31/18
USPC ....................................................... 514/338
See application file for complete search history.

(56) References Cited

U.S. PATENT DOCUMENTS

| | | | |
|---|---|---|---|
| 6,846,802 | B2 | 1/2005 | Chen et al. |
| 9,410,943 | B2 | 8/2016 | Kadoch et al. |
| 9,663,535 | B2 | 5/2017 | Breslin et al. |
| 2012/0202821 | A1 | 8/2012 | Obrecht et al. |
| 2015/0246907 | A1 | 9/2015 | Altmann et al. |
| 2017/0232065 | A1* | 8/2017 | Santa Maria ........ A61K 9/0019 514/9.4 |
| 2021/0138036 | A1* | 5/2021 | Santa Maria ........ C07K 14/485 |
| 2021/0315876 | A1 | 10/2021 | Dykhuizen et al. |

FOREIGN PATENT DOCUMENTS

| WO | WO200177113 A2 | 10/2001 |
|---|---|---|
| WO | WO2019055657 A1 | 3/2019 |

OTHER PUBLICATIONS

National Center for Biotechnology Information. PubChem Substance Record for SID 131428141, BRD-K69367836-001-01-4, Source: Broad Institute. https://pubchem.ncbi.nlm.nih.gov/substance/131428141. Date Available: Dec. 20, 2011.
National Center for Biotechnology Information. PubChem Substance Record for SID 172131385, BRD-K51299478-001-01-2, Source: Broad Institute. https://pubchem.ncbi.nlm.nih.gov/substance/172131385. Date Available: Feb. 7, 2015.
National Center for Biotechnology Information. PubChem Substance Record for SID 131429945, BRD-K98645985-001-01-7, Source: Broad Institute. https://pubchem.ncbi.nlm.nih.gov/substance/131429945. Date Available: Dec. 20, 2011.
Arasappan et al., Novel Dipeptide Macrocycles from 4-Oxo, -Thio, and -Amino-Substituted Proline Derivatives, J. Org. Chem., 2002, 67, 11, 3923-3926.
Fitzgerald et al., A Build/Couple/Pair Strategy for the Synthesis of Stereochemically Diverse Macrolactams via Head-to-Tail Cyclization, ACS Comb Sci, Feb. 13, 2012; 14(2): 89-96.
Fitzgerald et al., A Build/Couple/Pair Strategy for the Synthesis of Stereochemically Diverse Macrolactams via Head-to-Tail Cyclization, Supporting Information, ACS Comb Sci, Feb. 13, 2012; 58 pages.
Marsault et al., Potent Macrocyclic Antagonists to the Motilin Receptor Presenting Novel Unnatural Amino Acids, Bioorg Med Chem Lett, Aug. 1, 2007; 17(15):4187-90.

(Continued)

*Primary Examiner* — Kristin A Vajda
(74) *Attorney, Agent, or Firm* — Bret E. Field; Bozicevic, Field & Francis LLP

(57) ABSTRACT

This disclosure provides methods of using BAF complex modulating compounds as inhibitors of BAF-mediated transcription in target cells. The BAF complex modulating compounds include 12-membered macrolactam compounds that can target a BAF-specific subunit (e.g., ARID1A) to prevent nucleosomal positioning, relieving transcriptional repression of HIV-1. The subject methods can provide for reversal of latency of HIV-1 in cells in vitro or in vivo. Use of the macrolactam BAF complex modulating compounds represent a method of HIV latency reversal with a unique mechanism of action, which can be optionally combined with other Latency Reversal Agents to improve reservoir targeting. The subject methods can be utilized in conjunction with any convenient methods of treating HIV or HIV latency, including methods related to immune system activation, antiretroviral therapies and/or anti-HIV agents.

20 Claims, 28 Drawing Sheets
Specification includes a Sequence Listing.

(56) References Cited

OTHER PUBLICATIONS

Over et al., Structural and conformational determinants of macrocycle cell permeability, Nature Chemical Biology 12, 1065-1074 (2016).
Shirakawa et al., Reactivation of latent HIV by histone deacetylase inhibitors, Trends Microbiol, Jun. 2013; 21(6): 277-285.
Son et al., The role of BAF (mSWI/SNF) complexes in mammalian neural development, Am J Med Genet C Semin Med Genet, Sep. 2014; 0(3):333-349.
Hill et al., Predicting the outcomes of treatment to eradicate the latent reservoir for HIV-1, PNAS Sep. 16, 2014; 111(37):13475-13480.
Hohmann et al., A rationale to target the SWI/SNF complex for cancer therapy, Trends Genet, Aug. 2014; 30(8):356-63.
Marian et al., Small Molecule Targeting of Specific BAF (mSWI/SNF) Complexes for HIV Latency Reversal, Cell Chem Biol, Dec. 20, 2018; 25(12):1443-1455.
Weber et al., ATM and ATR as therapeutic targets in cancer, Pharmacol Ther, May 2015; 149:124-38.

* cited by examiner

| | Luciferase IC₅₀ (μM) | qRT-PCR Bmi1/Ring1/Fgf4 | | Luciferase IC₅₀ (μM) | qRT-PCR Bmi1/Ring1/Fgf4 |
|---|---|---|---|---|---|
| BRD-K98645985 - (2-pyridyl-phenyl) | 4.5 ± 1 | 6.5 ± 2.0 / 1.7 ± 0.5 / 0.35 ± 0.3 | BRD-K13648511 - (benzyl) | NA | NA |
| BRD-K17257309 - (3-pyridyl-phenyl) | 37 ± 12 | 2.2 ± 0.2 / 1.7 ± 0.5 / 0.46 ± 0.3 | BRD-K26156119 - (2-F-benzyl) | NA | NA |
| BRD-K13449002 - (4-pyridyl-phenyl) | 12.6 ± 2.3 | 4.0 ± 0.7 / 1.6 ± 0.3 / 0.17 ± 0.1 | BRD-K71642560 - (3-F-benzyl) | NA | NA |
| BRD-K7307054 - (pyrimidyl-phenyl) | NA | NA | BRD-K79609051 - (4-F-benzyl) | NA | NA |
| BRD-K92576614 - (2-pyridyl-methyl) | NA | NA | BRD-K02599060 - (benzoyl) | NA | NA |
| BRD-K60351210 - (3-pyridyl-methyl) | NA | NA | BRD-K90159582 - (2-pyridyl-phenyl-carbonyl) | NA | NA |
| BRD-K77628901 - (4-pyridyl-methyl) | NA | NA | BRD-K79740310 - (2-pyridyl-phenyl-NHC(O)) | NA | NA |
| BRD-K81318113 - (pyrimidyl-methyl) | NA | NA | BRD-K15849455 - (H) | NA | NA |

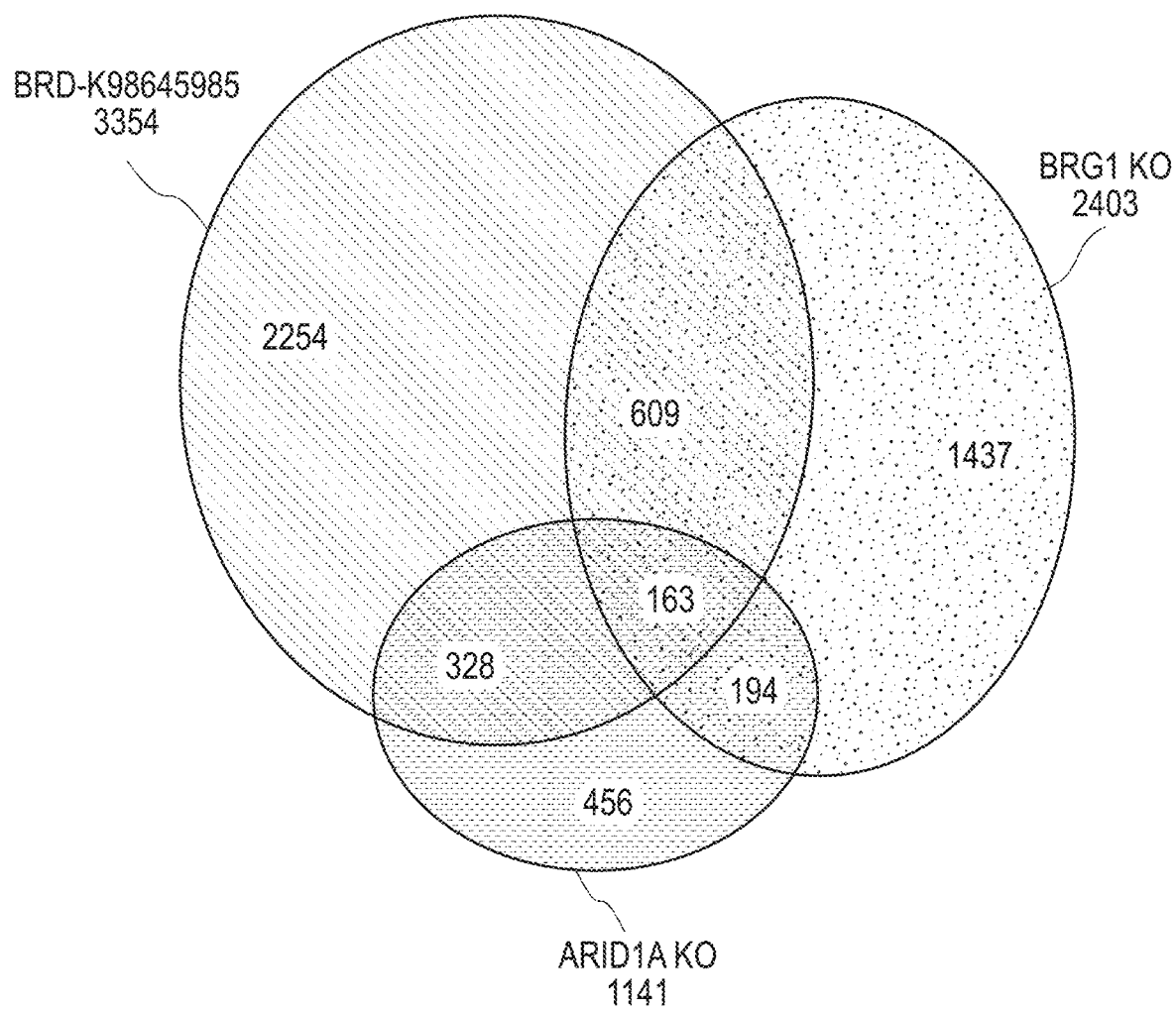

CAM2-56

CAM2-64

BRD-K83694683

METHODS FOR REVERSING HIV LATENCY USING BAF COMPLEX MODULATING COMPOUNDS

CROSS-REFERENCE TO RELATED APPLICATION

This application is a U.S. National Stage Application of PCT Application No. PCT/US2019/041466 filed Jul. 11, 2019, which application, pursuant to 35 U.S.C. § 119(e), claims priority to the filing date of U.S. Provisional Patent Application Ser. No. 62/697,002 filed Jul. 12, 2018; the disclosure of which applications are herein incorporated by reference.

REFERENCE TO AN ELECTRONIC SEQUENCE LISTING

The contents of the electronic sequence listing (STAN-1490_SEQ_LIST.txt; Size: 5,096 bytes; and Date of Creation: Mar. 12, 2024) is herein incorporated by reference in its entirety.

FIELD OF THE INVENTION

The present disclosure relates to methods of using BAF complex modulating compounds comprising for reversing HIV latency in a cell. The subject methods can be used in conjunction with any convenient methods of treating HIV.

INTRODUCTION

Since the discovery of HIV-1 as the causative agent of AIDS, enormous progress has been made in treating HIV-1 infections and prolonging the lifespan of HIV-1 infected individuals. State of the art treatment is a cocktail of drugs acting on different viral targets, known as combination Anti-Retroviral Therapy (c-ART). c-ART is extremely effective at suppressing HIV-1 to undetectable levels, preventing progression to AIDS; however, treatment must be maintained for life and as of yet, HIV-1 eradication is not achievable. Despite being highly efficient in stopping active viral replication, anti-retroviral drugs do not target latently infected cells that harbor replication competent but transcriptionally silent proviruses. Latently infected cells persist in the body for life and, not being targeted by either c-ART or immune cells, they constitute the viral reservoir. When these cells are activated, transcription from latent HIV-1 provirus is induced and in the absence of c-ART, viral replication rebounds.

The persistence of a pool of latently HIV-1-infected cells despite combination Anti-Retroviral Therapy (cART) treatment is the major roadblock for a cure. A number of genetic and epigenetic factors are involved in establishing and maintaining viral latency, and significant effort has been invested in chemically targeting these regulators with the aim to purge the latent reservoir; however, the use of currently available latency reversal agents (LRAs) has been hampered by their limited effectiveness or high toxicity, stressing the need for more specific and less toxic compounds.

SUMMARY

This disclosure provides methods of using BAF complex modulating compounds as inhibitors of BAF-mediated transcription in target cells. The BAF (mammalian SWI/SNF) chromatin remodeling 1 complex is involved in establishing and maintaining viral latency through nucleosome positioning, making it an attractive drug target for HIV-1 latency reversal. The BAF complex modulating compounds include 12-membered macrolactam compounds that can target a BAF-specific subunit (e.g., ARID1A) to prevent nucleosomal positioning, relieving transcriptional repression of HIV-1. The subject methods can provide for reversal of latency of HIV-1 in cells in vitro or in vivo. In some cases, the methods are performed in vitro, e.g., in an in vitro T cell line or in an ex vivo primary cell model of HIV-1 latency. In some cases, the subject methods can be performed without undesirable cell toxicity or T cell activation. Use of the macrolactam BAF complex modulating compounds represent a method of HIV latency reversal with a unique mechanism of action, which can be optionally combined with other Latency Reversal Agents to improve reservoir targeting.

The subject methods can be utilized in conjunction with any convenient methods of treating HIV or HIV latency, including methods related to immune system activation, antiretroviral therapies and/or anti-HIV agents.

7% MeOH in CH$_2$Cl$_2$, 13 min) to afford the product as a yellow solid in 24% yield (38 mg) over 2 steps. (M+H)$^+$ calculated=574.3388 (M+H)$^+$ average (3 ESI replicates)= 5.74.3394±0.85

Figure 10:
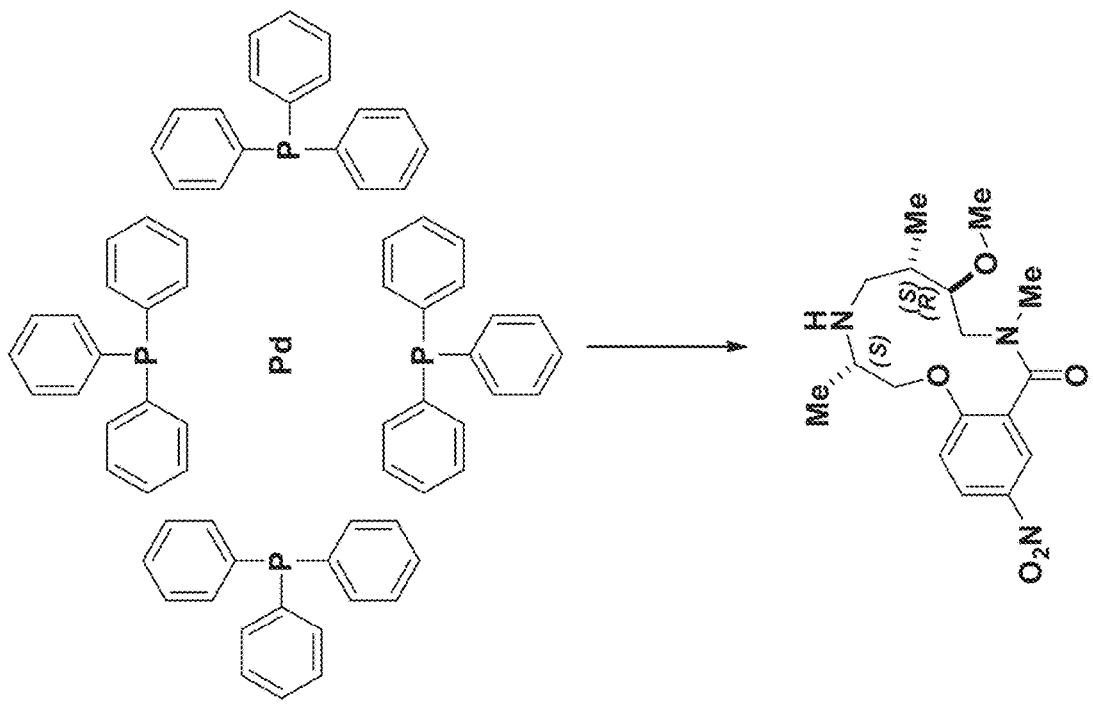
Figure 10:
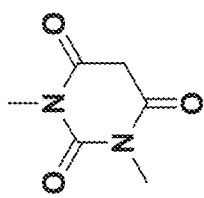
Figure 10:
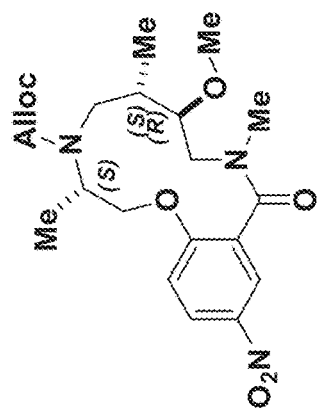

FIG. 10: BRD-K98645985: 4-(Pyridin-2-yl)benzaldehyde (199 mg, 1.085 mmol) was added to a DMF (Volume: 1808 µl) solution of crude amine (2141-022) (147 mg, 0.362 mmol) at room temperature. Acetic acid (21.72 mg, 0.362 mmol) was added and the mixture was stirred for 30 min before NaBH(OAc)$_3$ (307 mg, 1.446 mmol) was added and the mixture was stirred at rt overnight. LC/MS indicated conversion into the desired product. Saturated aqueous sodium bicarbonate solution was slowly added until gas evolution ceased. The reaction mixture was diluted with EtOAc and the layers were separated. The aqueous phase was extracted with EtOAc (3×). The combined organic layers were washed with brine, dried with MgSO$_4$, filtered, and concentrated. The residue was purified via ISCO (0.5-7% MeOH in CH$_2$Cl$_2$, 13 min); Collected fractions 66-73 to afford the product as a brown solid in 26% yield (54 mg) over 2 steps. (M+H)$^+$ calculated=574.3388 (M+H)$^+$ average (3 ESI replicates)=5.74.3395±1.36.

Figure 11:
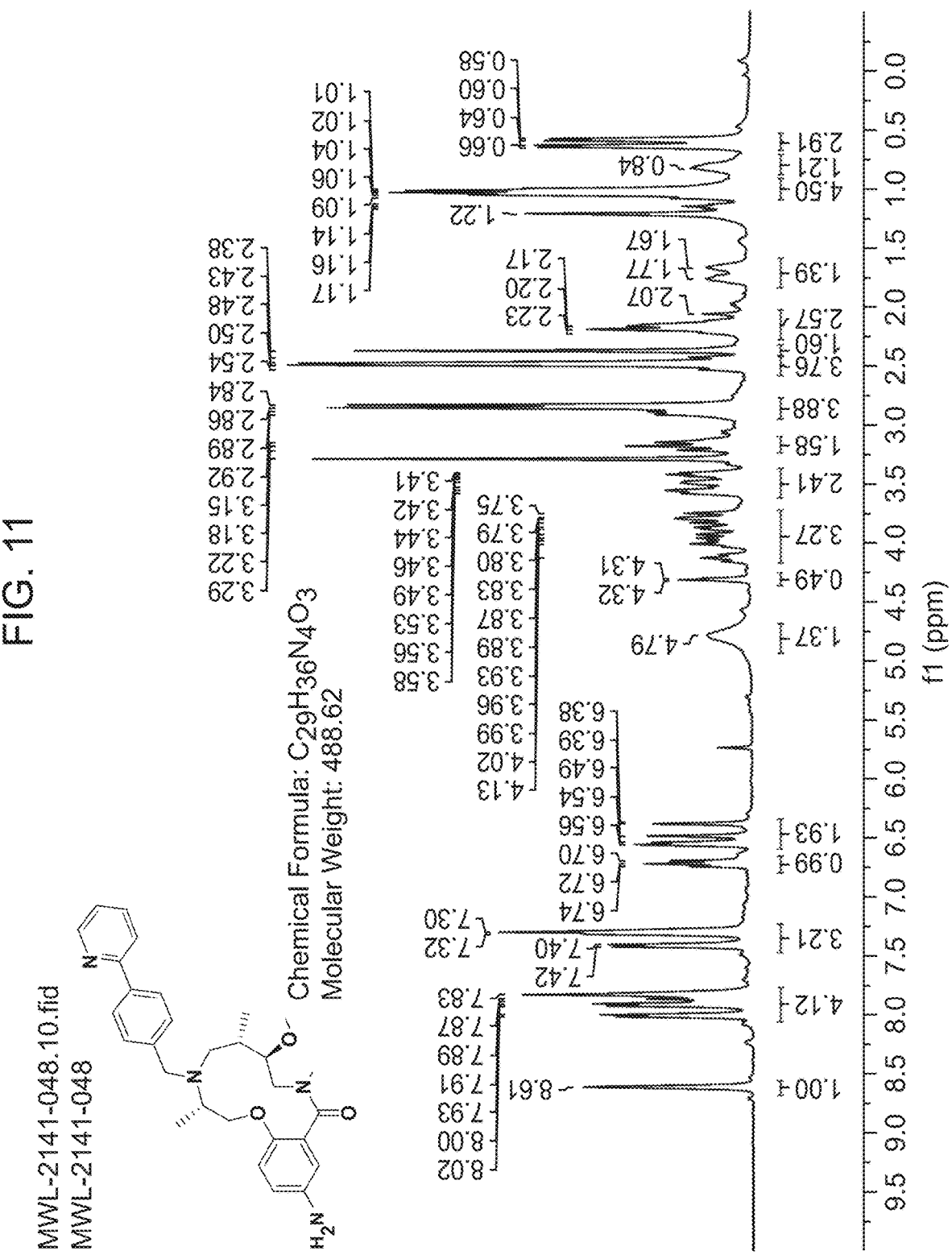
Figure 11:
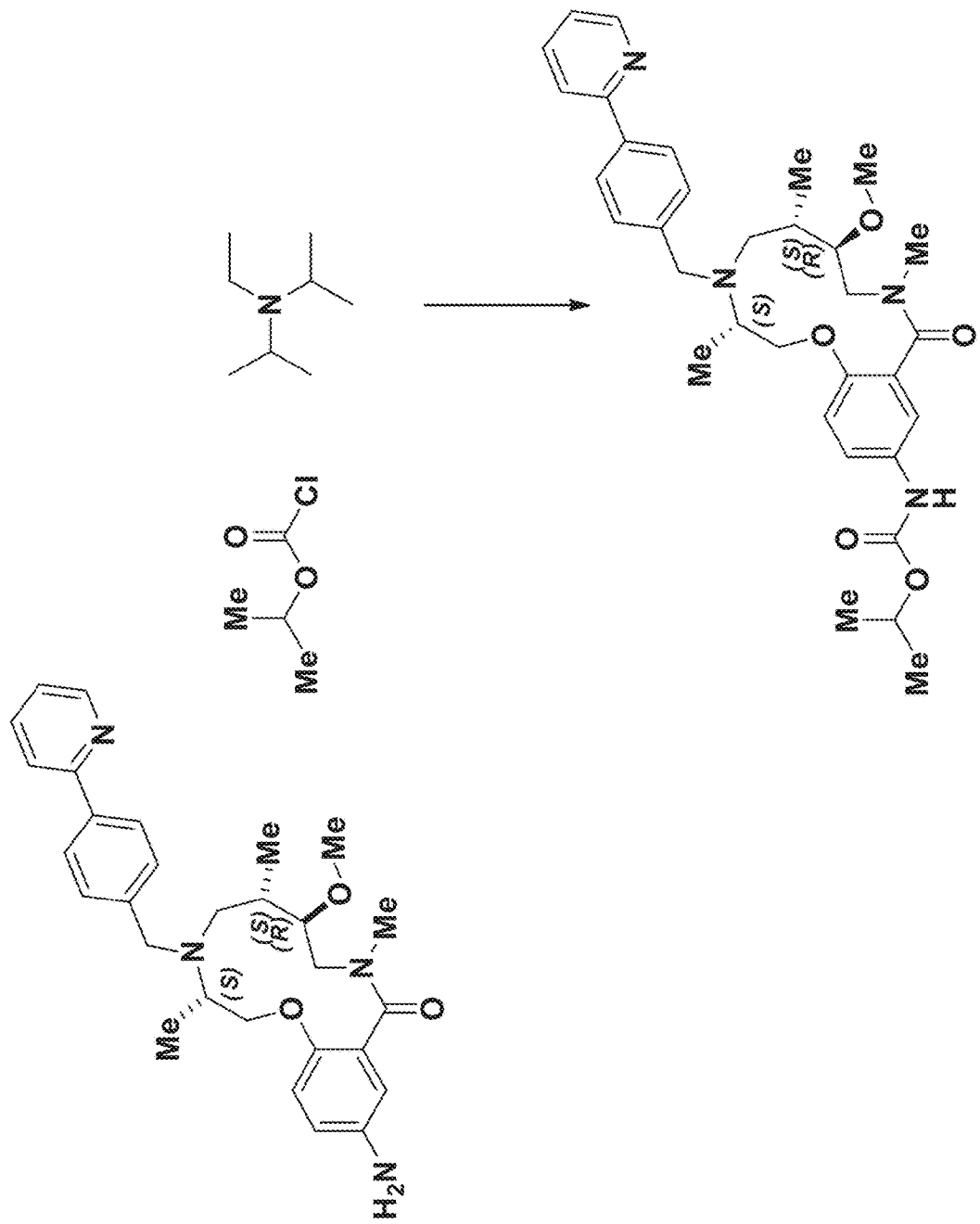

FIG. 11: BRD-K25923209: To Macrocycle 2141-039b (0.804 g, 1.550 mmol) dissolved in MeOH (Volume: 15.50 ml) was added tin(II) chloride dihydrate (3.50 g, 15.50 mmol). The reaction mixture was stirred at 40° C. for 24 h until LC/MS indicated complete consumption of starting material (nitro) and presence of desired mass. Upon completion, the reaction mixture was concentrated and the resulting residue was dissolved in EtOAc and washed with 2 M aq. KOH (2×). The combined aqueous layers were washed with EtOAc (4×). The resulting organic layers were washed with brine, saturated aqueous NaHCO$_3$, water, and brine, dried over MgSO$_4$, filtered, and concentrated. The crude aniline was sufficiently pure to use in the capping step and therefore was used without purification. Note: The workup as described above produces a lot of precipitate/emulsion. This can be overcome by extensive washing or alternately, the reaction can be quenched with 1 volume of 1 M NaOH, stirred with celite for 10 minutes, and filtered prior to workup to yield 33.8% (17.2 mg) over 3 steps. (M+H)$^+$ calculated=489.286 (M+H)$^+$ average (3 ESI replicates)= 489.2866±0.92.

Figure 12:
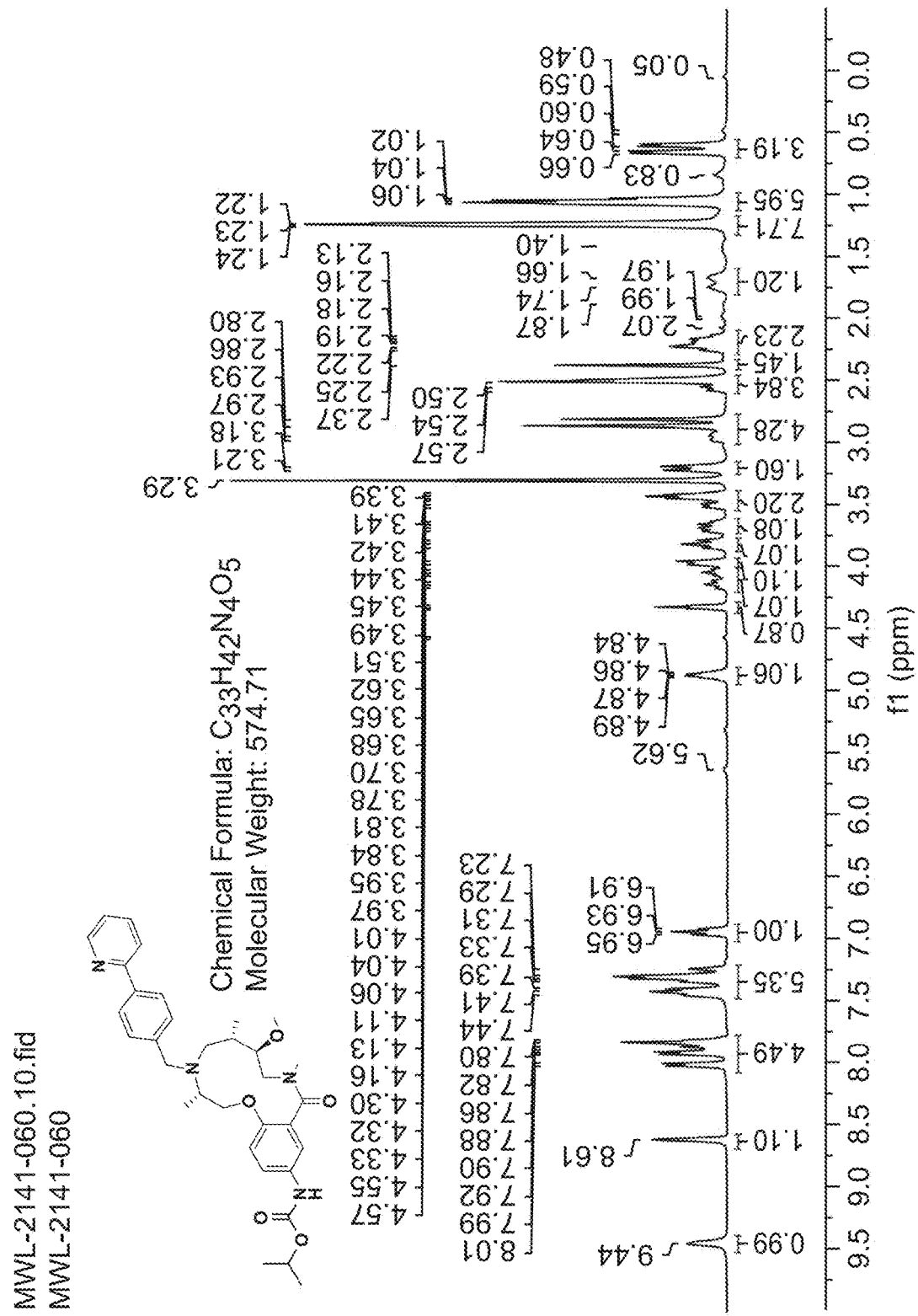
Figure 12:
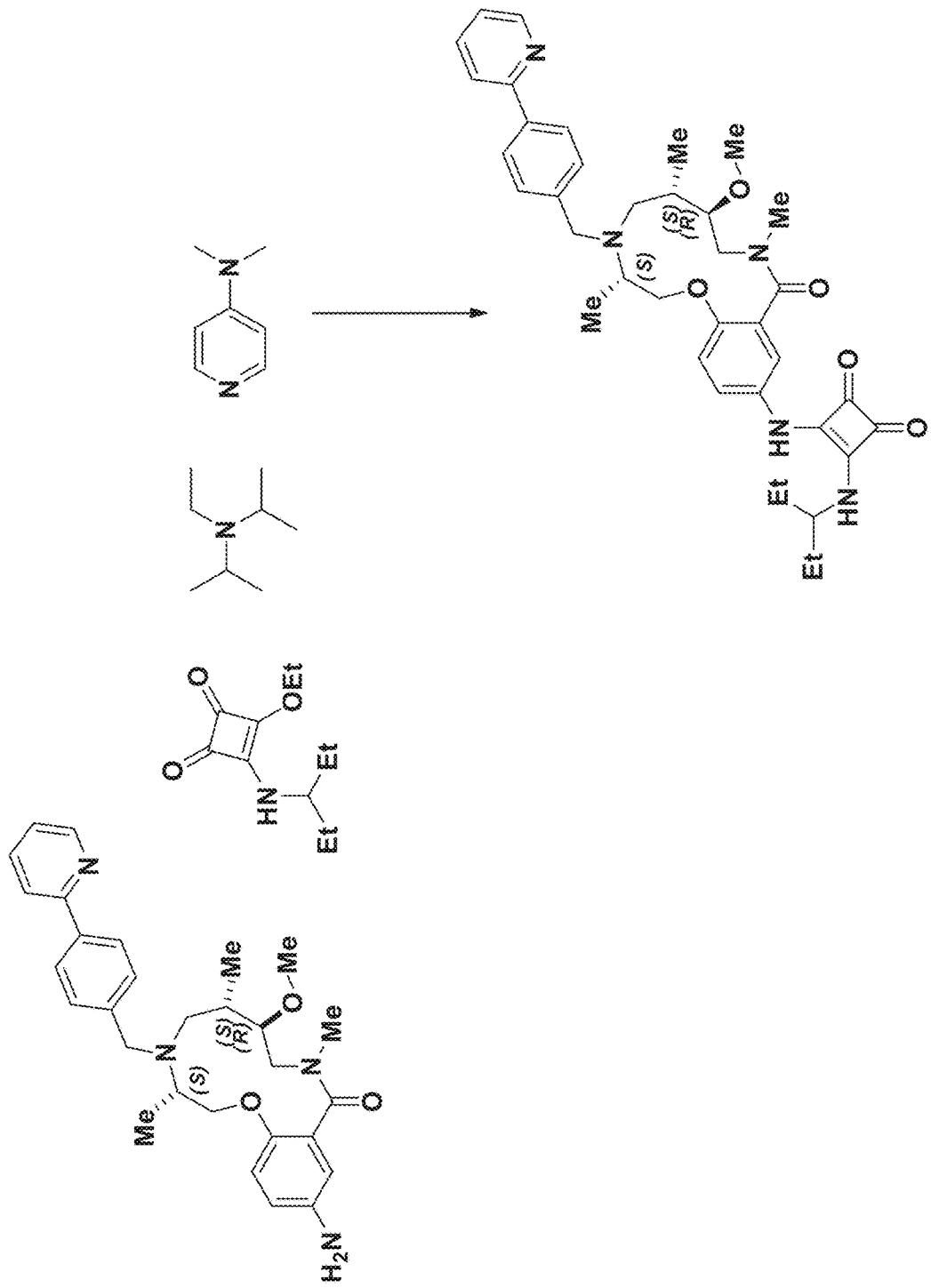

FIG. 12: BRD-K80443127: A screwtop vial was charged with aniline (BRD-K25923209) (43.3 mg, 0.089 mmol) and CH$_2$Cl$_2$ (Volume: 886 µl, Density: 1.325 g/ml). Isopropyl chloroformate (115 µl, 0.115 mmol) and DIEA (46.4 µl, 0.266 mmol) were added dropwise and reaction stirred under ambient conditions for 1 h. LC/MS showed complete sm consumption. The reaction mixture was loaded directly onto SiO$_2$ and purified via ISCO (1-12% MeOH in CH$_2$Cl$_2$, 20 min); Collected fractions 40-44 to afford the product as a yellow oil in 33.8% (17.2 mg) yield. (M+H)$^+$ calculated=575.3228 (M+H)$^+$ average (3 ESI replicates)= 575.3235±1.32.

Figure 13:
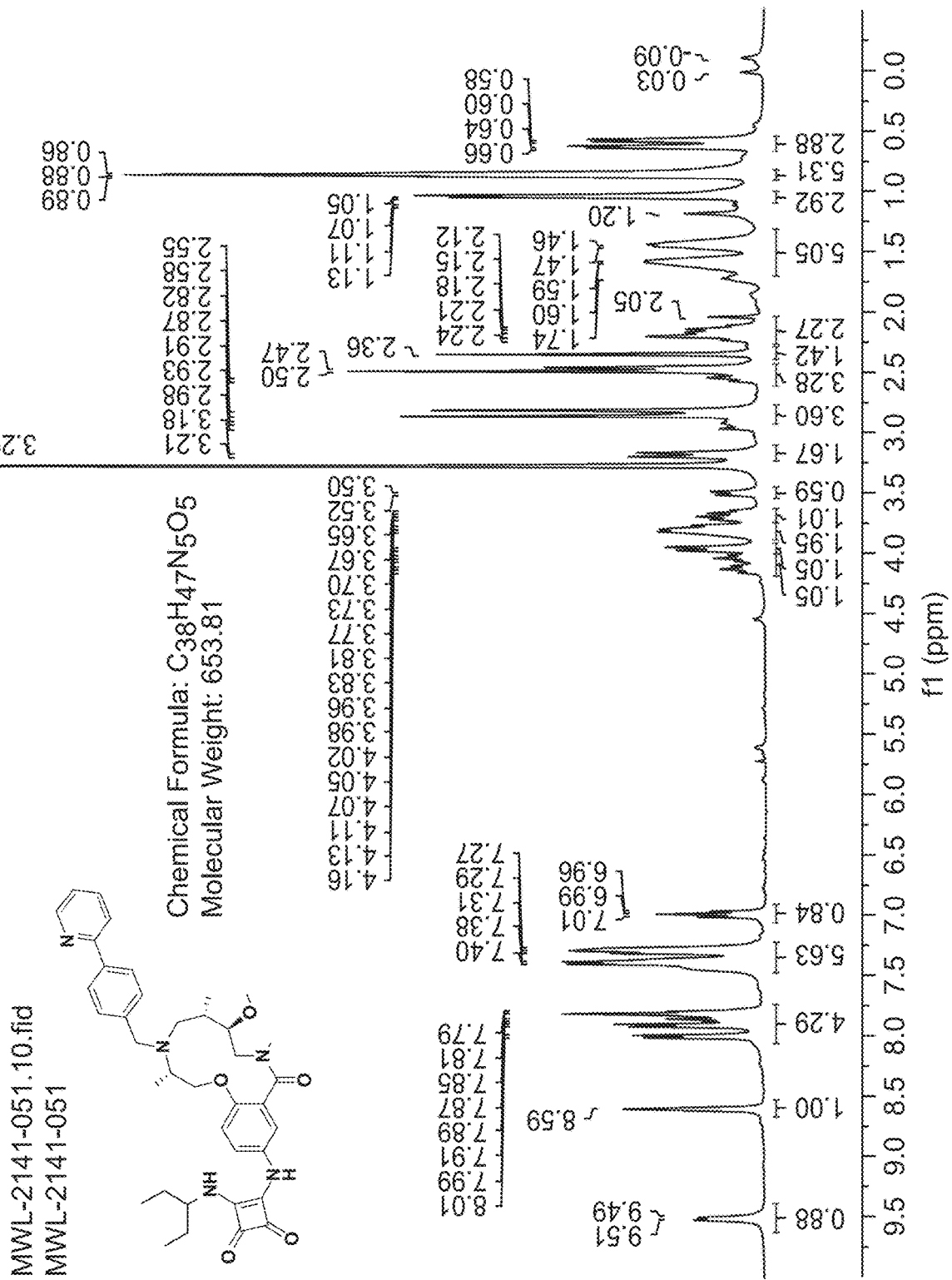

FIG. 13: BRD-K04244835: A 2.5 mL microwave vial was charged with aniline (BRD-K25923209) (40 mg, 0.082 mmol) and EtOH (Volume: 819 µl, Density: 0.81 g/ml). Squaramide (CRE-III-001) (20.75 mg, 0.098 mmol), DIEA (42.8 µl, 0.246 mmol), and DMAP (2.000 mg, 0.016 mmol) were added in sequence and the vial was sealed. The resulting solution was stirred at 85° C. overnight or until LC/MS indicated complete starting material consumption. The reaction mixture was loaded directly onto SiO$_2$ and purified via ISCO (1-12% MeOH in CH$_2$Cl$_2$, 20 min); fractions 50-56 were collected to afford the product as a yellow solid in 48.6% (26 mg) yield. (M+H)$^+$ calculated=654.365 (M+H)$^+$ average (3 ESI replicates)= 654.3661±1.64.

DETAILED DESCRIPTION

This disclosure provides methods of using BAF complex modulating compounds as inhibitors of BAF-mediated transcription in target cells. The BAF complex modulating compounds include 12-membered macrolactam compounds that can target a BAF-specific subunit (e.g., ARID1A) to prevent nucleosomal positioning, relieving transcriptional repression of HIV-1. The subject methods can provide for reversal of latency of HIV-1 in cells in vitro or in vivo. Use of the macrolactam BAF complex modulating compounds represent a method of HIV latency reversal with a unique mechanism of action, which can be optionally combined with other Latency Reversal Agents to improve reservoir targeting. The subject methods can be utilized in conjunction with any convenient methods of treating HIV or HIV latency, including methods related to immune system activation, antiretroviral therapies and/or anti-HIV agents.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

BAF Complex Modulating Compounds

As summarized above, aspects of the disclosure include methods of using BAF modulating compounds to reverse HIV latency in a cell. Exemplary BAF modulating compounds including 12-membered macrolactam core structures that find use in the subject methods are set forth in the following structures 1-10 and formulae I-III.

In some cases, the subject BAF modulating compound is of formula (I):

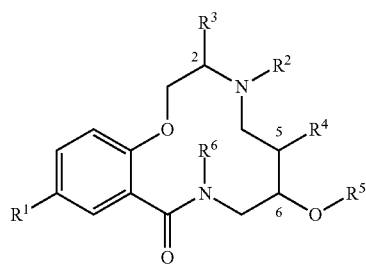

(I)

wherein:
R$^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;
R$^2$ is a heteroaryl-aryl-alkyl, substituted heteroaryl-aryl-alkyl, aryl-heteroaryl-alkyl, substituted aryl-heteroaryl alkyl, alkanoyl or substituted alkanoyl;
R$^3$ to R$^6$ are each independently H, alkyl or substituted alkyl;
or a pharmaceutically acceptable salt thereof.

It will be understood that unless indicated otherwise, in any BAF modulating compound described herein having one or more chiral centers, if an absolute stereochemistry is not expressly indicated, then each center may independently be of R-configuration or S-configuration or a mixture thereof. In certain embodiments of formula (I), the stereochemistry at C2, C5 and C6 is configured to provide the S, S, R stereoisomer at C2, C5 and C6 respectively. In other embodiments, the stereochemistry of the compound of formula (I) is configured to provide the R, S, R stereoisomer at C2, C5 and C6 respectively.

In some cases, the subject BAF modulating compound is of the formula (IA):

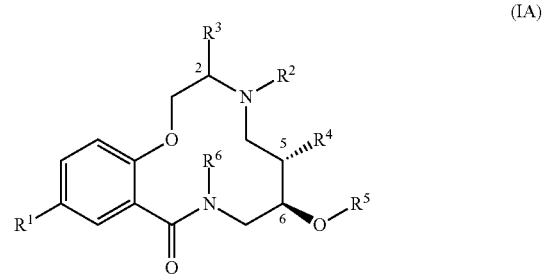

(IA)

wherein:
R$^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;
R$^2$ is a heteroaryl-aryl-alkyl, substituted heteroaryl-aryl-alkyl, aryl-heteroaryl-alkyl, substituted aryl-heteroaryl alkyl, alkanoyl or substituted alkanoyl;
R$^3$ to R$^6$ are each independently H, alkyl or substituted alkyl;
or a pharmaceutically acceptable salt thereof.

In certain embodiments the compound of formula (IA), the stereochemistry at C2 is configured to provide the S, S, R stereoisomer at C2, C5 and C6 respectively. In other embodiments, the stereochemistry of the compound of formula (IA) is configured to provide the R, S, R stereoisomer at C2, C5 and C6 respectively.

In some cases, the subject BAF modulating compound is of the formula (IB):

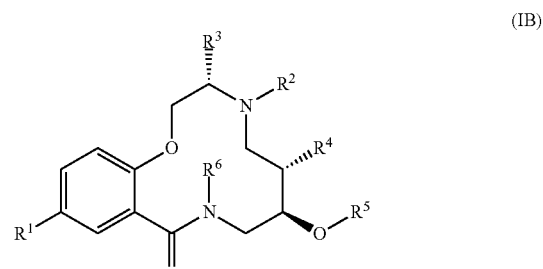

(IB)

wherein:
  R¹ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;
  R² is a heteroaryl-aryl-alkyl, substituted heteroaryl-arylalkyl, aryl-heteroaryl-alkyl, substituted aryl-heteroaryl alkyl, alkanoyl or substituted alkanoyl;
  R³ to R⁶ are each independently H, alkyl or substituted alkyl;
or a pharmaceutically acceptable salt thereof.

In some embodiments of any of formulae (I) to (IB), R¹ is an alkylaminocarbonylamino. Particular examples of alkylaminocarbonylamino groups include, but are not limited to isopropyl-NHCONH— and propyl-NHCONH. In other cases, R¹ is an arylaminocarbonylamino group. A particular example of an arylaminocarbonylamino group includes, but is not limited to phenyl-NHCONH—. In some cases, R¹ is an amine. Particular example of amines include, but are not limited to —NH₂ and pyrimidine-NH—. In some cases, R¹ is a carbamate. A particular example of a carbamate includes, but is not limited to isopropyl-OCONH—. In some cases, R¹ is an alkanoylamino. Particular examples of alkanoylamino groups include, but are not limited to isopropyl-CONH— and propyl-CONH—. In some other cases, R¹ is an aroylamino. A particular example of an aroylamino group includes, but is not limited to phenyl-CONH—. It will be understood that any of the R¹ groups disclosed herein may be optionally substituted, e.g., with a substituent as described herein.

In some embodiments of any of formulae (I) to (IB), R¹ is selected from:

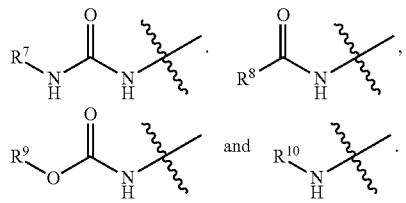

In some cases, R⁷, R⁸ and R⁹ are each independently selected from, alkyl, substituted alkyl, aryl, substituted aryl, heteroaryl, substituted heteroaryl, cycloalkyl, substituted cycloalkyl, heterocycle, substituted heterocycle; and R¹⁰ is substituted H, alkyl, substituted alkyl, aryl, substituted aryl, heteroaryl, substituted heteroaryl, cycloalkyl, substituted cycloalkyl, heterocycle and substituted heterocycle.

In certain cases, R⁷ is alkyl or substituted alkyl. In some cases R⁷ is methyl, ethyl, propyl, isopropyl, butyl, sec-butyl, tert-butyl, pentyl, hexyl. In some cases, R⁷ is an aryl or a substituted aryl group. In some cases R⁷ is phenyl or substituted phenyl. In some cases R⁷ is heteroaryl or substituted heteroaryl. In some cases, R⁷ is cycloalkyl or substituted cycloalkyl. In certain cases, R⁷ is a heterocycle or substituted heterocycle.
In certain cases, R⁸ is alkyl or substituted alkyl. In some cases R⁸ is methyl, ethyl, propyl, isopropyl, butyl, sec-butyl, tert-butyl, pentyl, hexyl. In some cases, R⁸ is an aryl or a substituted aryl group. In some cases R⁸ is phenyl or substituted phenyl. In some cases R⁸ is heteroaryl or substituted heteroaryl. In some cases, R⁸ is cycloalkyl or substituted cycloalkyl. In certain cases, R⁸ is a heterocycle or substituted heterocycle.

In certain cases, R⁹ is alkyl or substituted alkyl. In some cases R⁹ is methyl, ethyl, propyl, isopropyl, butyl, sec-butyl, tert-butyl, pentyl, hexyl. In some cases, R⁹ is an aryl or a substituted aryl group. In some cases R⁹ is phenyl or substituted phenyl. In some cases R⁹ is heteroaryl or substituted heteroaryl. In some cases, R⁹ is cycloalkyl or substituted cycloalkyl. In certain cases, R⁹ is a heterocycle or substituted heterocycle.

In some cases, R¹⁰ is H. In certain cases, R¹⁰ is alkyl or substituted alkyl. In some cases R¹⁰ is methyl, ethyl, propyl, isopropyl, butyl, sec-butyl, tert-butyl, pentyl, hexyl. In some cases, R¹⁰ is an aryl or a substituted aryl group. In some cases R¹⁰ is phenyl or substituted phenyl. In some cases R¹⁰ is heteroaryl or substituted heteroaryl. In some cases, R¹⁰ is cycloalkyl or substituted cycloalkyl. In certain cases, R¹⁰ is a heterocycle or substituted heterocycle. In some cases R¹⁰ is a nitrogen containing heteroaryl, e.g., pyridine, pyrimidine, pyridazine, pyrazine, triazine. In certain cases, R¹⁰ is pyrimidine.

In some embodiments of any of formulae (I) to (IB) R¹ is selected from.

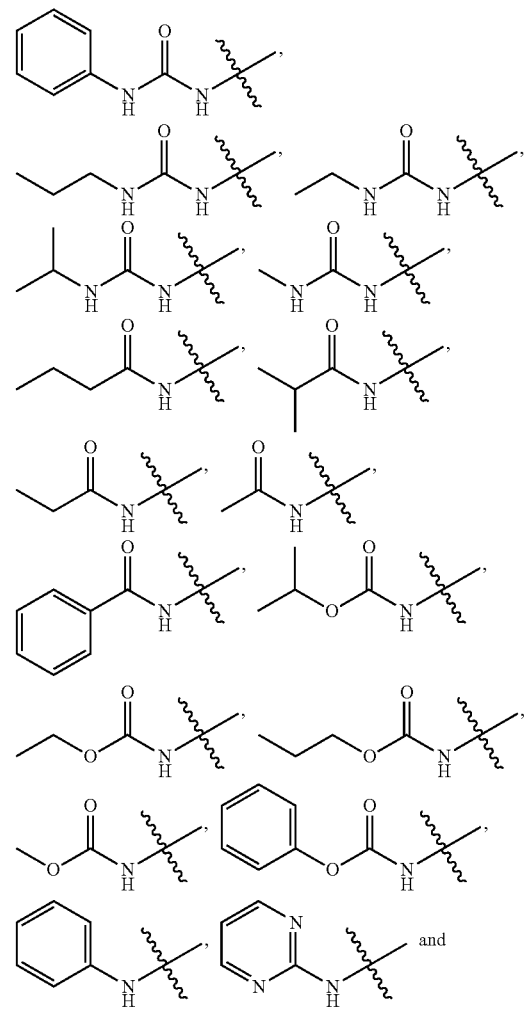

-continued

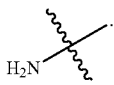

In certain cases of any of formulae (I) to (IB), $R^1$ is selected from:

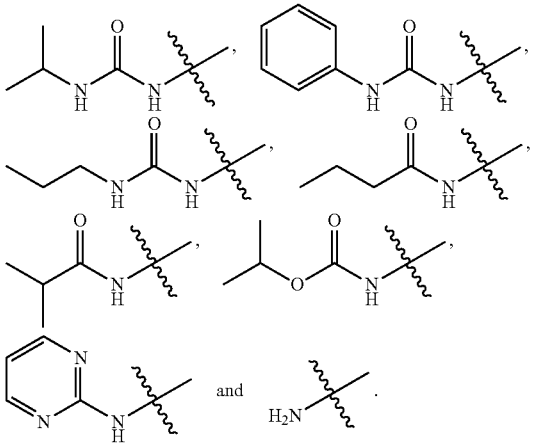

In some embodiments of any of formulae (I) to (IB), $R^2$ is heteroaryl-aryl-alkyl. Particular examples of heteroaryl-aryl-alkyl include, but are not limited to, 4-(pyridin-2-yl)-benzyl, 4-(pyridin-3-yl)-benzyl and 4-(pyridine-4-yl)-benzyl. In some cases, $R^2$ is aryl-heteroaryl-alkyl. In some cases, $R^2$ is alkanoyl. A particular example of an alkanoyl includes, but is not limited to cyclopropyl-acetyl. In will be understood that any of the $R^2$ groups disclosed herein may be optionally substituted, e.g., with a substituent as described herein.

In some embodiments of any of formulae (I) to (IB), $R^2$ is of the formula:

-L$^1$-Z(IC); or

-L$^2$-C(O)-L$^3$-R$^{11}$(ID)

wherein, $L^1$ is an alkyl linker or a substituted alkyl linker; $L^2$ and $L^3$ are each independently selected from a covalent bond, an alkyl linker and a substituted alkyl linker; Z is heteroaryl-aryl, substituted heteroaryl-aryl, aryl-heteroaryl or substituted heteroaryl-aryl; and $R^{11}$ is alkyl, substituted alkyl, $C_{3-10}$ cycloalkyl, substituted $C_{3-10}$ cycloalkyl, $C_{3-10}$ heterocycle or substituted $C_{3-10}$ heterocycle.

In some cases, any of $L^1$, $L^2$ or $L^3$ is a $(C_1$-$C_{12})$alkyl linker, which may be straight or branched, e.g., methyl, ethyl, n-propyl, 1-methylethyl (iso-propyl), n-butyl, n-pentyl, 1,1-dimethylethyl (t-butyl), and the like. In some cases $L^1$ is methyl. In some cases $L^2$ is a covalent bond. In some cases $L^3$ is methyl.

In some embodiments, the $R^2$ group of formula (IC), has the formula (IE):

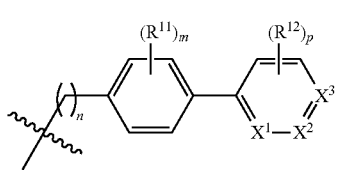

(IE)

wherein:

two of $X^1$, $X^2$ and $X^3$ are carbon atoms and one of $X^1$, $X^2$ and $X^3$ is a nitrogen atom;

$R^{11}$ and $R^{12}$ are independently selected from OH, alkyl, substituted alkyl, alkenyl, substituted alkenyl, aryl, substituted aryl, alkoxy, substituted alkoxy, —OCF$_3$, —CF$_3$, halogen, azide, amine, substituted amine, amide, cycloalkyl, substituted cycloalkyl, heterocycle and substituted heterocycle;

n is an integer from 1 to 12;

m is an integer from 0 to 4; and p is an integer from 0 to 5.

In some cases of formula (IE), $X^1$ is a nitrogen atom, $X^2$ and $X^3$ are carbon atoms, n is 1, m is 0 and p is 0. In other cases of formula (IE), $X^2$ is a nitrogen atom, $X^1$ and $X^3$ are carbon atoms, n is 1, m is 0 and p is 0. In other cases of formula (IE), $X^3$ is a nitrogen atom, $X^1$ and $X^2$ are carbon atoms, n is 1, m is 0 and p is 0.

In some embodiments, the $R^2$ group of formula (ID), has a formula of any of (IF1)-(IF4):

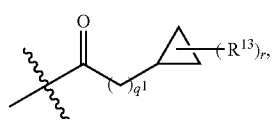

(IF1)

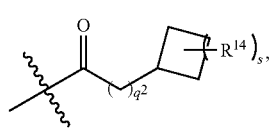

(IF2)

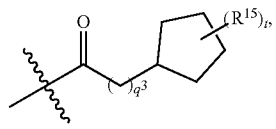

(IF3)

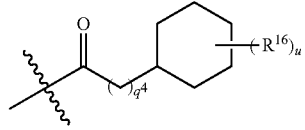

(IF4)

wherein:

$R^{13}$, $R^{14}$, $R^{15}$ and $R^{16}$ are independently selected from OH, alkyl, substituted alkyl, alkenyl, substituted alkenyl, aryl, substituted aryl, alkoxy, substituted alkoxy, —OCF$_3$, —CF$_3$, halogen, azide, amine, substituted amine, amide, cycloalkyl, substituted cycloalkyl, heterocycle and substituted heterocycle;

$q^1$ to $q^4$ are each independently an integer from 0 to 12;

r is an integer from 0 to 5;

s is an integer from 0 to 7;

t is an integer from 0 to 9; and u is an integer from 0 to 11.

In some cases the $R^2$ group of formula (ID) is of the formula (IF1). In some instances of formula (IF1), q1 is 1 and r is 0.

In some embodiments of any of formulae (I) to (ID), $R^2$ is selected from:

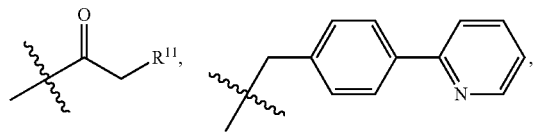

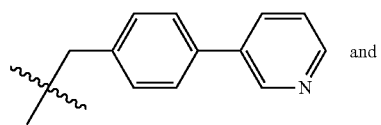
and

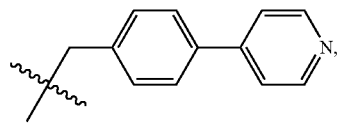

wherein $R^1$ is alkyl, substituted alkyl, $C_{3-10}$ cycloalkyl, substituted $C_{3-10}$ cycloalkyl, $C_{3-10}$ heterocycle or substituted $C_{3-10}$ heterocycle. In certain embodiments, $R^{11}$ is a lower alkyl, e.g., methyl, ethyl, propyl, isopropyl, butyl, sec-butyl, tert-butyl, pentyl or hexyl. In other embodiments, $R^{11}$ is selected from $C_{3-10}$ cycloalkyl, e.g., cyclopropyl, cyclobutyl, cyclopentyl, cyclohexyl, cycloheptyl, cyclooctyl. In some cases, $R^{11}$ is a cyclopropyl group.

In some cases of any of formulae (I) to (IB), $R^2$ is:

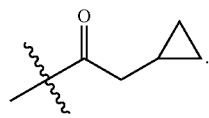 [SMILES: *C(=O)CC1CC1]

In some cases of any of formulae (I) to (IB), $R^2$ is:

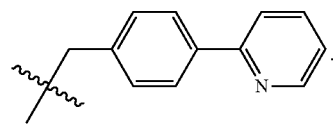 [SMILES: *Cc1ccc(-c2ccccn2)cc1]

In some embodiments of any of formulae (I) to (IB), each of $R^3$ to $R^6$ is a lower alkyl group selected from methyl, ethyl, n-propyl, isopropyl, n-butyl, isobutyl, t-butyl, pentyl and hexyl. In some embodiments of any of formulae (I) to (IB) $R^3$ is methyl. In some embodiments of any of formulae (I) to (IB) $R^4$ is methyl. In some embodiments of any of formulae (I) to (IB) $R^5$ is methyl. In some embodiments of any of formulae (I) to (IB) $R^6$ is methyl. In some embodiments of any of formulae (I) to (IB) at least two of $R^3$ to $R^6$ is methyl. In some embodiments of any of formulae (I) to (IB) at least three of $R^3$ to $R^6$ is methyl. In some embodiments, each of $R^3$, $R^4$, $R^5$ and $R^6$ are methyl groups.

In some embodiments of any of formulae (I) to (IB), the structure has the formula (II):

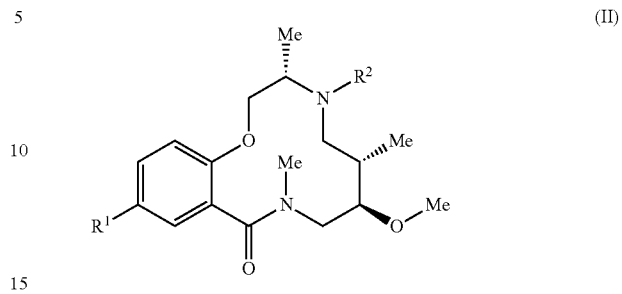

(II)

wherein:
$R^1$ is

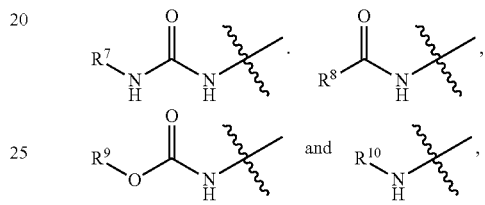

wherein $R^7$, $R^8$ and $R^9$ are each independently selected from, methyl, ethyl, propyl, isopropyl, butyl, sec-butyl, tert-butyl, pentyl, hexyl, aryl, substituted aryl, heteroaryl, substituted heteroaryl, cycloalkyl, substituted cycloalkyl, heterocycle, substituted heterocycle; and $R^{10}$ is selected from H, alkyl, substituted alkyl, aryl, substituted aryl, heteroaryl, substituted heteroaryl, cycloalkyl, substituted cycloalkyl, heterocycle and substituted heterocycle; and $R^2$ is selected from

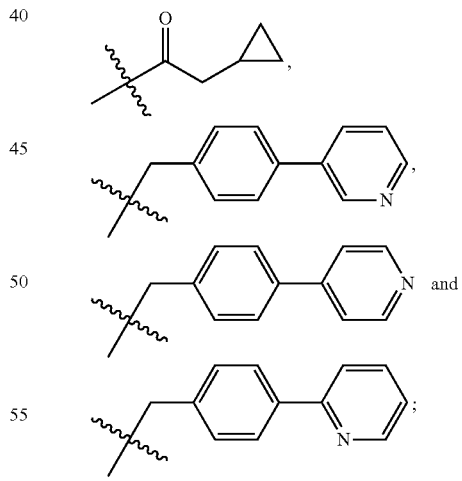

or a pharmaceutically acceptable salt thereof.
In some cases of formula (II), $R^2$ is:

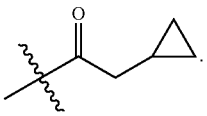

In some cases of formula (II), R² is:

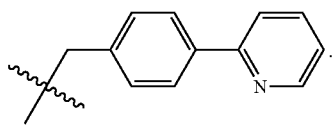

In some embodiments of formula (II), the structure has the formula (III):

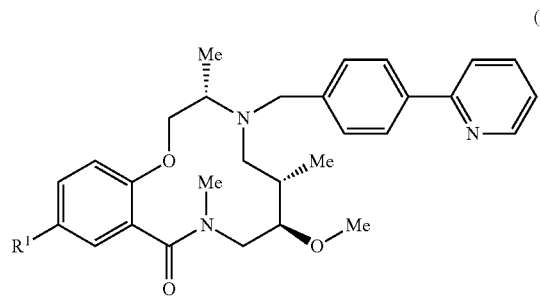

wherein:
R¹ is

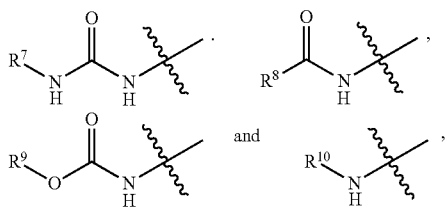

wherein:
R⁷, R⁸ and R⁹ are each independently selected from, methyl, ethyl, propyl, isopropyl, butyl, sec-butyl, tert-butyl, pentyl, hexyl, aryl, substituted aryl, heteroaryl, substituted heteroaryl, cycloalkyl, substituted cycloalkyl, heterocycle, substituted heterocycle;
or a pharmaceutically acceptable salt thereof.

In some embodiments of formulae (II) or (III), R¹ is selected from:

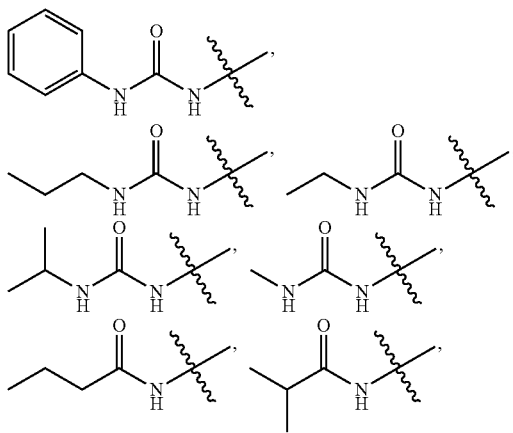

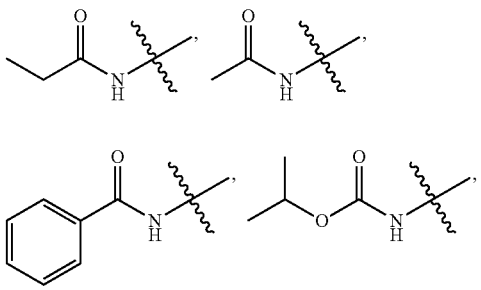

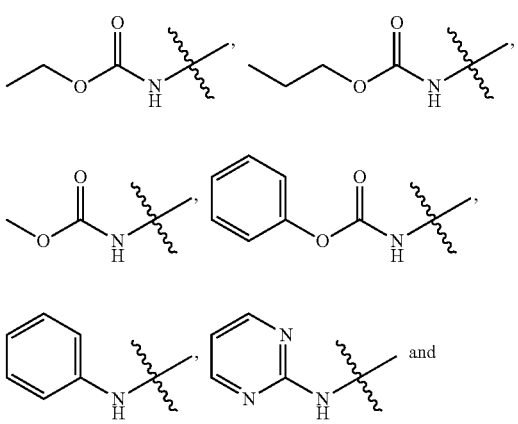

In certain cases of formula (II) or (III), R¹ is selected from:

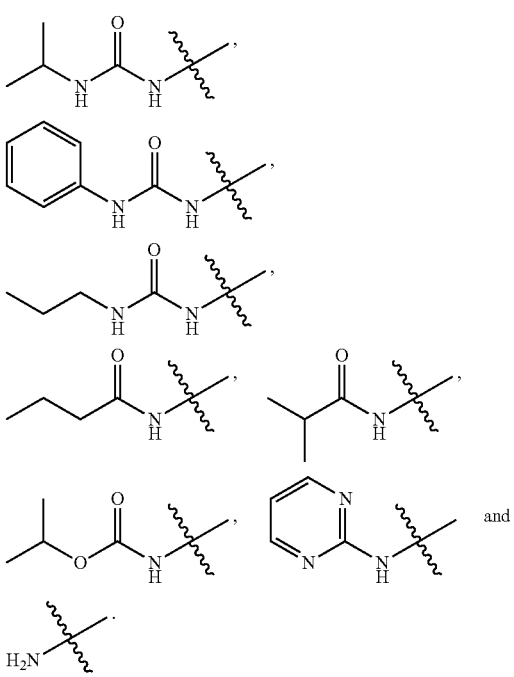

In some embodiments, the subject BAF modulating compound is described by the structure of any one of compounds (1) to (10).

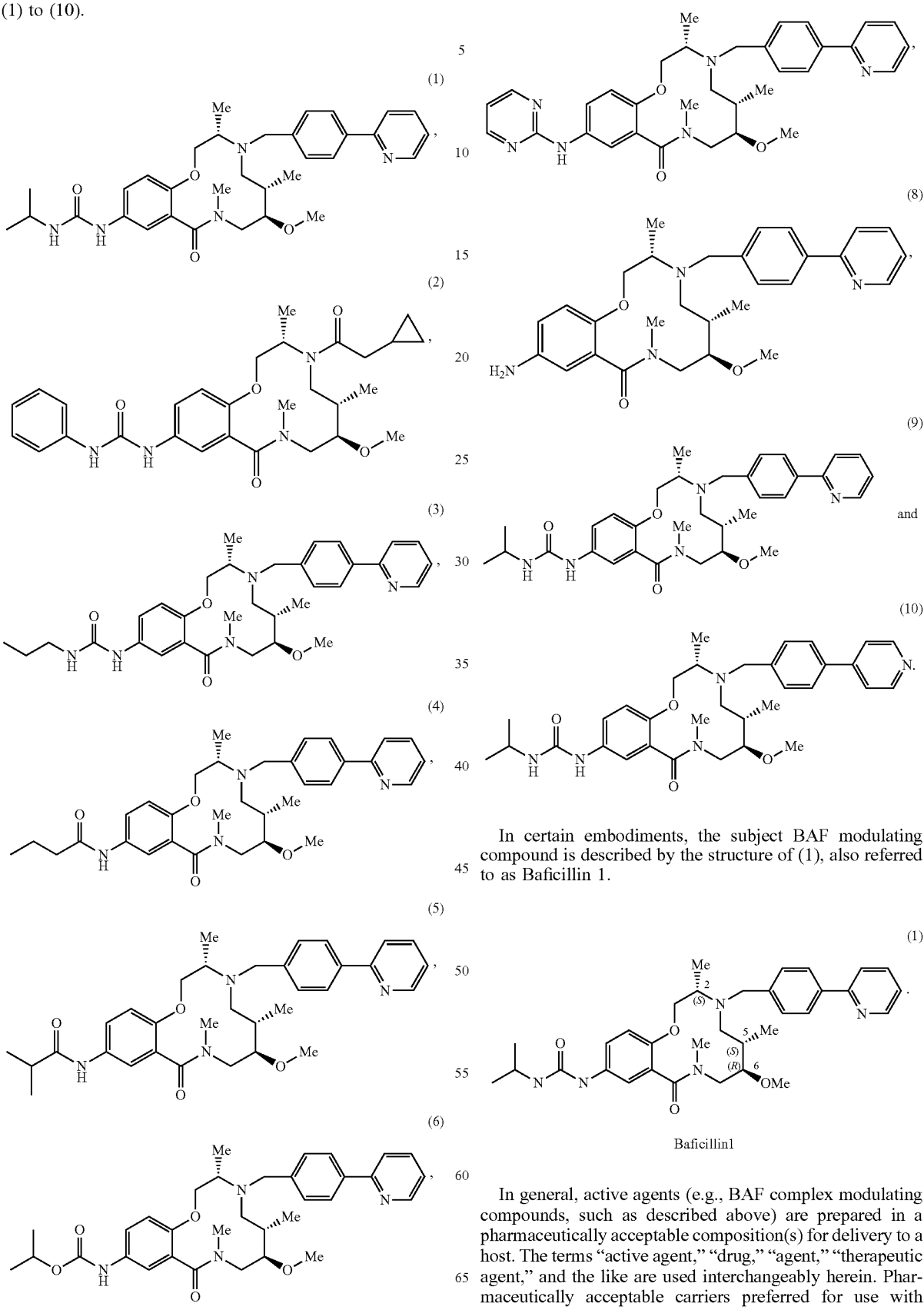

In certain embodiments, the subject BAF modulating compound is described by the structure of (1), also referred to as Baficillin 1.

In general, active agents (e.g., BAF complex modulating compounds, such as described above) are prepared in a pharmaceutically acceptable composition(s) for delivery to a host. The terms "active agent," "drug," "agent," "therapeutic agent," and the like are used interchangeably herein. Pharmaceutically acceptable carriers preferred for use with active agents (e.g., BAF complex modulating compounds, such as described above; and optionally one or more additional therapeutic agents) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent may also be lyophilized using means well known in the art, for subsequent reconstitution and use according to the invention.

Formulations

Active agents (e.g., BAF complex modulating compounds, such as described above; and optionally one or more additional therapeutic agents) are administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. For the purposes of the following description of formulations, "active agent" includes a BAF complex modulating compounds, such as described above, and optionally one or more additional therapeutic agent.

In a subject method, active agents (e.g., BAF complex modulating compounds, such as described above; and optionally one or more additional therapeutic agents) may be administered to the host using any convenient means capable of resulting in the desired degree of reactivation of latent immunodeficiency virus. Thus, active agents (e.g., BAF complex modulating compounds, such as described above; and optionally one or more additional therapeutic agents) can be incorporated into a variety of formulations for therapeutic administration. More particularly, active agents (e.g., BAF complex modulating compounds, such as described above; and optionally one or more additional therapeutic agents) can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent (e.g., BAF complex modulating compounds, such as described above; and optionally one or more additional therapeutic agents) is formulated as a gel, as a solution, or in some other form suitable for intravaginal administration. In a further exemplary embodiment, an active agent (e.g., BAF complex modulating compounds, such as described above; and optionally one or more additional therapeutic agents) is formulated as a gel, as a solution, or in some other form suitable for rectal (e.g., intrarectal) administration.

In pharmaceutical dosage forms, an active agent (e.g., BAF complex modulating compounds, such as described above; and optionally one or more additional therapeutic agents) may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an agent (e.g., BAF complex modulating compounds, such as described above; and optionally one or more additional therapeutic agents) is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. For oral preparations, an active agent (e.g., BAF complex modulating compounds, such as described above; and optionally one or more additional therapeutic agents) can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent (e.g., BAF complex modulating compounds, such as described above; and optionally one or more additional therapeutic agents) can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. An active agent (e.g., BAF complex modulating compounds, such as described above; and optionally one or more additional therapeutic agents) can be utilized in aerosol formulation to be administered via inhalation. An active agent (e.g., BAF complex modulating compounds, such as described above; and optionally one or more additional therapeutic agents) can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

Unit dosage forms for intravaginal or intrarectal administration such as syrups, elixirs, gels, and suspensions may be provided wherein each dosage unit, for example, teaspoonful, tablespoonful, tablet, unit gel volume, or suppository, contains a predetermined amount of the composition containing one or more active agents.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g. about 1% to about 2%.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration is formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

An active agent will in some embodiments be formulated for rectal delivery. A subject formulation for intrarectal administration is formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel. A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrroli- done or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 mg to about 1000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, or from about 500 mg to about 1000 mg of an active agent (e.g., BAF complex modulating compounds, such as described above; and optionally one or more additional therapeutic agents) can be administered in a single dose.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent (e.g., BAF complex modulating compounds, such as described above; and optionally one or more additional therapeutic agents) is administered. In other embodiments, multiple doses of an active agent (e.g., BAF complex modulating compounds, such as described above; and optionally one or more additional therapeutic agents) are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

Routes of Administration

An active agent (e.g., BAF complex modulating compounds, such as described above; and optionally one or more additional therapeutic agents) is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. In some embodiments, an active agent is administered via an intravaginal route of administration. In other embodiments, an active agent is administered via an intrarectal route of administration. Routes of administration may be combined, if desired, or adjusted depending upon the agent and/or the desired effect. The composition can be administered in a single dose or in multiple doses. An active agent (e.g., BAF complex modulating compounds, such as described above; and optionally one or more additional therapeutic agents) can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent (e.g., BAF complex modulating compounds, such as described above; and optionally one or more additional therapeutic agents) can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the number of viral particles per unit blood. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys), that are susceptible to immunodeficiency virus (e.g., HIV) infection. In many embodiments, the hosts will be humans.

Combination Therapies

BAF complex modulating compounds, such as described above, can be administered to an individual in combination (e.g., in the same formulation or in separate formulations) with at least one additional therapeutic agent ("combination therapy"). BAF complex modulating compounds, such as described above, can be administered in admixture with at least one additional therapeutic agent or can be administered in separate formulations. When administered in separate formulations, a BAF complex modulating compound, and at least one additional therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more.

Therapeutic agents that can be administered in combination therapy with a BAF complex modulating compound include, e.g., anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat viral infections. In some embodiments, patients with a viral or bacterial infection are treated with a combination of a BAF complex modulating compound, and one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), zidovudine/lamivudine (Combivir), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), lopinavir/ritonavir (Kaletra), trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

In some embodiments, a synergistically effective amount of a BAF complex modulating compound in combination therapy with two or more anti-HIV agents is administered. For example, a synergistically effective amount of a BAF complex modulating compound in combination therapy with one, two, or three nucleoside reverse transcriptase inhibitors (e.g., Combivir, Epivir, Hivid, Retrovir, Videx, Zerit, Ziagen, etc.) can be administered. A synergistically effective amount of a BAF complex modulatory compound in combination therapy with one or two non-nucleoside reverse transcriptase inhibitors (e.g., Rescriptor, Sustiva, Viramune, etc.) can be administered. A synergistically effective amount of a BAF complex modulatory compound in combination therapy with one or two protease inhibitors (e.g., Agenerase, Crixivan, Fortovase, Invirase, Kaletra, Norvir, Viracept, etc.) can be administered. A synergistically effective amount of a BAF complex modulatory compound in combination therapy with a protease inhibitor and a nucleoside reverse transcriptase inhibitor can be administered. A synergistically effective amount of a BAF complex modulatory compound in combination therapy with a protease inhibitor, a nucleoside reverse transcriptase inhibitor, and a non-nucleoside reverse transcriptase inhibitor can be administered. A synergistically effective amount of a BAF complex modulatory compound in combination therapy with a protease inhibitor and a non-nucleoside reverse transcriptase inhibitor can be administered. Other combinations of a synergistically effective amount of a BAF complex modulatory compound with one or more of a protease inhibitor, a nucleoside reverse transcriptase inhibitor, and a non-nucleoside reverse transcriptase inhibitor may be administered.

In some embodiments, a subject treatment method involves administering: a) a BAF complex modulatory agent; and b) an agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a subject treatment method involves administering: a) a BAF complex modulatory compound; and b) an HIV inhibitor, where suitable HIV inhibitors include, but are not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (e.g., CXCR4, CCR5) inhibitors, and hydroxyurea.

Nucleoside reverse transcriptase inhibitors include, but are not limited to, abacavir (ABC; ZIAGEN™), didanosine (dideoxyinosine (ddI); VIDEX™), lamivudine (3TC; EPIVIR™), stavudine (d4T; ZERIT™, ZERIT XR™), zalcitabine (dideoxycytidine (ddC); HMD™), zidovudine (ZDV, formerly known as azidothymidine (AZT); RETROVIR™), abacavir, zidovudine, and lamivudine (TRIZIVIR™), zidovudine and lamivudine (COMBIVIR™), and emtricitabine (EMTRIVA™). Nucleotide reverse transcriptase inhibitors include tenofovir disoproxil fumarate (VIREAD™). Non-nucleoside reverse transcriptase inhibitors for HIV include, but are not limited to, nevirapine (VIRAMUNE™), delavirdine mesylate (RESCRIPTOR™), and efavirenz (SUSTIVA™).

Protease inhibitors (PIs) for treating HIV infection include amprenavir (AGENERASE™), saquinavir mesylate (FORTOVASE™, INVIRASE™), ritonavir (NORVIR™), indinavir sulfate (CRIXIVAN™), nelfmavir mesylate (VIRACEPT™), lopinavir and ritonavir (KALETRA™), atazanavir (REYATAZ™), and fosamprenavir (LEXIVA™) Fusion inhibitors prevent fusion between the virus and the cell from occurring, and therefore, prevent HIV infection and multiplication. Fusion inhibitors include, but are not limited to, enfuvirtide (FUZEON™), Lalezari et al., New England J. Med., 348:2175-2185 (2003); and maraviroc (SELZENTRY™, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS™, Merck); and elvitegravir (GS 9137, Gilead Sciences).

Maturation inhibitors include, e.g., bevirimat (3β-(3-carboxy-3-methyl-butanoyloxy) lup-20(29)-en-28-oic acid); and Vivecon (MPC9055).

In some embodiments, a subject treatment method involves administering: a) a BAF complex modulatory compound; and b) one or more of: (1) an HIV protease inhibitor selected from amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859; (2) an HIV non-nucleoside inhibitor of reverse transcriptase selected from capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806; (3) an HIV nucleoside inhibitor of reverse transcriptase selected from zidovudine, emtricitabine, didanosine, stavudine, zalcitabine, lamivudine, abacavir, amdoxovir, elvucitabine, alovudine, MIV-210, racivir (@-FTC), D-d4FC, emtricitabine, phosphazide, fozivudine tidoxil, apricitibine (AVX754), amdoxovir, KP-1461, and fosalvudine tidoxil (formerly HDP 99.0003); (4) an HIV nucleotide inhibitor of reverse transcriptase selected from tenofovir and adefovir; (5) an HIV integrase inhibitor selected from curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-538158, GSK364735C, BMS-707035, MK-2048, and BA 011; (6) a gp41 inhibitor selected from enfuvirtide, sifuvirtide, FB006M, and TRI-1144; (7) a CXCR4 inhibitor, such as AMD-070; (8) an entry inhibitor, such as SP01A; (9) a gp120 inhibitor, such as BMS-488043 and/or BlockAide/CR; (10) a G6PD and NADH-oxidase inhibitor, such as immunitin; (11) a CCR5 inhibitors selected from the group consisting of aplaviroc, vicriviroc, maraviroc, PRO-140, INCB15050, PF-232798 (Pfizer), and CCR5 mAb004; (12) another drug for treating HIV selected from BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDXO10 (ipilimumab), PBS 119, ALG 889, and PA-1050040 (PA-040); (13) any combinations or mixtures of the above.

For example, in some embodiments, a subject treatment method involves administering: a) a synergistically effective amount of a BAF complex modulatory compound; and b) one or more of: i) amprenavir (Agenerase; (3S)-oxolan-3-yl N-[(2S,3R)-3-hydroxy-4-[N-(2-methylpropyl)(4-aminobenzene)sulfonamido]-1-phenylbutan-2-yl]carbamate) in an amount of 600 mg or 1200 mg twice daily; ii) tipranavir (Aptivus; N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)pyridine-2-sulfonamide) in an amount of 500 mg twice daily; iii) indinavir (Crixivan; (2S)-1-[(2S,4R)-4-benzyl-2-hydroxy-4-{[(1S,2R)-2-hydroxy-2,3-dihydro-1H-inden-1-yl]carbamoyl}butyl]-N-tert-butyl-4-(pyridin-3-ylmethyl)piperazine-2-carboxamide) in an amount of 800 mg three times daily; iv) saquinavir (Invirase; 2S)-N-[(2S,3R)-4-[(3S)-3-(tert-butylcarbamoyl)-decahydroisoquinolin-2-yl]-3-hydroxy-1-phenylbutan-2-yl]-2-(quinolin-2-ylformamido)butanediamide) in an amount of 1,000 mg twice daily; v) lopinavir and ritonavir (Kaleta; where lopinavir is 2S)-N-[(2S,4S,5S)-5-[2-(2,6-dimethylphenoxy) acetamido]-4-hydroxy-1,6-diphenylhexan-2-yl]-3-methyl-2-(2-oxo-1,3-diazinan-1-yl)butanamide; and ritonavir is 1,3- thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate) in an amount of 133 mg twice daily; vi) fosamprenavir (Lexiva; {[(2R,3S)-1-[N-(2-methylpropyl) (4-aminobenzene)sulfonamido]-3-({[(3S)-oxolan-3-yloxy]carbonyl}amino)-4-phenylbutan-2-yl]oxy}phosphonic acid) in an amount of 700 mg or 1400 mg twice daily); vii) ritonavir (Norvir) in an amount of 600 mg twice daily; viii) nelfinavir (Viracept; (3S,4aS,8aS)-N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide) in an amount of 750 mg three times daily or in an amount of 1250 mg twice daily; ix) Fuzeon (Acetyl-YTSLIHSLIEESQNQ QEKNEQELLELDKWASLWNWF-amide) (SEQ ID NO:29) in an amount of 90 mg twice daily; x) Combivir in an amount of 150 mg lamivudine (3TC; 2',3'-dideoxy-3'-thiacytidine) and 300 mg zidovudine (AZT; azidothymidine) twice daily; xi) emtricitabine (Emtriva; 4-amino-5-fluoro-1-[(2R,5S)-2-(hydroxymethyl)-1,3-oxathiolan-5-yl]-1,2-dihydropyrimidin-2-one) in an amount of 200 mg once daily; xii) Epzicom in an amount of 600 mg abacavir (ABV; {(1S,4R)-4-[2-amino-6-(cyclopropylamino)-9H-purin-9-yl]cyclopent-2-en-1-yl}methanol) and 300 mg 3TC once daily; xiii) zidovudine (Retrovir; AZT or azidothymidine) in an amount of 200 mg three times daily; xiv) Trizivir in an amount of 150 mg 3TC and 300 mg ABV and 300 mg AZT twice daily; xv) Truvada in an amount of 200 mg emtricitabine and 300 mg tenofovir (({[(2R)-1-(6-amino-9H-purin-9-yl)propan-2-yl]oxy}methyl)phosphonic acid) once daily; xvi) didanosine (Videx; 2',3'-dideoxyinosine) in an amount of 400 mg once daily; xvii) tenofovir (Viread) in an amount of 300 mg once daily; xviii) abacavir (Ziagen) in an amount of 300 mg twice daily; xix) atazanavir (Reyataz; methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl]carbamoyl}-2,2-dimethylpropyl]carbamate) in an amount of 300 mg once daily or 400 mg once daily; xx) lamivudine (Epivir) in an amount of 150 mg twice daily; xxi) stavudine (Zerit; 2'-3'-didehydro-2'-3'-dideoxythymidine) in an amount of 40 mg twice daily; xxii) delavirdine (Rescriptor; N-[2-({4-[3-(propan-2-ylamino)pyridin-2-yl]piperazin-1-yl}carbonyl)-1H-indol-5-yl]methanesulfonamide) in an amount of 400 mg three times daily; xxiii) efavirenz (Sustiva; (4S)-6-chloro-4-(2-cyclopropylethynyl)-4-(trifluoromethyl)-2,4-dihydro-1H-3,1-benzoxazin-2-one) in an amount of 600 mg once daily); xxiv) nevirapine (Viramune; 11-cyclopropyl-4-methyl-5,11-dihydro-6H-dipyrido[3,2-b:2',3'-e][1,4]diazepin-6-one) in an amount of 200 mg twice daily); xxv) bevirimat; and xxvi) Vivecon.

Kits, Containers, Devices, Delivery Systems

Kits with unit doses of a BAF complex modulatory agent, e.g. in oral, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating an immunodeficiency virus (e.g., HIV) infection. Suitable active agents and unit doses are those described herein above.

In some embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

The present disclosure provides a delivery system comprising an active agent that modulates BAF complex, where the active agent reactivates latent immunodeficiency virus in an immunodeficiency virus-infected cell. In some embodiments, the delivery system is a delivery system that provides for injection of a formulation comprising an active agent subcutaneously, intravenously, or intramuscularly.

In some embodiments, an active agent is packaged for oral administration. The present disclosure provides a packaging unit comprising daily dosage units of an active agent. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a subject delivery system comprises an injection device. Exemplary, non-limiting drug delivery devices include injections devices, such as pen injectors, and needle/syringe devices. In some embodiments, the present disclosure provides an injection delivery device that is pre-loaded with a formulation comprising a BAF complex modulatory agent. For example, a subject delivery device comprises an injection device pre-loaded with a single dose of a BAF complex modulatory compound. A subject injection device can be re-usable or disposable. Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; and the like. The medication delivery pen can be disposable, or reusable and refillable.

In some embodiments, the delivery system comprises a first container comprising a composition comprising a BAF complex modulatory compound; and a second container comprising a composition comprising a second HIV therapeutic agent, e.g., as described above. The first and second containers can be, e.g., syringes. The delivery system can further comprise needles for use together with the syringes.

Pessaries, tablets and suppositories are other examples of drug delivery systems which can be used in connection with a subject treatment method. These systems have been described extensively in the literature.

Bioadhesive microparticles constitute still another drug delivery system suitable for use in the present invention. This system is a multi-phase liquid or semi-solid preparation which does not seep from the vagina or rectum as do many suppository formulations. The substances cling to the wall of the vagina or rectum and release the drug over a period of time. Many of these systems were designed for nasal use but can be used in the vagina or rectum as well (e.g. U.S. Pat. No. 4,756,907). The system may comprise microspheres with an active agent; and a surfactant for enhancing uptake of the drug. The microparticles have a diameter of 10 m to 100 μm and can be prepared from starch, gelatin, albumin, collagen, or dextran.

Another system is a container (e.g., a tube) comprising a subject formulation that is adapted for use with an applicator. An active is incorporated into creams, lotions, foams, paste, ointments, and gels which can be applied to the vagina or rectum using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal or rectal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

Subjects Suitable for Treatment

The methods of the present disclosure are suitable for treating individuals who have an immunodeficiency virus infection, e.g., who have been diagnosed as having an immunodeficiency virus infection.

The methods of the present disclosure are suitable for treating individuals who have an HIV infection (e.g., who have been diagnosed as having an HIV infection), and individuals who are at risk of contracting an HIV infection. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals. Individuals suitable for treatment include individuals infected with, or at risk of becoming infected with, HIV-1 and/or HIV-2 and/or HIV-3, or any variant thereof.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

I. INTRODUCTION

Since the discovery of HIV-1 as the causative agent of AIDS in 1983[1], enormous progress has been made in treating HIV-1 infections and prolonging the lifespan of HIV-1 infected individuals. State of the art treatment is a cocktail of drugs acting on different viral targets, known as combination Anti-Retroviral Therapy (c-ART). c-ART is extremely effective at suppressing HIV-1 to undetectable levels, preventing progression to AIDS; however, treatment must be maintained for life and as of yet, HIV-1 eradication is not achievable[2,3]. Despite being highly efficient in stopping active viral replication, anti-retroviral drugs do not target latently infected cells that harbor replication competent but transcriptionally silent proviruses. Latently infected cells persist in the body for life and, not being targeted by either c-ART or immune cells, they constitute the viral reservoir[4-6]. When these cells are activated, transcription from latent HIV-1 provirus is induced and in the absence of c-ART, viral replication rebounds[7-11].

Currently, there are two major non-redundant strategies to eliminate this population of latently infected cells in HIV-1-infected individuals[12-15]. The first approach is harnessing the immune system to eliminate latently infected cells[16-20]; the second, also known as the "shock and kill" strategy, is aimed at inducing HIV-1 transcription in latently infected cells such that all cells harboring replication competent virus can be targeted by the immune system[21-24].

HIV-1 latency is established and maintained through complex genetic and epigenetic mechanisms that create a specific repressive chromatin configuration at the viral promoter or 5'-LTR[25,26]. Active HIV-1 transcription is driven by Tat and its multiple activating co-factor complexes, while HIV-1 latency is driven through epigenetic regulators that maintain increased nucleosome occupancy at the 5'-LTR[27-30]. Histone deacetylases (HDACs) play a prominent role in the repressive chromatin environment that drives HIV-1 latency and as such, HDAC inhibitors are able to reverse HIV-1 latency in in vitro and ex-vivo models[11,31-38]. Results from clinical trials, however, indicate that the HDAC inhibitors tested are unable to significantly reduce the frequency of latently infected cells[32,39-41 42]. Among the alternate epigenetic targets being investigated for reversing HIV-1 latency, one potential candidate is the mammalian SWI/SNF chromatin remodeling complex, BAF, which has been shown to contribute to HIV-1 transcriptional repression[43-45]. BAF complexes are multisubunit ATP-dependent chromatin remodelers known for their roles in development and cancer[46-48]. In latent cells harboring HIV-1 proviruses, BAF complexes are required for maintaining increased nucleosome occupancy immediately downstream of the HIV-1 transcription start site[43]. During latency reversal, the closely related PBAF complex, which shares many of the same subunits, replaces BAF and directly or indirectly promotes removal of the repressive Nuc-1, activating HIV-1 transcription[43,45,49-52]. Consistent with the pivotal role of the BAF complex in HIV-1 latency, a recent report demonstrated that the latency reversal activity of BRD4 bromodomain inhibitors is due to the requirement for a short BRD4 isoform that recruits BAF to the HIV-1 5' LTR[53].

Inhibitors specifically targeting the ARID1A subunit-containing BAF complex (but not PBAF) would be invaluable as HIV-1 latency reversal agents. To address this need for BAF-specific inhibitors, we recently reported a medium throughput screen using qRT-PCR to identify compounds that alter the transcription of BAF target genes in mouse embryonic stem cells (ESCs)[54]. Several compounds identified from this screen displayed an ability to reverse HIV-1 latency; however, many of these compounds have known targets besides BAF, raising the possibility for toxic off-target effects[55]. To identify specific and nontoxic small molecule inhibitors of the BAF complex, we developed a high throughput assay specifically designed for screening large libraries of diverse small molecules in ESCs. From a screen of almost 350,000 compounds, we identified a novel 12-membered macrolactam scaffold with low toxicity in cells and the ability to regulate a panel of BAF target genes. These macrolactams are able to reverse HIV-1 latency in several relevant in vitro cell line and primary cell models of HIV-1 latency. In addition, they enhance the activity of other clinically used latency reversal agents targeting HDACs and PKC. Target identification experiments implicate ARID1A-containing BAF complexes as the primary target, and the compounds act to reverse HIV-1 latency by reducing repressive nucleosome occupancy at the 5' LTR.

II. MATERIALS & METHODS

A. Experimental Model and Subject Details
1. E14 ESC and Bmi-luc ESC culture: ESCs were cultured in ESC media: (DMEM (Gibco), 15% ES tested FBS (Applied Stem Cell), 1% HEPES (Gibco), 1% Sodium pyruvate (Gibco), 1% Pen/Strep (Invitrogen), 1% Glutamine (Invitrogen), 1% non-essential amino acids (Gibco) and 0.1% Lif-condition media from Cos-Lif cells. Media was changed daily. After 72 h, the cells were split with 0.25% Trypsin-EDTA (Gibco) and plated at the same density on tissue culture plates that had been treated with 0.1% gelatin in water (Millipore) for 30 minutes and removed.
2. Arid1af/f:CreERT2 ESCs were cultured in Knockout™ DMEM (Thermo Fisher Sci #10829018) supplemented with 15% ESC-Sure FBS serum (Applied Stem Cell #ASM-5007) and Knockout™ Serum Replacement (Thermo Fisher Sci #10828028), 2 mM L-glutamine (Gibco #35050061), 10 mM HEPES (Gibco #15630080), 1 mM sodium pyruvate (Gibco #11360070), 100 U/mL penicillin/streptomycin (Gibco #15140122), 0.1 mM non-essential amino acids (Gibco #11140050), 0.1 mM beta-mercaptoethanol (Gibco 21985023) and leukemia inhibitory factor (LIF). ESCs were maintained on gamma-irradiated mouse embryonic fibroblast (MEF) feeders at 37° C., 5% CO2 with daily media changes and passaged every other day.
3. HEK293T Cell Culture: HEK293T cells were cultured in (DMEM (Gibco), 10% FBS (Omega), 1% Sodium pyruvate (Gibco), 1% Pen/Strep (Invitrogen). After 72 h, the cells were split 1:4 with 0.25% Trypsin-EDTA (Gibco).
4. A549 Cell Culture: A549 cells were cultured in (DMEM (Gibco), 10% FBS (Omega), 1% Sodium pyruvate (Gibco), 1% Pen/Strep (Invitrogen). After 72 h, the cells were split 1:4 with 0.25% Trypsin-EDTA (Gibco).
5. HepG2 Cell Culture: HepG2 cells were cultured in (DMEM (Gibco), 10% FBS (Omega), 1% Sodium pyruvate (Gibco), 1% Pen/Strep (Invitrogen). After 72 h, the cells were split 1:4 with 0.25% Trypsin-EDTA (Gibco) and replated.
6. Jurkat Cell Culture: J-Lat A2 and J-Lat 11.1 cells were cultured in RPMI-1640 medium (Sigma Aldrich) supplemented with 10% FBS and 100 µg/ml penicillin-streptomycin at 37° C. in a humidified 95% air-5% $CO_2$ atmosphere. After 72 h, the cells were diluted to a concentration of $2 \times 10^5$ cells/mL with fresh media.
7. Primary human CD4+ T cells: Primary human CD4+ T cells from either healthy donors or HIV+ patients were obtained via either blood donations (buffy coats) or leukapheresis respectively. PBMCs were isolated by Ficoll gradient followed by isolation (negative selection) of CD4+ T cells by RosseteSep kit (Stem Cell Technologies) or by negative selection with EasySep (Stem Cell Technologies) from healthy donors or HIV+ patients respectively. CD4+ T cells were cultured at a density of $1-1.5 \times 10^6$/ml in RPMI-1640 medium supplemented with 7% FBS and 100 µg/ml penicillin-streptomycin at 37° C. in a humidified 95% air-5% $CO_2$ atmosphere before treatment with compounds or incubation in presence of αCD3/αCD28 beads.

B. Method Detail
1. Bmi1-Luciferase Reporter Cell Line:
Low passage mESCs from 129 mice (20 million, p10) were electroporated with 40 µg of a linearized construct consisting of 2 kb homology upstream of the Bmi1 locus, firefly luciferase at exon 1 of Bmi1 followed by loxP neo and a 6 kb 3' homology arm with thymidine kinase outside the homology arms. The cells were plated on 10 gelatin treated plates (60 mm) of irradiated neo resistant MEFs and selected with G418 and ganciclovir for 5 days. 384 colonies were selected, trypsinized and replated in gelatin treated 24-well plates for expansion. The cells were split and DNA was isolated for digestions with EcoRI or BamHI. We confirmed the successful homologous recombination in 7 out 384 colonies using Southern blot analysis at both the 5' (EcoRI) and 3' (BamHI) end (see Table S2 of Marian et al., "Small Molecule Targeting of Specific BAF (mSWI/SNF) Complexes for HIV Latency Reversal," Cell Chem. Biol. (Dec. 20, 2018) 25: 1443-1445). We deleted the neomycin cassette using transfected Cre recombinase and confirmed the excision at all clones using a second round of Southern blot analysis at the 3' end (BamHI).
2. Lentiviral Infection
HEK293T cells were transfected with lentiviral constructs along with lentiviral packaging vectors pMD2.G and psPAX2. After 48 h, supernatants were collected and virus isolated using ultracentrifugation at 20,000 r.p.m. for 2 h. Viral pellets were re-suspended in PBS and used to infect cell lines. Cells were selected with puromycin and harvested 72 h after infection.
3. Compound Treatment: 10,000 cells in 30 µL ESC media were plated in white 384 well CellBind plates. The cells were cultured in a 37° C., 5% $CO_2$ incubator for 24 h and 100 nL/well of 0.75 mM of positive control (Pubchem SID: 85814977) or 100 nL/well of 3.75 mM compound library (primary screen) was added via pin transfer into plates. There was no effect on assay readout at DMSO concentrations up to 0.5%. The cells were cultured in a 37° C., 5% $CO_2$ incubator for 24 h for luciferase reporter assay and 18 h for qRT-PCR assay.

4. Luciferase assay: (PubChem AID 602393 primary, PubChem AID 651717 confirmatory.) The assay plates were removed from the incubator and equilibrates for 10 minutes to room temperature. Promega SteadyGlo® solution (10 μL/well) was added to each well of the assay plates. The assay plates were mixed at 1000 rpm for 15 seconds and then incubated for 10 minutes at room temperature. The luciferase levels were read on a Perkin Elmer Envision in Ultra Sensitive Luminescence mode. Signals remained stable up to 2 hours.

5. EqRT-PCR secondary screen (PubChem AID 743180, 743177, 743176) The qRTPCR screen was performed as published[54]. In brief, 5,000 ES cells were plated on gelatin-coated 384-well tissue culture plates and cultured in a 37C, 5% $CO_2$ incubator. 24 h later, hit compounds in 100 nL DMSO were treated at eight different doses. 18 h after compound treatment cells were washed two times with 100 μL PBS and all excess PBS was removed by centrifuging the plates upside down at 1000 rpm. The Ambion® Cells-to-Ct kit was used to generate cDNA. In brief, the cells were lysed in the plate in 10 μL lysis buffer containing DNase for 10 minutes and quenched with 1 μL lysis stop buffer. The lysate (2 μL) was added to 5 μL RT reaction buffer (2x), 2.5 μL nuclease-free water and 0.5 μL Reverse transcriptase (20x) and incubated at 37° C. for 60 minutes and 95° C. for 1 minute to generate 10 μL of cDNA. cDNA (1 μL) was used in each 5 μL qPCR reaction with Roche master mix and TaqMan probes (Applied Biosystems) for Bmi1-FAM (Mm00776122_gH), Ring1a-FAM (Mm01278940_m1/4331182), or Fgf4-FAM (Mm00438916_g1/4351372) alongside actin-VIC (4352341E) for a loading control. The qPCR was run accordingly: 95° C. for 10 minutes Then 55 cycles of: 95° C. for 10 seconds followed by 60° C. for 30 seconds. The fold increase in transcription was calculated using the $\Delta\Delta C_T$ method[84].

6. Viability Assays (PubChem AID: 743188, 743189, 743190, 1053139, 1053140, 1053141)

Cell culture: HepG2, A549 and HEK293 cells were propagated to 95% confluence in DMEM containing 10% FBS 1% Pen/Strep, 1% L-Glutamine. Cells were plated at 2000 per well in 40 μL media in white tissue culture treated 384-well plates and incubated at 5% $CO_2$; 95% humidity, 37° C. for 24 hours. Compound (100 nL) was added to wells using a pin tool (CyBi Well) alongside 100 nL cytotoxic compounds, mitoxantrone (final concentration of 10 μM) as a positive control. The cells were incubated for 72 hours at 37° C., 95% humidity 5% $CO_2$. Plates were removed from the incubator, equilibrated for 15 minutes to room temperature; and 20 μL 50% Promega CellTiterGlo (diluted 1:1 with PBS, pH 7.4) was added. The plates were read on Perkin-Elmer EnVision with standard luminescence settings for 0.1 sec per well.

7. qRT-PCR Screen Confirmation and DOS Analog Library (SYBR)

50,000 mESCs were plated on gelatin coated 24-well plates. After 24 hours, the cells were treated with 30 μM of compound and incubated at 5% $CO_2$; 95% humidity, 37° C. for 18 hours. RNA was isolated using Trizol® and cDNA was synthesized from 1 μg RNA using Superscript III Reverse Transcriptase with Oligo(dT)12-18 primers (Thermo) and diluted 10× with water. 1 μL of this cDNA mixture was used for qPCR with 2×SYBR (Roche) and the following primers: Bmi1: Forward: TACCATGAATG-GAACCAGCA (SEQ ID NO:01); reverse:

```
Bmi1: Forward:
                                    (SEQ ID NO: 01)
TACCATGAATGGAACCAGCA;

reverse:
                                    (SEQ ID NO: 02)
AAAGGAAGCAAACTGGACGA, Ring1a: Forward:
                                    (SEQ ID NO: 03)
CCTGGACATGCTGAAGAACA;

reverse:
                                    (SEQ ID NO: 04)
TCCCGGCTAGGGTAGATTTT, FGF4: Forward:
                                    (SEQ ID NO: 05)
GGGTGTGGTGAGCATCTTCGGA;

reverse:
                                    (SEQ ID NO: 06)
GGTATGCGTAGGACTCGTAGGGC, Gapdh: Forward:
                                    (SEQ ID NO: 07)
TGCACCACCAACTGCTTAG;

reverse:
                                    (SEQ ID NO: 08)
GGATGCAGGGATGATGTTT.
```

Figure 4:
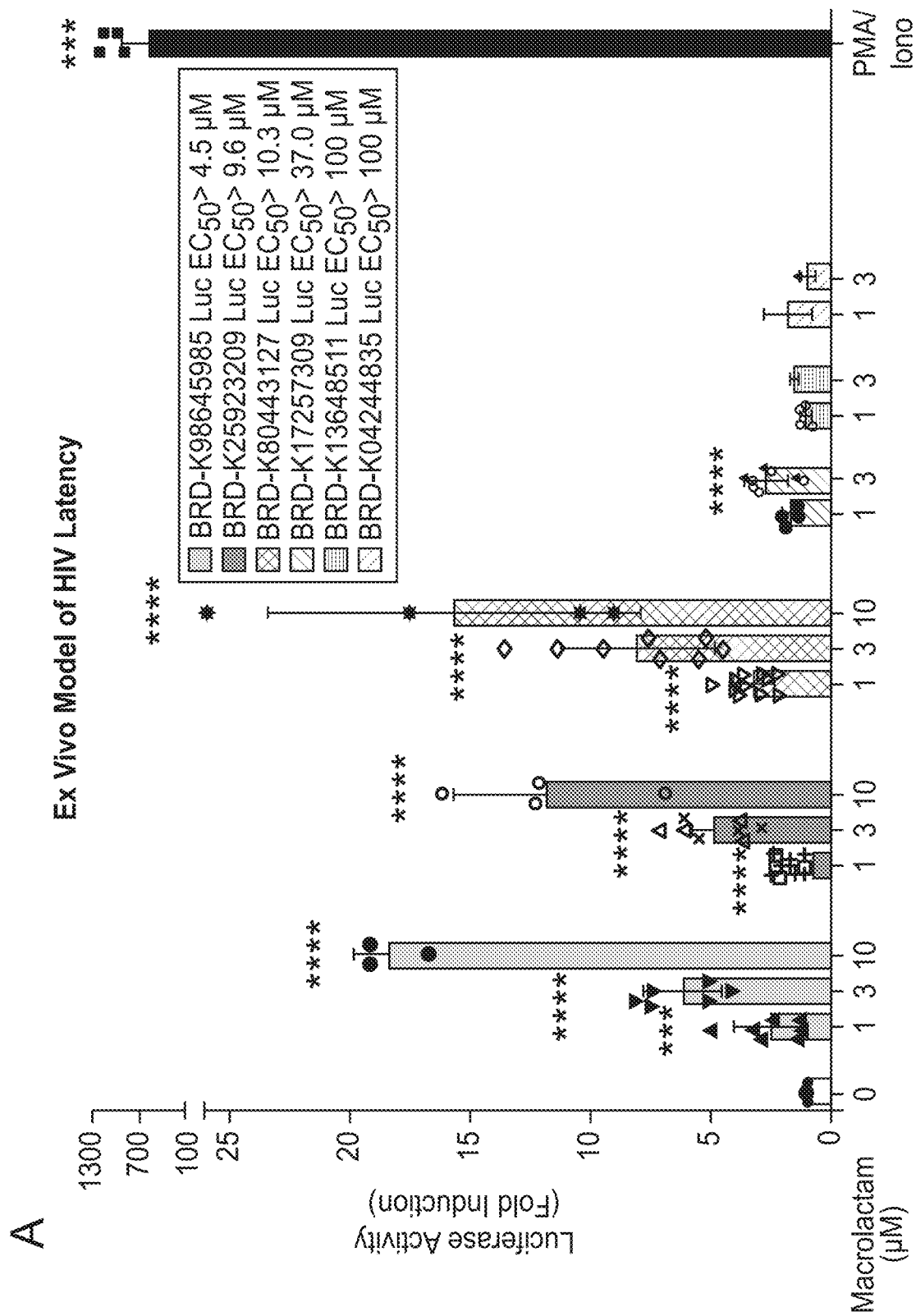
FIG. 4: 12-membered macrolactams reactivate latent HIV-1 in primary model systems of HIV-1 latency and patient samples with limited toxicity or T-cell activation. A. A panel of six macrolactams with varying $EC_{50}$ values from the Bmi1-luciferase assay were tested in an ex vivo model of HIV-1 latency using primary CD4+ T cells from healthy donors[61]. Each point represents a single experiment using T cells from at least two different healthy donors. Luciferase levels are normalized with total protein levels. Error bars represent mean±S.D. Asterisks indicate the level significance compared to untreated cells using student's T test (* $p<0.05$  $p<0.01$, * $p<0.001$, **** $p<0.0001$). B. mRNA expression levels of two BAF target genes were determined after treatment of CD4+ T cells isolated from 3 healthy donors with BRD-K80443127. Bars represent the average ±SD, Asterisks indicate the level significance compared to untreated cells using student's T test (* $p<0.05$  $p<0.01$, * $p<0.001$, **** $p<0.0001$). C. The number of apoptotic human primary CD4+ T cells in the presence of macrolactams was measured using Annexin V staining and flow cytometry analysis. Data presented as mean±S.D. of experiments performed on cells isolated from 6 healthy donors. D. Latency reversal activity of BRD-K80443127 in combination with known LRAs was assessed in the ex-vivo model of HIV-1 latency. BRD-K80443127 was used at a concentration of 5 µM alone or in combination with known LRAs at a single dose. Luciferase levels are normalized with total protein levels. Data presented as mean±S.D. of experiments performed in duplicate using cells from two healthy donors. Asterisks indicate the level significance compared to untreated cells using student's T test (* $p<0.05$  $p<0.01$, * $p<0.001$, **** $p<0.0001$). E. Cell associated HIV Pol mRNA levels were quantitated in CD4+ T cells obtained from three c-ART treated virologically suppressed HIV-1 infected patients after ex vivo treatment with BRD-K80443127 (10 µM), Prostratin (200 nM) or ⁻CD3/□CD28 dynabeads as indicated in triplicate. Bars represent average of treatments in triplicate ±SD, asterisks indicate the level of significance using one-way ANOVA followed by Tukey test ($p<0.05$). mRNA expression levels of biomarker genes of BAF activity, c-MYC and p-21 were also quantitated in the patient CD4+ T cells after treatment with DMSO or BRD-K80443127 (10 µM).
Figure 4:
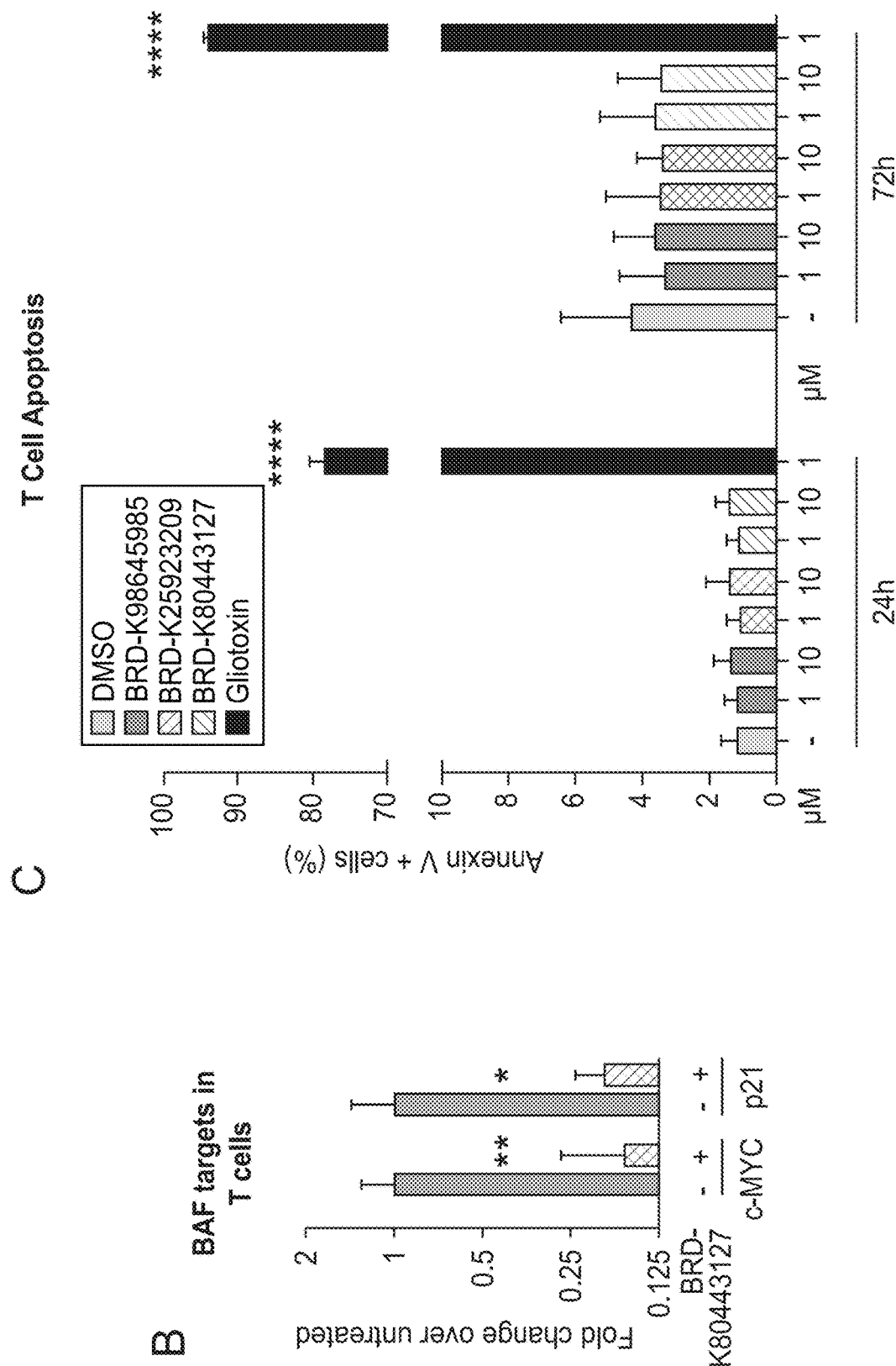
Figure 4:
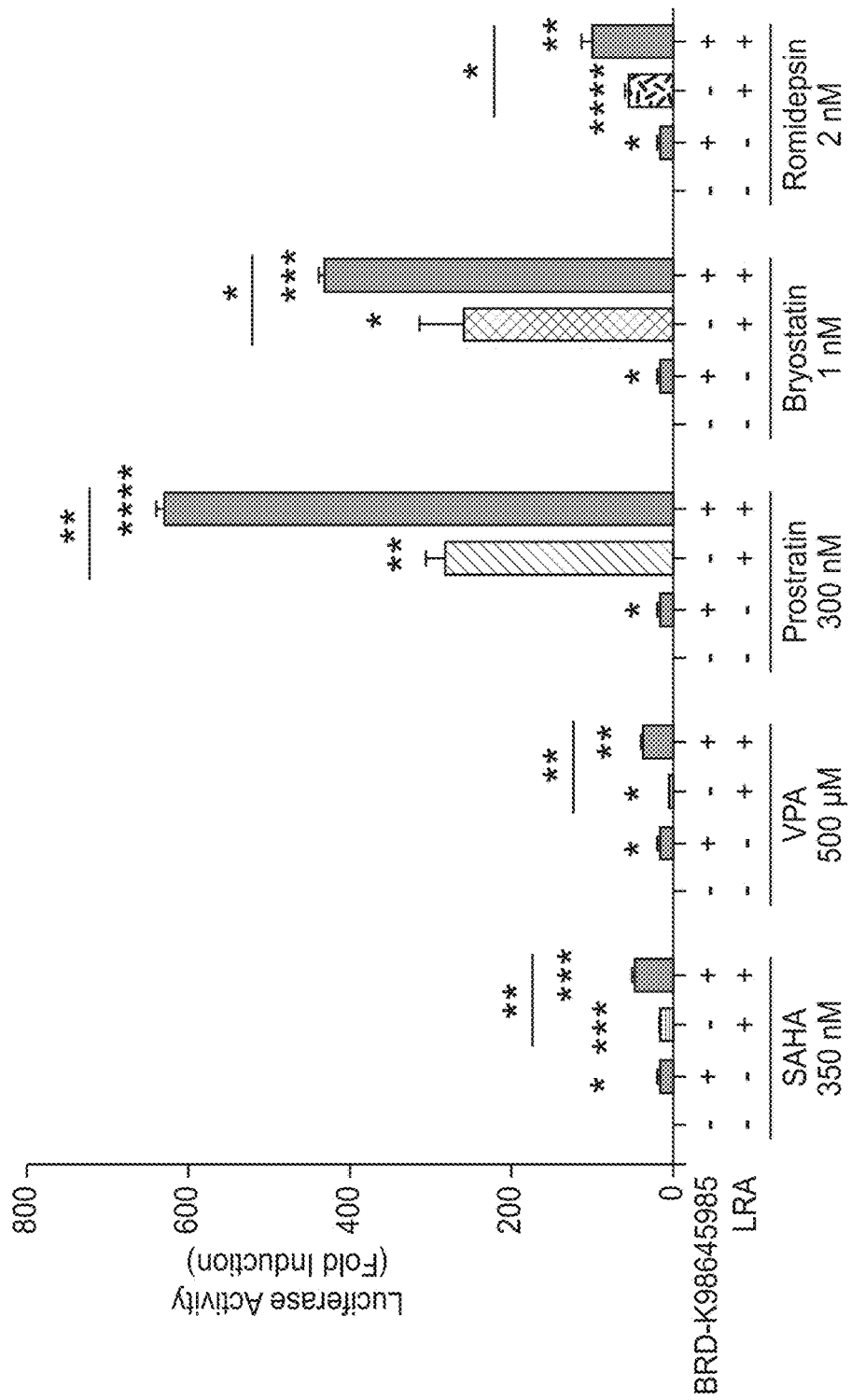
Figure 4:
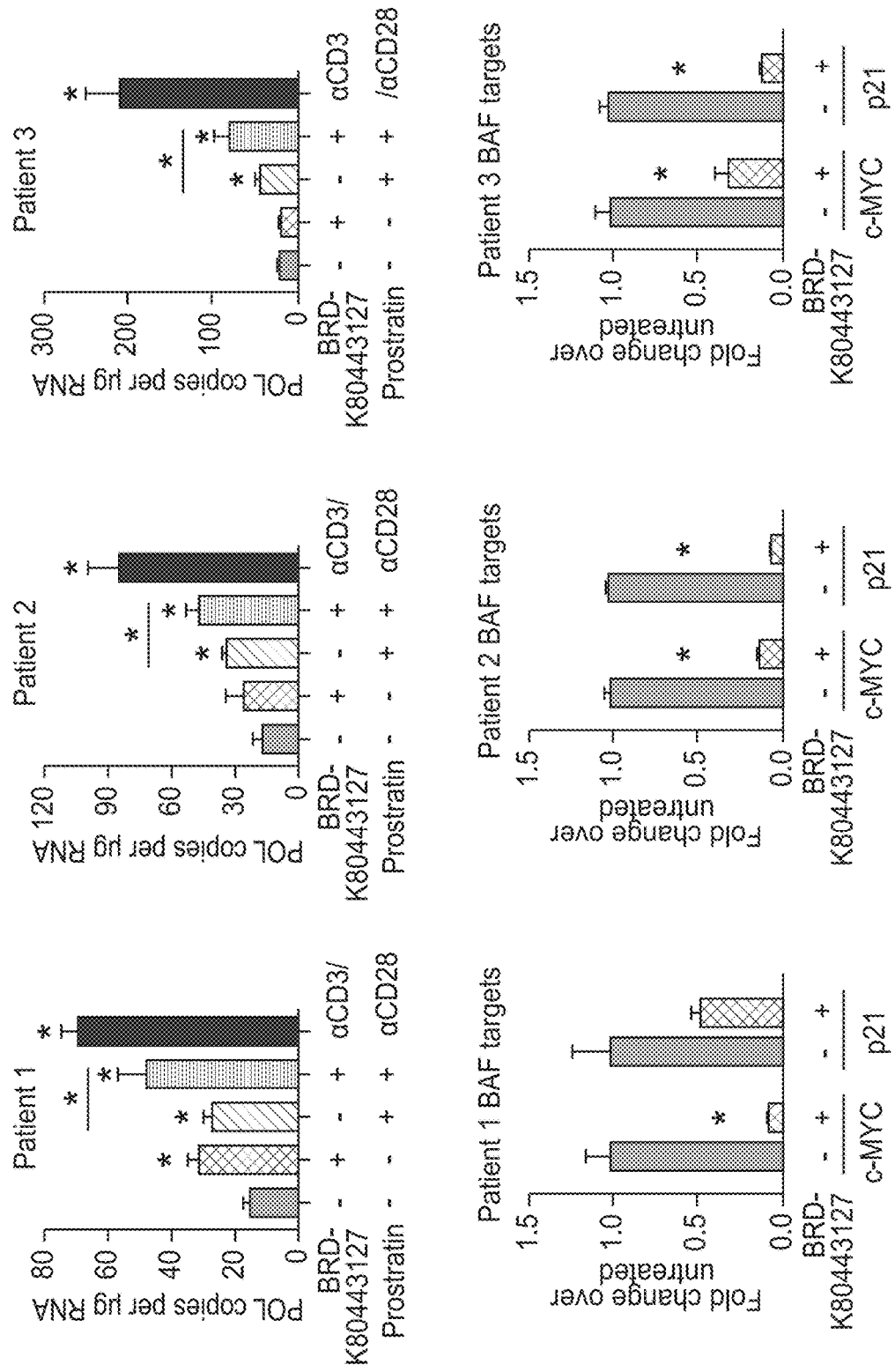

8. Chemical Synthesis of DOS analog library: The synthesis of the original DOS library was performed according to the Head-to-Tail strategy for combinatorial synthesis of multiple scaffold simultaneously[59]. For the synthesis of the 30 macrolactam library members in solution the backbone (compound 2141-017) was synthesized according to published procedures in the scheme in (FIG. S3, Marian et al., Ibid.). The synthesis of the six representative compounds used in HIV latency experiments (FIG. 4, FIG. S3 Marian et al., Ibid.) from this backbone are outlined below:

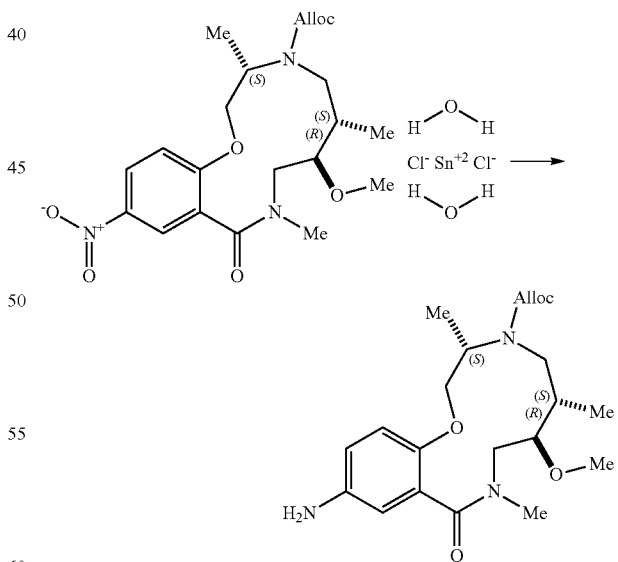

a. Nitro Reduction (2141-018b): To macrocycle (2141-017) (0.675 g, 1.550 mmol) dissolved in MeOH (Volume: 15.50 ml) was added tin(II) chloride dihydrate (3.50 g, 15.50 mmol). The reaction mixture was stirred at room temperature for 2 days or until LC/MS indicates complete conversion. The residue was dissolved in EtOAc and washed with 2 M aq. KOH (2×). The combined aqueous layers were washed with EtOAc (2×) and the resulting organic layers were washed with brine, dried over MgSO$_4$, filtered, and concentrated. The crude aniline (2141-018b) was used without purification. Note: The workup as described above produces a lot of precipitate/emulsion. This can be overcome by extensive washing or by quenching with 1 volume 1 M NaOH and filtration over celite prior to workup. (M+H)$^+$ calculated=406.24 (M+H)$^+$ measured (LC/MS)=405.98

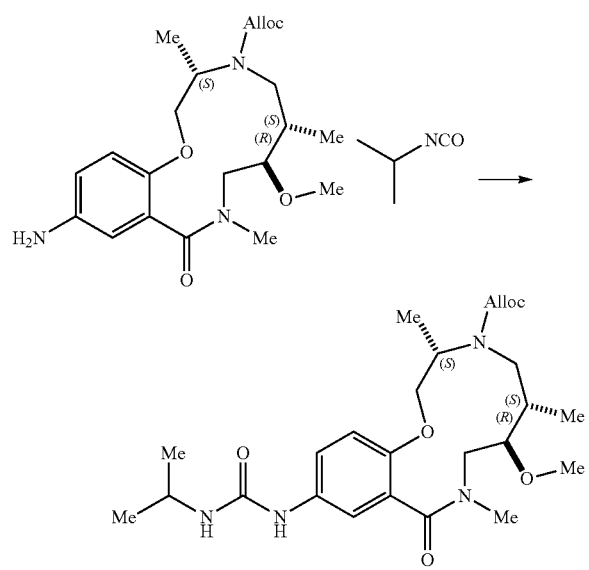

b. Acylation of the Aniline (2141-018): Isopropyl isocyanate (0.174 ml, 1.767 mmol) was added dropwise to a stirring solution of crude aniline (2141-018b) (0.597 g, 1.472 mmol) in CH$_2$Cl$_2$ (Volume: 7.36 ml) and reaction was stirred at rt overnight. LC/MS showed conversion into the desired product. The solvent was evaporated and the residue was purified via ISCO (0.5-9% MeOH in CH$_2$Cl$_2$, 18 min); Collected fractions 40-52 to afford the product as a white solid foam. 644 mg (89% over 2 steps) (M+H)$^+$ calculated=491.29 (M+H)$^+$ measured (LC/MS)=492.73 c. Alloc deprotection (2141-022): A 100 mL round-bottomed flask was charged with a solution of Urea (2141-018) (0.625 g, 1.274 mmol) in EtOH/CH$_2$Cl$_2$ (2:1). 1,3-Dimethylbarbituricacid (0.298 g, 1.911 mmol) was added in one portion at room temperature, followed by Tetrakis(triphenylphosphine)palladium(0) (0.147 g, 0.127 mmol). The mixture was stirred at 40° C. for ~16 h (overnight) or until LC/MS demonstrated conversion into a product with the same mass. The solvents were removed in vacuo, and the crude residue was dissolved in CH$_2$Cl$_2$ and passed through a plug of acidic resin (5 equiv relative to SM) rinsing with CH$_2$Cl$_2$ (~3 column volumes). The amine was then eluted with 1 M NH$_3$ in MeOH to afford sufficiently clean material from next step. (M+H)$^+$ calculated=407.27 (M+H)$^+$ measured (LC/MS)= 407.56 d. BRD-K13648511: Benzaldehyde (0.090 ml, 0.886 mmol) was added to a DMF (Volume: 2.95 ml) solution of crude amine (2141-022) (0.12 g, 0.295 mmol) at rt. Acetic acid (0.017 ml, 0.295 mmol) was added and the mixture was stirred for 30 min before sodium triacetoxyhydroborate (0.250 g, 1.181 mmol) was added. The resulting mixture was stirred at rt overnight. LCMS indicates complete SM consumption. Saturated aqueous sodium bicarbonate solution was slowly added until gas evolution ceased. The reaction mixture was diluted with EtOAc and the layers were separated. The organic layer was washed with brine, dried with MgSO$_4$, filtered, and concentrated. The residue was purified via ISCO (SiO$_2$, 1-12% MeOH in CH$_2$Cl$_2$, 20 min, 254 nm); Collected fractions 47-54 to afford the product as a white solid in 23% yield (34 mg) over 2 steps. (M+H)$^+$ calculated=497.3123, (M+H)$^+$ average (3 ESI replicates)= 497.3131±1.81 e. BRD-K17257309: 4-(pyridin-3-yl)benzaldehyde (151 mg, 0.827 mmol) was added to a DMF (Volume: 1378 µl, Density: 0.944 g/ml) solution of Crude amine (2141-022) (112 mg, 0.276 mmol) at rt. Acetic acid (15.77 µl, 0.276 mmol) was added and the mixture was stirred for 30 min before sodium triacetoxyhydroborate (234 mg, 1.102 mmol) was added and the mixture was stirred at rt overnight or until LC/MS indicates conversion into product. Saturated aq sodium bicarbonate solution was slowly added until gas evolution ceased. The reaction mixture was diluted with EtOAc and the layers were separated. The aqueous phase was extracted with EtOAc (3×). The combined organic layers were washed with brine, dried with MgSO$_4$, filtered, and concentrated. The residue was purified via ISCO (0.5-7% MeOH in CH$_2$Cl$_2$, 13 min) to afford the product as a yellow solid in 24% yield (38 mg) over 2 steps. (M+H)$^+$ calculated=574.3388 (M+H)$^+$ average (3 ESI replicates)= 5.74.3394±0.85 f. BRD-K98645985: 4-(Pyridin-2-yl)benzaldehyde (199 mg, 1.085 mmol) was added to a DMF (Volume: 1808 µl) solution of crude amine (2141-022) (147 mg, 0.362 mmol) at room temperature. Acetic acid (21.72 mg, 0.362 mmol) was added and the mixture was stirred for 30 min before NaBH(OAc)$_3$ (307 mg, 1.446 mmol) was added and the mixture was stirred at rt overnight. LC/MS indicated conversion into the desired product. Saturated aqueous sodium bicarbonate solution was slowly added until gas evolution ceased. The reaction mixture was diluted with EtOAc and the layers were separated. The aqueous phase was extracted with EtOAc (3×). The combined organic layers were washed with brine, dried with MgSO$_4$, filtered, and concentrated. The residue was purified via ISCO (0.5-7% MeOH in CH$_2$Cl$_2$, 13 min); Collected fractions 66-73 to afford the product as a brown solid in 26% yield (54 mg) over 2 steps. (M+H)$^+$ calculated=574.3388 (M+H)$^+$ average (3 ESI replicates)=5.74.3395±1.36.

g. Alloc Deprotection (2141-039a): A round-bottomed flask was charged with a solution of macrocycle (2141-017) (0.675 g, 1.550 mmol) in EtOH/CH$_2$Cl$_2$ (2:1). 1,3-Dimethylbarbituricacid (0.363 g, 2.325 mmol) was added in one portion at room temperature, followed by Pd(PPh3)4 (0.179 g, 0.155 mmol). The mixture was stirred under ambient conditions for ~16 h (overnight). The reaction was monitored by LC/MS and demonstrated complete starting material consumption and the presence of the desired mass. The reaction mixture was then passed over a silica plug eluting with 15% MeOH in CH$_2$Cl$_2$ (with 2% triethylamine). The filtrate was concentrated and used in the next step without purification (used theoretical yield). (M+H)$^+$ calculated=352.19 (M+H)$^+$ measured (LC/MS) 35

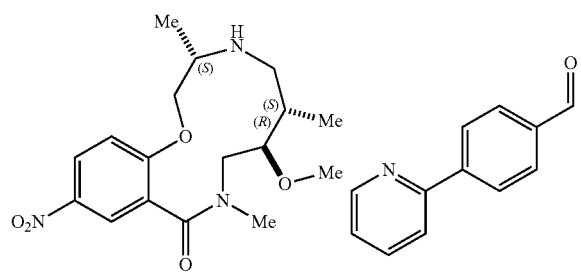

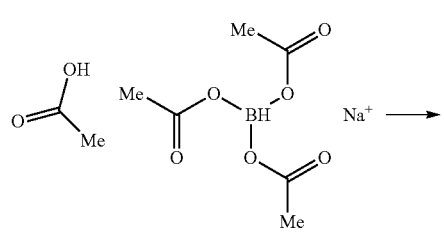

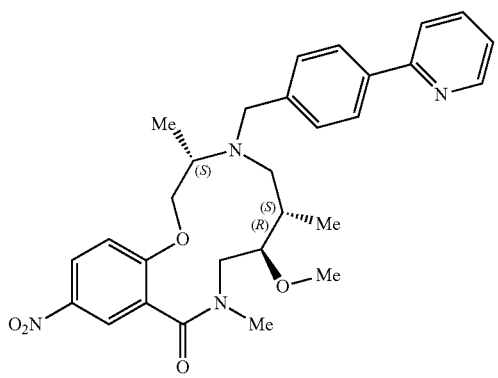

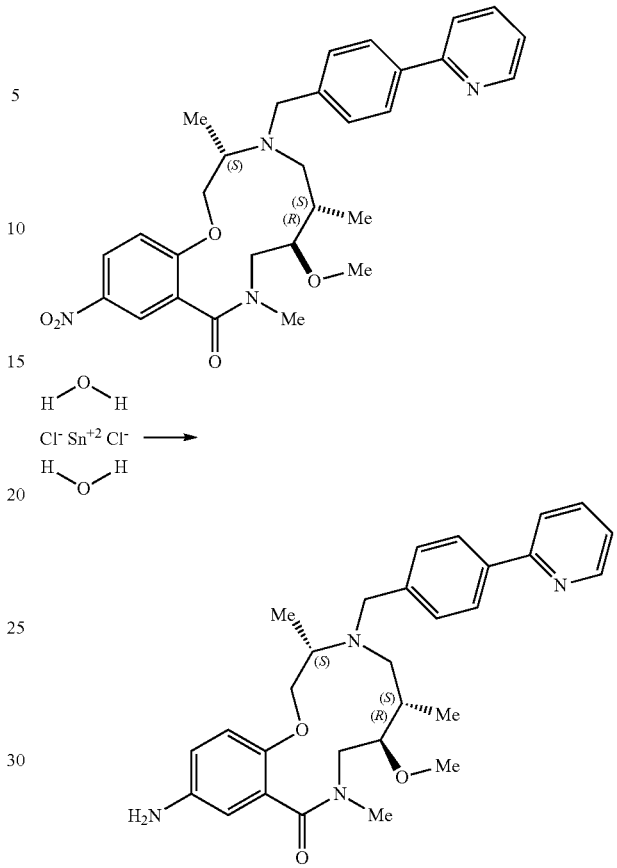

h. Reductive Amination (2141-039b): 4-(2-Pyridinyl)-benzaldehyde (852 mg, 4.65 mmol, 3 eq) was added to a DMF (Volume: 7755 µl) solution of crude amine (2141-039a) (545 mg, 1.551 mmol, 1 eq) at room temperature. Acetic acid (89 µl, 1.551 mmol, 1 eq) was added and the mixture was stirred for 30 min before sodium triacetoxyhydroborate (1315 mg, 6.20 mmol, 4 eq) was added. The mixture was stirred at room temperature for 2 days when LC/MS indicated complete conversion into product (presence of SM by LCMS). Saturated aqueous sodium bicarbonate solution was slowly added until gas evolution ceased. The reaction mixture was diluted with EtOAc and the layers were separated. The aqueous layer was extracted with EtOAc (3×). The organic layer was washed with brine, dried with MgSO$_4$, filtered, and concentrated. Material was taken forward without further purification attempts. $(M+H)^+$ calculated=519.29 $(M+H)^+$ measured (LC/MS)=518.91.

i. BRD-K25923209: To Macrocycle 2141-039b (0.804 g, 1.550 mmol) dissolved in MeOH (Volume: 15.50 ml) was added tin(II) chloride dihydrate (3.50 g, 15.50 mmol). The reaction mixture was stirred at 40° C. for 24 h until LC/MS indicated complete consumption of starting material (nitro) and presence of desired mass. Upon completion, the reaction mixture was concentrated and the resulting residue was dissolved in EtOAc and washed with 2 M aq. KOH (2×). The combined aqueous layers were washed with EtOAc (4×). The resulting organic layers were washed with brine, saturated aqueous NaHCO$_3$, water, and brine, dried over MgSO$_4$, filtered, and concentrated. The crude aniline was sufficiently pure to use in the capping step and therefore was used without purification. Note: The workup as described above produces a lot of precipitate/emulsion. This can be overcome by extensive washing or alternately, the reaction can be quenched with 1 volume of 1 M NaOH, stirred with celite for 10 minutes, and filtered prior to workup to yield 33.8% (17.2 mg) over 3 steps. $(M+H)^+$ calculated=489.286 $(M+H)^+$ average (3 ESI replicates)=489.2866±0.92.

j. BRD-K80443127: A screwtop vial was charged with aniline (BRD-K25923209) (43.3 mg, 0.089 mmol) and CH$_2$Cl$_2$ (Volume: 886 µl, Density: 1.325 g/ml). Isopropyl chloroformate (115 µl, 0.115 mmol) and DIEA (46.4 µl, 0.266 mmol) were added dropwise and reaction stirred under ambient conditions for 1 h. LC/MS showed complete sm consumption. The reaction mixture was loaded directly onto SiO$_2$ and purified via ISCO (1-12% MeOH in CH$_2$Cl$_2$, 20 min); Collected fractions 40-44 to afford the product as a yellow oil in 33.8% (17.2 mg) yield. $(M+H)^+$ calculated=575.3228 $(M+H)^+$ average (3 ESI replicates)= 575.3235±1.32.

k. BRD-K04244835: A 2.5 mL microwave vial was charged with aniline (BRD-K25923209) (40 mg, 0.082 mmol) and EtOH (Volume: 819 µl, Density: 0.81 g/ml). Squaramide (CRE-III-001) (20.75 mg, 0.098 mmol), DIEA (42.8 µl, 0.246 mmol), and DMAP (2.000 mg, 0.016 mmol) were added in sequence and the vial was sealed. The resulting solution was stirred at 85° C. overnight or until LC/MS indicated complete starting material consumption. The reaction mixture was loaded directly onto $SiO_2$ and purified via ISCO (1-12% MeOH in $CH_2Cl_2$, 20 min); fractions 50-56 were collected to afford the product as a yellow solid in 48.6% (26 mg) yield. $(M+H)^+$ calculated=654.365 $(M+H)^+$ average (3 ESI replicates)=654.3661±1.64.

9. Nuclear Isolation: Cells were trypsinized and washed 1× with PBS. Cells were suspended in Buffer A (25 mM HEPES pH 7.6, 5 mM $MgCl_2$, 25 mM KCl, 0.05 mM EDTA, 10% glycerol, 0.1% NP-40) and cell membranes were lysed by passing cells through a 22-gauge needle 10 times and incubation on ice for 5 minutes. Nuclei were pelleted by centrifugation at 400×g for 5 minutes.

10. Cell Lysis: Pellets of whole cells or isolated nuclei were lysed with lysis buffer (50 mM Tris-HCl pH 8.0, 300 mM NaCl, 0.1% NP-40, protease inhibitors) by rotating at 4° C. for 30 minutes. The lysate was cleared by centrifugation (20,000×g) for 5 minutes and transferred to a fresh tube.

11. ATPase Assay: Adapted from[85]. Each sample utilized 70 µg nuclear ESC lysates in 50 µL cell lysis buffer. The nuclear lysates were incubated with 1 µL anti-Brg1 antibody (ab110641) and 5 µL protein A dynabeads (Thermo) for 4 h and washed 1× with lysis buffer and 1× with wash buffer (10 mM Tris-HCl pH 7.5, 50 mM NaCl, 5 mM $MgCl_2$, protease inhibitor). After washing, 20 µL reaction buffer (10 mM Tris pH 7.5, 50 mM mM NaCl, 5 mM $MgCl_2$, 20% glycerol, 1 mg/ml BSA, 20 µM ATP, 20 nM plasmid DNA, 1 µCi gamma-$^{32}$P ATP, protease inhibitors, 1 µL DMSO or compound to 250 µM final concentration) was added to the beads. The reaction was incubated with shaking (900 rpm) at 37° C. After 30 minutes the reaction mixture (1 µL) was spotted on PEI cellulose TLC plates (Sorbtech) and the TLC was run in 0.5M LiCl, 1M formic acid. The plates were dried and developed using phosphoimager technology. The percent conversion from starting material to product was determined using Image J software and normalized to the no enzyme control.

12. Immunoblot Analysis: Total protein was denatured for 10 min at 95° C., separated on a 4-12% SDS-polyacrylamide gel, and transferred to a PVDF membrane (Immobilon FL, EMD Millipore, Billerica, MA). The membrane was blocked with 5% bovine serum albumin (VWR, Batavia, IL) in PBS containing 0.1% Tween-20 (PBST) for 30 mins at room temperature and then incubated in primary antibodies overnight at 4° C. The primary antibodies used were directed against ARID1A (Santa Cruz Biotechnology Inc., Dallas, TX; sc-32761), PBRM1 (Bethyl Laboratories, Montgomery, TX; A301-591A), BAF155 (Santa Cruz Biotechnology Inc., Dallas, TX; Sc-32763), BAF47 (Santa Cruz Biotechnology Inc., Dallas, TX; Sc-166165), LAMIN B1 (Santa Cruz Biotechnology Inc., Dallas, TX; Sc-377000). The primary antibodies were detected by incubating the membranes in goat-anti-rabbit or goat-anti-mouse secondary antibodies (LI-COR Biotechnology, Lincoln, NE) conjugated to IRDye 800CW or IRDye 680 respectively for 1 h at room temperature, and the signals were visualized using Odyssey C1x imager (LI-COR Biotechnology, Lincoln, NE).

13. Glycerol Gradients: 20 million mESCs were plates on gelatin coated 150 mm tissue culture plates and incubated for 24 h. Cells were treated with 30 µM BRD-K25923209 or DMSO for 24 h. Nuclear lysate from ~50 million cells (~0.6-1 mg nuclear protein) was layered on top of a 10-30% glycerol gradient (10 mL) in HEMG buffer (25 mM Hepes 7.6, 0.1 mM EDTA, 12.5 mM $MgCl_2$, 100 mM KCl). The protein was separated by the gradients through ultracentrifugation in Beckman rotor SW41 at 40,000 RPM for 16 h. Twenty 500 µL fractions were removed sequentially from the top of the gradients and 50 µL of each fraction was used for immunoblot analysis.

14. Sequential Salt Extractions: Sequential salt extractions were performed as published[80], with the following modifications: mESCs were treated for 2 h with 30 µM BRD-K25923209 or DMSO. Nuclei were isolated into two tubes (5 million each) and the salt extractions were performed with 30 µM of BRD-K25923209 or DMSO in each salt wash.

15. Biotin Pull Downs: Compound 2-57 (200 µM in 200 µL PBS) was pre-bound to 20 µL high capacity streptavidin beads (Solulink) for 30 minutes. The beads were washed 1× with lysis buffer and incubated with cell lysates preincubated with DMSO or 200 µM of BRD-K25923209 for 2 h. The beads were washed once with 1 mL lysis buffer and boiled in SDS loading buffer for immunoblot analysis.

16. CETSA protocol: CETSA was performed as published[86] with the following modifications: mESCs were treated with 50 µM of compound BRD-K25923209 or DMSO for 1 hour. The cells were trypsinized, washed 1× with PBS and 2 million cells of each condition were resuspended in 1 mL PBS. Cells (100 µL) were transferred into eight wells of a strip tube and put in a temperature gradient PCR block for 3 minutes, followed by incubation at room temperature for 3 minutes. The cells were lysed with 2× freeze-thaw cycles on a 25° C. heat block and the cell lysis was transferred to microcentrifuge tubes and centrifuged at 15,000×g for 20 minutes at 4° C. The soluble protein (90 µL) was removed from pellets and added to SDS loading buffer for immunoblot analysis.

17. RNA-Seq ECS with BAFi: Mouse ESE14 cells were plated at a density of 2.5×10$^5$ in a gelatin coated 6-well plate and in a 37° C., 5% $CO_2$ incubator for 24 h. RNA was purified from ESCs treated with BAF inhibitor BRD-K98645985 or a DMSO mock treatment for 16 h. RNA was extracted using TRIzol reagent (Life Technologies Corporation, Grand Island, NY) according to the manufacturer's instructions and cleaned up using RNeasy Mini Kit (Qiagen Inc., Valencia, CA). RNA libraries were prepared for sequencing using standard Illumina protocols. Sequencing was performed using an Illumina HiSeq 2500. Reads were 100 bp and paired-ended. Reads were trimmed using Trimmomatic and aligned to the mm10 reference genome using STAR. Gene expression levels were computed using htseq-count using default parameters. Differential expression analysis was performed with DESeq2 using default parameters[87]. Processed and unprocessed data is deposited in GEO GSE113627.

18. RNA-Seq Arid1a f/f ESCs: Arid1a$^{f/f}$ mice were a kind gift from Terry Magnuson (UNC School of Medicine)[88]. Arid1a$^{f/f}$ mice were bred to Actin:CreERT2 mice to obtain Arid1a$^{f/+}$; ActinCreERT2, which were subsequently interbred with Arid1a$^{f/f}$ mice. Timed matings were set up between Arid1a$^{f/f}$; ActinCreERT2 and Arid1a$^{f/f}$ and oviducts were flushed at day 3.5. ESCs were derived as described[89]. Arid1af/f:CreERT2 ESCs were treated with either ethanol or 1 µM 4-hydroxytamoxifen for 24 hours then passaged. RNA was collected 72 hours after treatment. RNA was isolated using Quick-RNA Miniprep Kit (Zymo Research). RNA-Seq libraries were prepared using either Illumina TruSeq RNA Library Prep Kit v2 or Illumina TruSeq Stranded mRNA Kit following the manufacturer's instructions. Sequencing was performed using an Illumina HiSeq 2500. Reads were 50 bp and single-ended. Fastq files were evaluated for quality using FastQC and trimmed using Trimmomatic. Trimmed sequences were mapped to the mm10 reference genome using HISAT2 in single-end mode with default parameters. The average counts per million (cpm) was calculated for each sample condition using custom R scripts, and differentially expressed genes were identified using the edgeR package in Bioconductor 90. A false discovery threshold of 0.05 was imposed using the toptags function of edgeR. Processed and unprocessed data is deposited in GEO GSE113872

19. Cell line models of HIV-1 latency: J-Lat A2 (LTR-Tat-IRES-GFP Cells)[91] and J-Lat 11.1 (integrated full-length HIV-1 genome mutated in env gene and harboring GFP in place of Nef)[92]) cells were cultured in RPMI-1640 medium (Sigma Aldrich) supplemented with 10% FBS and 100 μg/ml penicillin-streptomycin at 37° C. in a humidified 95% air-5% $CO_2$ atmosphere. Cells were treated with compounds or DMSO for 48 h, followed by quantitation of GFP positive cells using flow cytometry. Data was normalized as a fold increase over DMSO treated control. Data are presented as mean of at least 3 independent experiments ±SD.

20. Ex Vivo HIV latency model (Lassen)[61]: Viral pseudotyped particles were obtained by co-transfecting HXB2 Env together with the HIV-1 backbone plasmid (pNL4.3.Luc.R-E-) into HEK 293 T cells using PEI (Polyethylenimine) transfection reagent. At 48 h and 72 h post-transfection, the pseudovirus-containing supernatant was collected, filtered through a 0.45 μm filter, aliquoted, and stored at −80° C. Primary CD4+ T cells were isolated from buffy coats from healthy donors by Ficoll gradient followed by density-based negative selection of CD4+ T cells with RosetteSep kit (StemCells Technologies). Twenty-four hours after isolation, cells were spin-infected as described, with minor modifications[55,61]. CD4+ T cells were spin-infected at 1200 g for 2 h with the HBX2 Env pseudotyped pNL4.3-Luc virus. Eighteen hours after spin-infection cells were washed and cultured in growth media supplemented with 5 μM saquinavir mesylate. After three days, latently infected cells were treated with BAFi's or left untreated for 24 h in the presence of 30 μM raltegravir, followed by luciferase assay (Promega). Data was normalized as a fold increase over untreated control. Synergy was calculated using Bliss score formula[93]: Sexp=[1−(1−A)×(1−B)], where Sexp. is the expected percentage of cells reactivated after combinatorial treatment in absence of synergism and A and B correspond to the percentage of cells reactivated by the single treatments. Combination was considered synergistic if the observed effect of combined treatments was significantly higher than calculated value (Sexp.), and is indicated with an S in the figure.

21. Ex Vivo HIV latency model (Bosque-Planelles)[62]: Primary CD4+ T cells were isolated from buffy coats from healthy donors by Ficoll gradient followed by density-based negative selection of CD4+ T cells with RosetteSep kit (StemCells Technologies). Twenty four hours after isolation primary CD4+ T cells were cultured in the presence of 10 ng/ml TGF-β (Sigma-Aldrich), 1 μg/ml α-IL-4 (PeproTech) and αCD3/CD28 dynabeads (Life Technologies) at the cell:bead ratio 1:1 for 3 days. αCD3/CD28 dynabeads were removed, cells washed and cultured for 4 days in growth media supplemented with 30 IU/ml rIL-2 (Roche) Then cells were washed and subjected to spininfection (90 min, 1200 g) and incubated over-night. Next day cells were washed and re-suspended in growth media supplemented with 30 IU/ml rIL-2 and Saquinavir Mesylate (5 μM). Seven days post-infection cells were treated with BRD-K80443127 in increasing concentrations or with PMA/Ionomycin in the presence of Raltegravir (30 μM). After 24 hours of stimulation cells were collected and subjected to the luciferase assay, RLU was normalized to the total protein content.

22. Biomarkers: CD4+ T cells were isolated from three healthy donors and treated in duplicate with 3 μM BRD-K80443127 or control DMSO for 16 hours. Cells were lysed with TRIreagent (Sigma) and total RNA was isolated with Total RNA Zol-Out (A&A Biotechnology) kit and cDNA was synthetized using random primers and Superscript II Reverse Transcriptase (Life Technologies). Real-time PCR was performed using GoTaq qPCR Master Mix (Promega) on CFX Connect Real-Time PCR Detection System thermocycler (BioRad) using following conditions: 95° C. for 3 min, followed by 40 cycles of 95° C. for 10 sec and 60° C. for 30 sec. Products quality was assessed by theirs melting curve analysis. Relative expression of target genes was normalized to β-2-microglobulin and calculated using Livak-Schmittgen method[84].

```
Primers: (p21: For-AGCAGAGGAAGACCATGTGGAC (SEQ ID NO: 09), Rev-TTTCGACCCTGAGAGTCTCCAG (SEQ ID NO: 10). (cMYC: For-AAGCCACAGCATACATC C (SEQ ID NO: 11), Rev-GCACAAGAGTTCCGTACTC (SEQ ID NO: 12). B2M: For-AGCGTACTCCAAAGATTCA GGTT (SEQ ID NO: 13), Rev-ATGATGCTGCTTACATGTC

TCGAT (SEQ ID NO: 14))
```

23. HIV latency reversal from patient samples: All patients were older than 18 years, c-ART treated for at least 3 years, and their viral loads were below 50 copies/ml for more than 12 months with no blips in the past two years. CD4+ T cells from aviremic HIV+ patients were isolated as described previously[55] with minor modifications. Briefly, frozen PBMCs were cultured in RPMI medium over-night to recover. Then next day CD4+ T cells were isolated twice (enriched CD4+ T cells were subjected to a second round of CD4+ T cell enrichment) and left for 6 hrs to recover. Three million cells were treated with DMSO, 10 μM BRD-K80443127, 200 nM Prostratin, 10 μM BRD-K80443127 and 200 nM prostratin, and αCD3/CD28 magnetic beads (at cell:bead ration 1:1) as a positive control in triplicate. After 24 hours cells were lysed in TRIreagent (Sigma), total RNA was isolated with Total RNA Zol-Out (A&A Biotechnology) kit and cDNA was synthetized using random primers and Superscript II Reverse Transcriptase (Life Technologies). Detection of cellular associated pol RNA was performed as described previously (Pol: For GGTTTATTA-CAGGGACAGCAGAGA (SEQ ID NO:15), Rev-ACCTGCCATCTGTTTTCCATA (SEQ ID NO: 16))[55]. This study was conducted in accordance with the ethical principles of the Declaration of Helsinki. HIV-1 infected patient volunteers were informed and provided signed consent to participate in the study. The study protocol was approved by The Netherlands Medical Ethics Committee (MEC-2012-583). cDNA generated from control and 10 μM BRD-K80443127 treated samples was used to assess expression of BAF target genes biomarker genes-p21 and C-MYC.

```
Primers: (p21: For-AGCAGAGGAAGACCATGTGGAC
(SEQ ID NO: 17), Rev-TTTCGACCCTGAGAGTCTCCAG
(SEQ ID NO: 18). cMYC: For-AAGCCACAGCATACATCC
(SEQ ID NO: 19), Rev-GCACAAGAGTTCCGTAGC (SEQ
ID NO: 20). B2M: For-AGCGTACTCCAAAGATTCAGGTT
(SEQ ID NO: 21), Rev-ATGATGCTGCTTACATGTCTCGAT
(SEQ ID NO: 22))
```

24. Activation markers, apoptosis and viability of primary CD4+ T cells: Activation markers, namely CD25 and CD69 were analyzed as described previously[55]. Briefly, CD4+ T cells were treated with DMSO, compound, or PMA/Ionomycin for 24 and 72 hours. Cells were collected, washed with PBS and stained for 30 min at 4° C. with α-CD25-APC (17-0259-42, eBioscience) and α-CD69-FITC (11-0699-42, eBioscience). Following two washes with PBS, cells were fixed with 1% HCHO at 4° C. and analyzed by flow cytometry with Becton Dickinson Fortessa instrument. To determine percent of apoptotic cells after treatment cells were stimulated for 24 and 72 hours and stained with anti-AnnexinV-PE (BD Biosciences, cat. 556454) in the presence of 2.5 mM $CaCl_2$ for 20 min at 4° C. Cells were analyzed by Becton Dickinson Fortessa flow cytometer. Data represents the average of six experiments performed on cells from different healthy donors. Viability of ex-vivo infected primary CD4+ cells was determined by flow cytometry on the basis of forward versus side scatter analysis.

25. FAIRE: FAIRE experiment was performed as described, with minor modifications[55]. Eighteen hours prior to analysis, J-Lat 11.1 cells were treated with BAFi's where indicated. Cells were fixed for 10 min by adding formaldehyde to a final concentration of 1% at room temperature. Twenty million cells were used per FAIRE experiment. The reaction was quenched with 125 mM glycine. Cross-linked cells were washed with PBS followed by washes with buffer B and buffer C. For sonication, cells were re-suspended in ChIP incubation buffer and chromatin was sheared by sonication to an apparent length of ~200-400 bp (corresponding to ~100-200 bp of free DNA) using a BioRuptor sonicator (Cosmo Bio Co., Ltd) with 20 times 60-s pulses at maximum setting at 4° C. Sonicated chromatin was once phenol:chloroform:isoamyl alcohol (24:24:1) extracted, washed with chloroform:isoamylalcohol (24:1) and ethanol precipitated. Isolated DNA was subjected to Sybergreen qPCR cycles with specific primers

```
(Nuc-0: For-ATCTACCACACACAAGGCTAC (SEQ ID NO:
23), rev-GTACTAACTTGAAGCACCATCC (SEQ ID NO:
24); HSS: for-AAGTTTGACAGCCTCCTAGC (SEQ ID
NO: 25), rev-CACACCTCCCTGGAAAGTC (SEQ ID NO:
26); Nuc-1: for-TTTGCCTGTACTGGGTCTCTCTGG
(SEQ ID NO: 27), rev-CACAACAGACGGGCACACACT
(SEQ ID NO: 28))
```

CACAACAGACGGGCACACACT (SEQ ID NO:28)) with a CFX Connect Real-Time PCR Detection System (BioRad) and GoTaq qPCR Mastermix (Promega).

C. Quantification and Statistical Analysis

Statistical details can be found in the Figure legends. Bar graphs are plotted as mean±S.D. Statistical significance was calculated using Prism 7. Asterisks indicate the level of significance using student's T test (* $p<0.05$  $p<0.01$, * $p<0.001$, **** $p<0.0001$).

D. Data and Software Availability

RNA-Seq datasets are deposited in GEO with accession number GSE113872 for Arid1af/f:CreERT2 ESCs ESCs and GSE113627 for BRD-K98645985 treated ESCs.

E. Additional Resources

A full description of the high throughput screen and associated bioassays can be found on PubChem under assay number 602436.

III. RESULTS

A. Development and Confirmation of a Luciferase Reporter Cell Line

Figure 1:
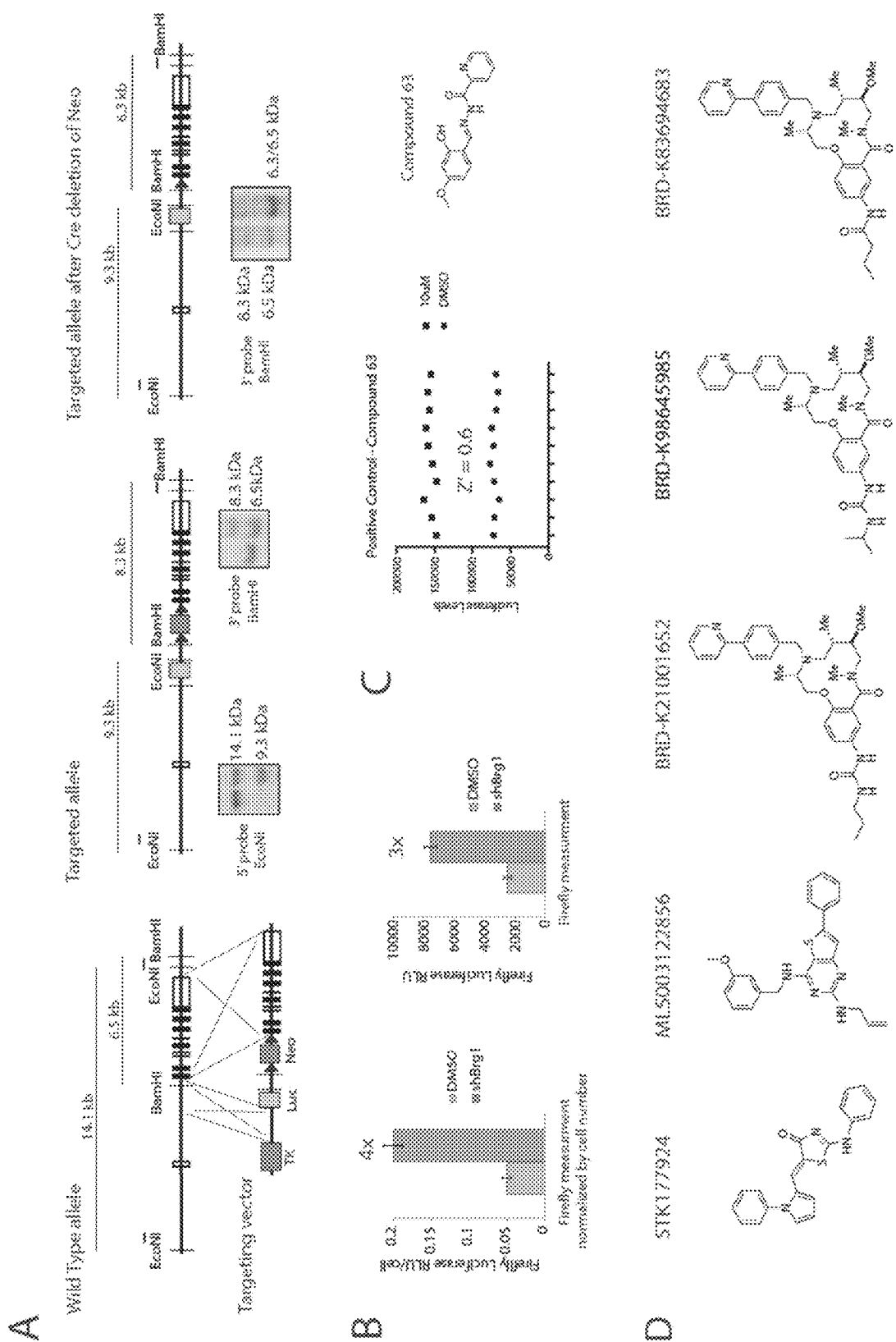
FIG. 1: High throughput screen for inhibitors of BAF-mediated transcriptional repression. A. The generation of a knock-in reporter cell line at the Bmi1 locus using homologous recombination in mouse embryonic stem cells and validation using Southern blot analysis. B. Validation of the Bmi1-luciferase reporter cell line using lentiviral-mediated knockdown of Brg1 either with (above) or without (below) normalizing by cell number. C. The robustness of the screen was determined using positive control compound 63. D. The five hits identified from high throughput screening efforts.

In murine ESCs the BAF complex is essential for maintaining repression of certain polycomb repressive complex 1 subunit genes including Bmi1 and Ring1a while activating genes involved in maintaining the pluripotent state, such as Fgf4[54,56]. For high throughput screening of BAF inhibitors, we developed a knock-in luciferase reporter of BAF transcriptional repression. We used homologous recombination to construct a mESC line with firefly luciferase inserted at exon 1 of Bmi1. We used Southern blotting to confirm successful recombination of the original targeting vector, as well as subsequent Cre-mediated excision of the Neo selection marker (FIG. 1A). To confirm that the reporter line was a reliable indicator of esBAF-mediated repression of Bmi1, we knocked down the gene encoding the BAF ATPase BRG1 using lentiviral shRNA. Three days after infection, a stable four-fold increase in luciferase levels was observed when corrected for cell number, indicating successful de-repression of Bmi1 (FIG. 1B). In an effort to simplify the requirements for high throughput screening, we performed the Brg1 knockdown without correcting for cell number and found that the reporter line still displays robust three-fold induction of luciferase 72 hours after infection with shBrg1-expressing lentivirus (FIG. 1B).

B. High throughput Assay Development: The knock-in ESC line was generated on mouse embryonic fibroblasts (MEFs) as a feeder layer. Since a feeder layer is not compatible with high throughput screening, we made the cell line feeder free by passaging at high density five times on gelatin. While we previously developed methods to gelatin coat 384-well plates[54], this was not feasible for this scale of screening effort. Instead we identified the Corning High Bind® surface to support normal ESC morphology and normal alkaline phosphatase levels (indicative of maintained pluripotency) compared to gelatin coated plates (FIG. S1A Marian et al., Ibid.). The assay was optimized in 384-well format at the Broad Institute Probe Development Center (BIPDEC). The coefficient of variance (CV) for firefly luciferase reading across a 384-well plate was 4.5% and using a non-specific hit identified in the pilot qRT-PCR screen (compound 63) as our positive control[54], we calculated a Z-factor of 0.6, indicating a robust screen (FIG. 1C).

C. High Throughput Screen: We screened 347,670 compounds in duplicate (FIG. S1B for illustration of reproducibility, Marian et al., Ibid.). The compounds included the MLPCN validation set of natural products, known bioactives, commercially available compound libraries, and compound libraries designed by scientists at the Broad Institute (PubChem assay entry 602393 for full description of library). We defined hits as compounds with luciferase inductions that were at least 3 standard deviations above the mean, which corresponded to approximately 40% of the maximal activity observed with Brg1 knockdown. We identified 7048 hits (hit rate of 2%), which is high, but not unexpected from cell-based luciferase assays that tend to identify nonspecific luciferase stabilizers[57]. Hits identified in >5 luciferase screens or >10% of luciferase screens on PubMed were eliminated, as were compounds containing functional groups with known reactivity, including α-chloroketones, imines, and nitro groups. This resulted in a refined hit list of 1157 compounds for a hit rate of 0.33%, more in line with the expected hit rate for a robust screen (see FIG. S1C for summary of the screening tree, Marian et al., Ibid.). We rescreened the 1157 compounds at eight doses in the cell-based luciferase assay as a confirmatory assay along with a counter-screen for viability. We confirmed 548 hits with $EC_{50}$<10 µM and toxicity $EC_{50}$>30 µM. We then treated cells with these hits at a single dose (30 µM) in the qRT-PCR screen previously reported 54. From this secondary assay, we found only five compounds that increase Bmi1 at least six-fold, Ring1 at least two-fold and decreased Fgf4 at least five-fold (FIG. 1D). STK177924, a known nonspecific pan-assay interference (PAINS) scaffold, was eliminated (FIG. 1D)[58]. We next used chemoinformatics to investigate the SAR of the thiophene (MLS003122856) from the primary screen and developed a small library of analogs to explore additional SAR for linker attachment (FIG. S1D Marian et al., Ibid.). The biotin-linked compound on solid support failed to enrich subunits of the BAF complex from lysates (FIG. S1E Marian et al., Ibid.), and in addition, this compound had only moderate HIV latency reversal activity (FIG. S1F Marian et al., Ibid.). Therefore, while the thiophene may have interesting biological activity worth investigating, there is substantial evidence that it doesn't directly target the BAF complex or phenocopy the effects of BAF deletion in latent HIV-1 infected T cells.

Figure 2:
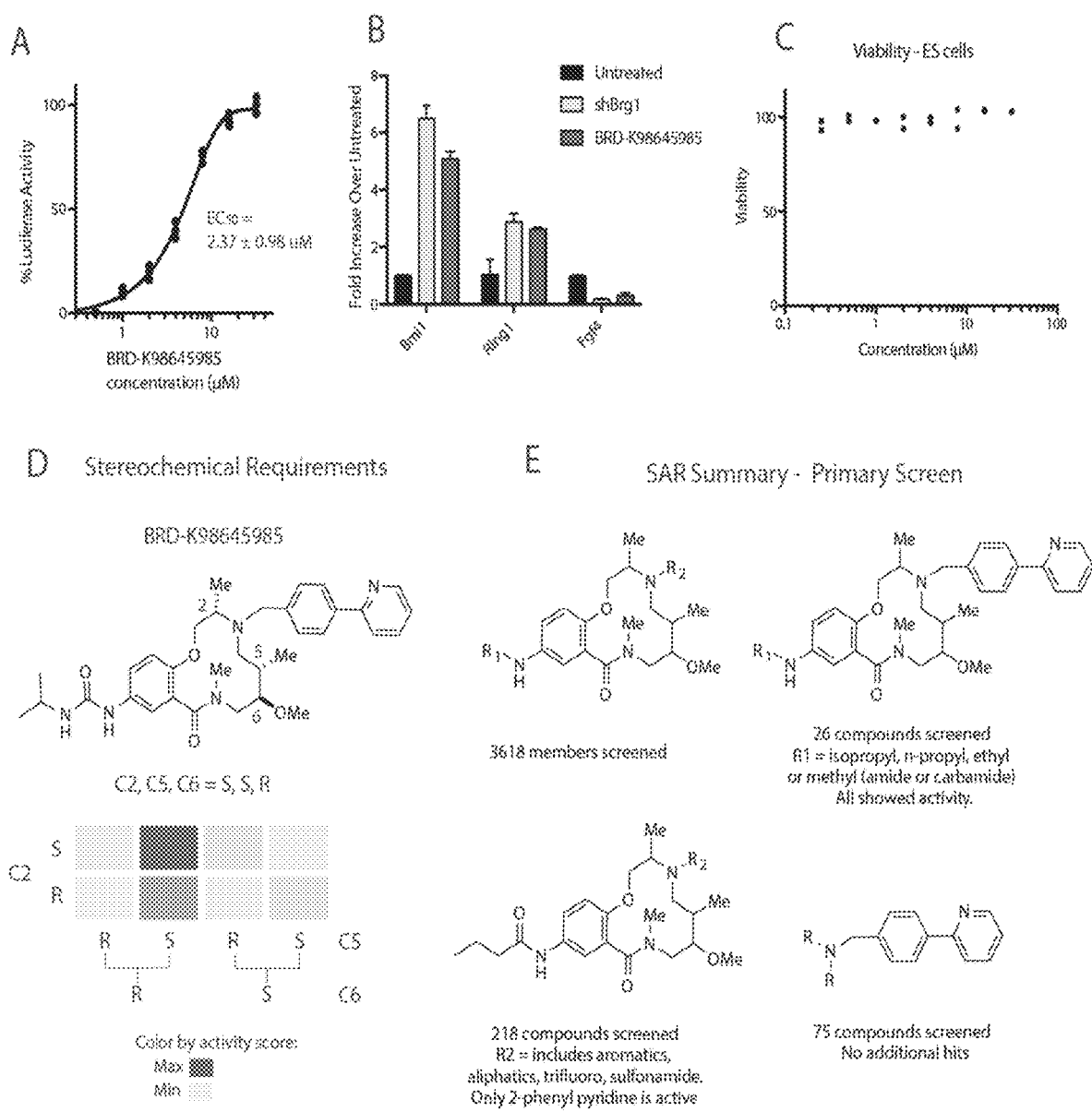
FIG. 2: 12-membered macrolactams are inhibitors of BAF-mediated transcription. A. The $EC_{50}$ was measured for the best screen hit BRD-K98645985 after 24 h compound treatment with the Bmi1-luciferase reporter cell line. Each concentration was dosed in triplicate. B. The fold change of the transcription of three BAF target genes was calculated using qRT-PCR after 18 h BRD-K98645985 treatment (30 µM) or Brg1 knockdown compared to untreated cells. C. Viability measurements in wild type ESCs were performed after 72 h of compound or DMSO treatment using CellTiter-Glo®. D. The structure activity relationship of the eight stereoisomers of BRD-K98645985 based on initial luciferase induction from the primary screen. E. The structure activity relationship of the 3618 macrolactam library members based on initial luciferase induction from the primary screen.

D. Broad DOS Library Macrocycle SAR:

The three remaining hits shared a very similar macrocyclic scaffold with only slight variations of substituents off macrocycle aniline: n-propyl amide (BRD-K83694683), n-propyl urea (BRD-K21001652) and isopropyl urea (BRD-K98645985). Re-evaluation of hit BRD-K98645985 in the luciferase assay provided an $EC_{50}$ of approximately 2.37±0.98 µM (FIG. 2A). In addition, we observed a 5-fold increase in Bmi1, 2.6-fold increase in Ring1, and 3.3-fold decrease in Fgf4 upon treatment with 30 µM of compound, a profile that closely mimics Brg1 KO (FIG. 2B). We observe no toxicity to ESCs up to 30 µM (FIG. 2C), or to HepG2, HEK293T and A549 cells (FIG. S2A Marian et al., Ibid.), increasing enthusiasm for this scaffold. The three hits containing this scaffold are members of the DOS library synthesized using head-to-tail scaffold design[59]. The primary screen contained 3618 compounds containing the same 12-membered macrolactam scaffold. Substituents off the scaffold vary at two positions ($R_1$ off the core aniline and $R_2$ off the core secondary amine) and the stereochemistry varies at three positions along the ring, C2, C5, and C6. While all stereoisomers with varying stereochemistry at C2, C5, and C6 were included for BRD-K98645985, BRD-K83694683 and BRD-K21001652, all of the top hits have the same stereochemical configuration. Taking a closer look at the primary screen scores for the eight stereoisomers of BRD-K98645985 the stereoisomer S,S,R showed significantly increased activity over the other stereoisomers, supporting a specific target (FIG. 2D). A similar profile was observed for BRD-K83694683 and BRD-K21001652 (FIG. S2B Marian et al., Ibid.). To further define the SAR from initial screen data we also looked at varied substituents at two positions, $R_1$ and $R_2$ (FIG. 2E). The most common building block used at $R_1$ was n-propyl amide, which was included in 218 macrolactam library members. For these 218 library members $R_2$ groups included aliphatic groups, aromatic groups, and sulfonamides, but only compounds with 2-phenyl pyridine moiety at $R_2$ were hits in the primary screen. To ensure that the preference for 2-phenyl pyridine isn't due to nonspecific interactions, we also looked at the 75 compounds in the initial compound library that contained the 2-phenyl pyridine moiety and confirmed that only the DOS macrolactams were hits. Substituting phenyl for 2-phenyl pyridine at $R_2$ increased the cLogP from 3.5 to 4.2, which in conjunction with a lowered efflux ratio, could indicate that the increased activity is due to improved cell permeability[60]. There were 26 compounds that contained the 2-phenyl pyridine at position $R_2$ and varying substituents at $R_1$ and all were hits to some degree in the primary screen. This likely indicates that the $R_1$ position is more permissible to variation than the $R_2$ position; however, the variations at $R_1$ in the screen were minimal, including only simple aliphatic groups connected via amides, ureas and carbamates.

Figure 3:
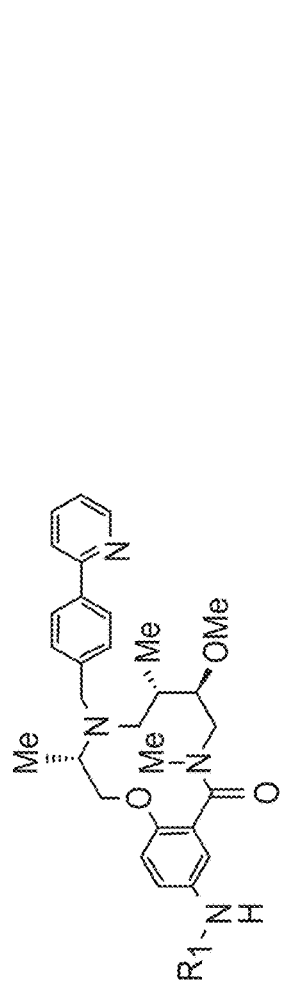
FIG. 3: The structure activity relationship between members of a solution phase 12-membered macrolactam analog library: A solution phase library of 30 analogs was synthesized and tested to further explore structure activity relationship for compounds with variations at A. the aniline ($R_1$), and B. the secondary amine ($R_2$). Activity was defined as the $EC_{50}$ in the luciferase reporter screen and as the fold transcriptional change of three BAF targets (Bmi1, Ring1, Fgf4) at a single compound concentration (30 µM) determined using qRT-PCR. n=3. Data presented as mean±S.D. NA=no activity.

E. Solution Phase Macrolactam Library:

Based on this initial SAR data, we synthesized a small focused 30-membered library to further investigate substitutions at the $R_1$ and $R_2$ positions (FIG. 3). For this library, we developed a solution phase synthesis based on the previously published solid phase synthesis of the scaffold with minor alterations (FIG. S3 Marian et al., Ibid.)[59]. For the 30 library members, we performed the luciferase screen in dose and also calculated the fold change in Bmi-1, Fgf4, and Ring1 at a single dose (30 µM) using qRT-PCR (FIG. 3, FIG. S3 Marian et al., Ibid.). We found good correlation between activity in the two assay formats. We varied many substituents at the $R_1$ position and confirmed that small aliphatic substituents linked via amide, urea and carbamates are tolerated (FIG. 3A). Interestingly, a small aromatic ring is tolerated at $R_1$, while a squarate linkage is not. Importantly, it is revealed that the free aniline is almost as equally potent as the parent compound and that no substituent is actually required at the $R_1$ position. At the $R_2$ position, 2-benzyl pyridine is still the best substituent, although 3-benzyl pyridine and 4-benzyl pyridine are tolerated (FIG. 3B). Not surprisingly, smaller substituents containing a single aromatic ring are not active, but interestingly, the closely related 2-benzyoyl pyridine and amide phenyl pyridine are also not active, indicating that the benzyl pyridine may be involved in a specific binding mechanism after all, and not simply functioning to increase cell permeability.

The last thing we looked at is the position of the $R_2$ substituent off the macrocycle aromatic. We found no tolerance for moving the phenyl pyridine from the para to the meta position (FIG. S3D). We measured solubility and neither this value nor the cLogP values for library membered strongly correlated with activity (Table S1 Marian et al., Ibid.). Additionally, the compounds displayed low toxicity towards cell lines although a few showed slight toxicity, possibly correlated to low solubility (Table S1 Marian et al., Ibid.).

F. Latency Reversal:

Using a primary cell model of HIV-1 latency established in ex vivo infected human CD4+ T cells[61], we measured HIV-1 reversal activity of six compounds from the follow up library: three with high activity in the Bmi1 luciferase reporter assays (BRD-K98645985, BRD-K25923209, BRD-K80443127), one with moderate activity (BRD-K17257309), and two with low/no activity (BRD- K13648511, BRD-K04244835). We found remarkable correlation between the ability to induce Bmi1 transcription in ESCs and the ability to increase transcription of latent HIV-1 in a concentration dependent manner (FIG. 4A). The activation was confirmed in a second ex vivo model of HIV latency (FIG. S4A Marian et al., Ibid.)[62] and the differential expression of two BAF target genes, namely c-MYC and p21, upon treatment with BRD-K80443127 was consistent with BAF inhibition (FIG. 4B)[63-66]. The compounds show excellent activity even in the low concentration range of 1-10 µM, and importantly, the compounds show no toxicity to T cells at these concentrations (FIG. 4C, FIG. S4B Marian et al., Ibid.). Unwanted general immune activation may be a side effect of treatments with some LRAs, which reduces their clinical applicability 67.68. To investigate whether inhibitor treatment results in stimulation of T cells, we treated human primary CD4+ T cells isolated from two healthy donors with BRD-K80443127 for 24 and 72 hours, followed by detection of activation markers CD25 and CD69. As expected, PMA/Ionomycin treatment resulted in activation of T cells while BRD-K80443127 treatment had no effect on CD25 and CD69 expression (FIG. S4C Marian et al., Ibid.). We also found that the compounds can be used in conjunction with other HIV latency reversal agents, such as HDAC inhibitors SAHA, VPA and romidepsin or PKC modulators prostratin and bryostatin to boost activity compared to single agent treatments (FIG. 4D) and the activities were primarily additive, with slight synergy when compared across multiple drug concentrations (FIG. S4D Marian et al., Ibid.)[69]. To confirm whether inhibitors could reverse HIV-1 latency in T-cells obtained from HIV-1 infected patients, we treated CD4+ T cells from three aviremic patients with BRD-K80443127, prostratin, BRD-K80443127 and prostratin, and αCD3/CD28 magnetic beads as a positive control (FIG. 4E). Patient 1 CD4 T cells responded to all treatments, while interestingly, double treatment with BRD-K80443127 and prostratin resulted in 63% latency reversal observed after treatment with the positive control αCD3/αCD28 (FIG. 4E). Cells from patient 2 and 3 did not result in a significant increase in cell associated HIV-1 POL after treatment with BRD-K80443127 alone; however, when co-treated with the PKC agonist prostratin, BRD-K80443127 showed significant increase in POL copies (FIG. 4E). As biomarkers can be clinically useful as surrogate measures of compound activity, we examined expression levels of BAF target genes p21 and C-MYC in the three patients and we observed significant decrease of p21 and C-MYC transcripts levels, confirming BRDK80443127 activity in these cells.

Figure 5:
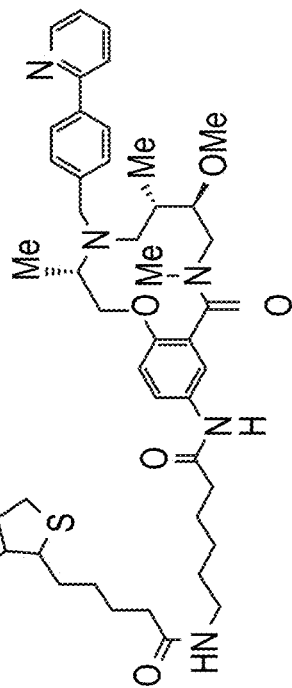
FIG. 5: 12-membered Macrolactams are inhibitors of ARID1A-containing BAF complexes. A. Differential gene expression of mESCs treated with 30 µM of BRD-K98645985 for 18 h was compared to published differential gene expression in Brg1 KO mESCs[70] to determine overlapping gene sets. Data was acquired from RNA-Seq analyses. B. The luciferase induction upon treatment with macrolactams with propyl amide (BRD-K83694683), butyl amide (CAM2-64) and biotin-hexylamide (CAM2-56) appended off the aniline was determined using the BMI1-luciferase reporter cell line. C. Pulldowns were performed from ESC lysates pretreated with DMSO or 200 µM BRD-K25923209 using biotin or CAM2-56 prebound to streptavidin resin. Protein enrichment was determined using immunoblot analysis. D. Protein stabilization by BRD-K25923209 was determined using CETSA in mESCs. The stabilization of ARID1A, PBRM1 and LAMINB1 was detected using immunoblot analysis of soluble proteins after incubation in a temperature gradient. E. Sequential salt extractions were performed on ESC nuclei. The chromatin was washed with increasing concentrations of salt containing DMSO or BRD-K98645985 (30 µM) and the elution of ARID1A and PBRM1 were analyzed using immunoblot analysis. The percent of protein elution was calculated across all five washes using ImageJ for ARID1A and PBRM1. Data are presented as mean±S.D. Asterisks indicate the level of significance compared to untreated cells using student's T test (* $p<0.05$  $p<0.01$, * $p<0.001$, **** $p<0.0001$). F. J-Lat 11.1 cells were treated with increasing concentrations of BRD-K80443127 and reactivation was quantitated at 48 h post treatment. Percent GFP positive cells (left axis, green bars), which corresponds to the level of HIV-1 activation, and cell viability (right axis, transparent bars) were both evaluated by flow cytometry. G. Levels of nucleosome occupancy at the HIV-1 5'-LTR region following treatment with BRD-K80443127, CAPE, and PMA were analyzed using FAIRE assay. Data are presented as mean±S.D. Asterisks indicate the level significance compared to untreated cells using student's T test (* $p<0.05$  $p<0.01$, * $p<0.001$, **** $p<0.0001$).
Figure 5:
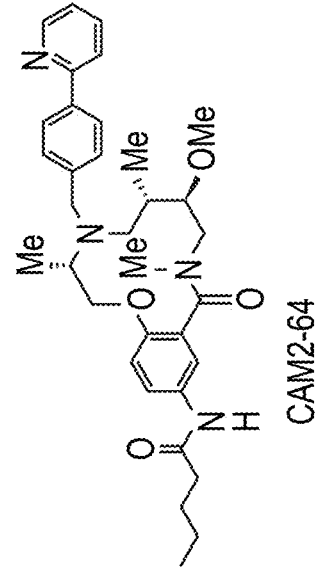
Figure 5:
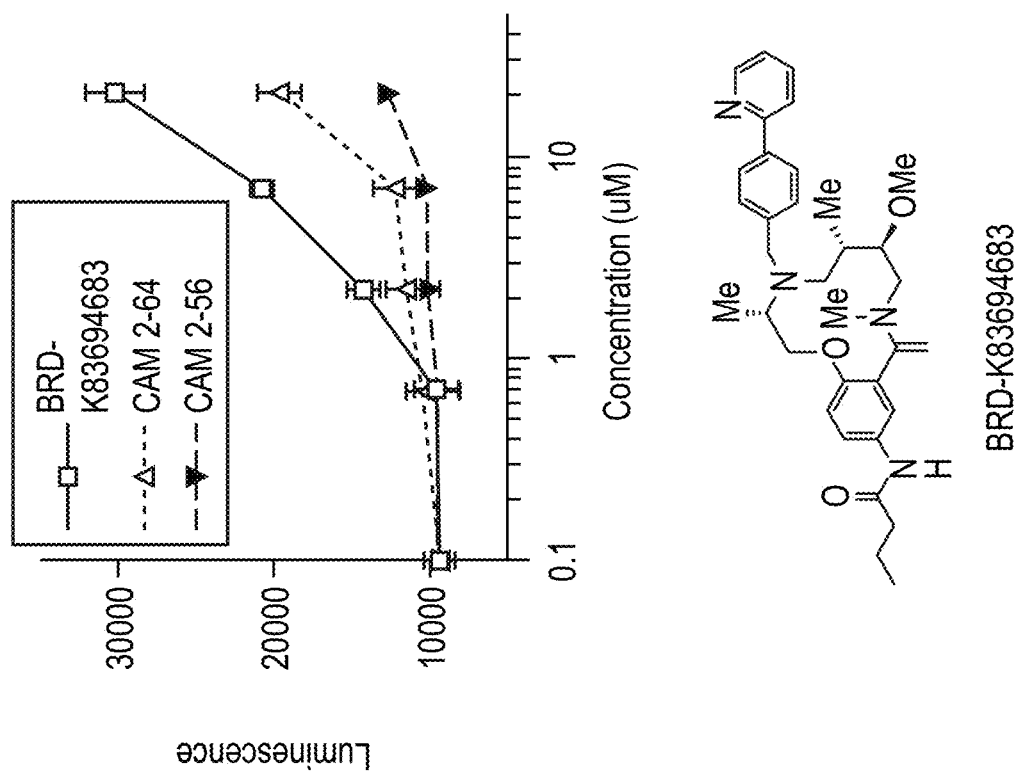
Figure 5:
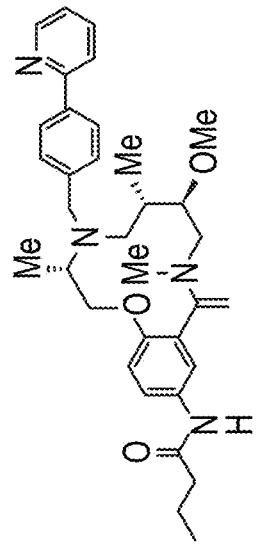
Figure 5:
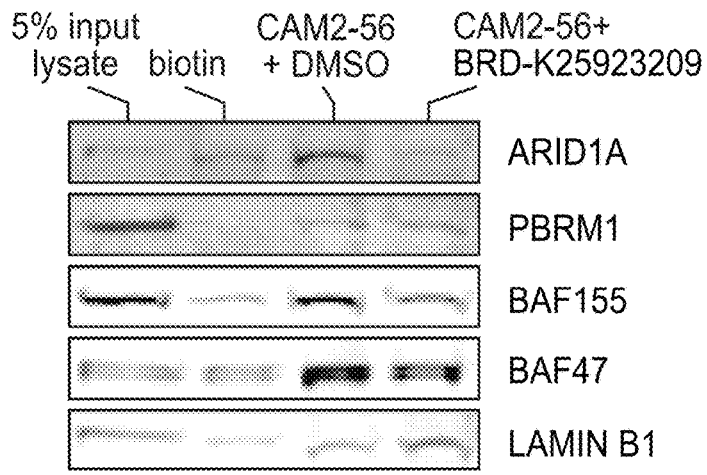
Figure 5:
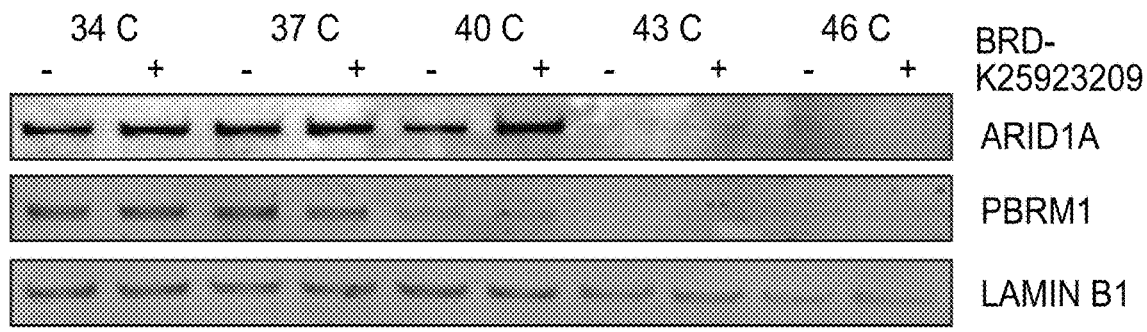
Figure 5:
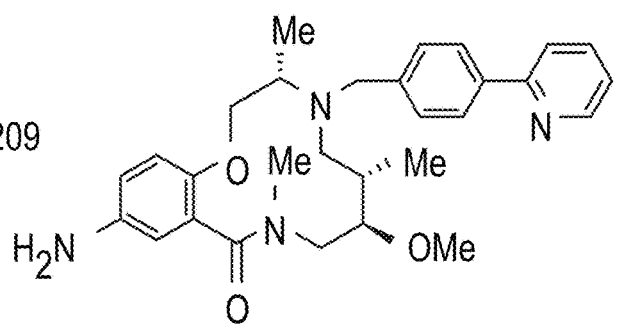
Figure 5:
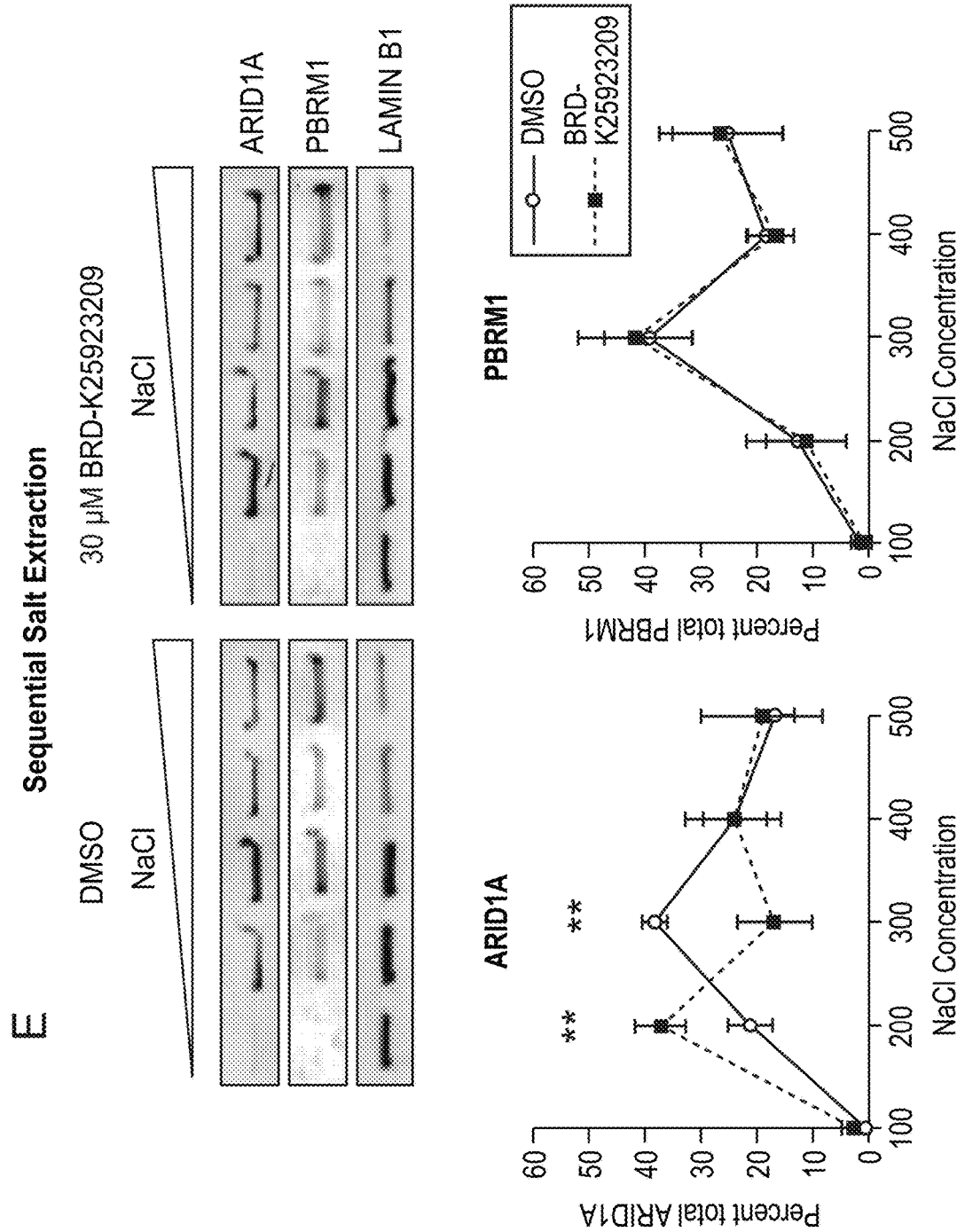
Figure 5:
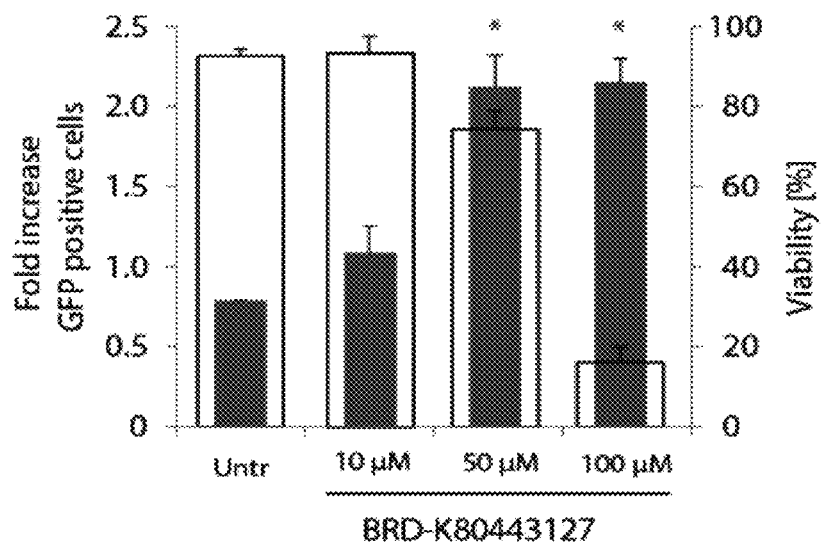
Figure 5:
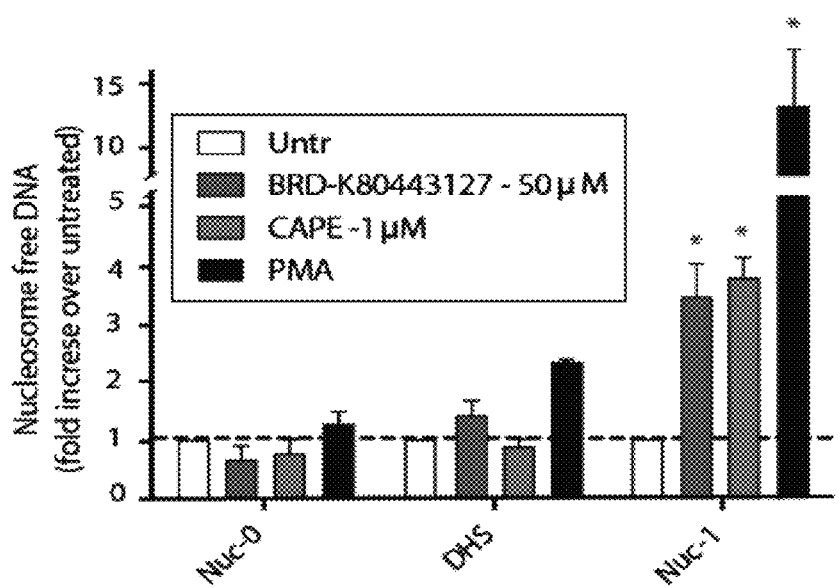
Figure 6:
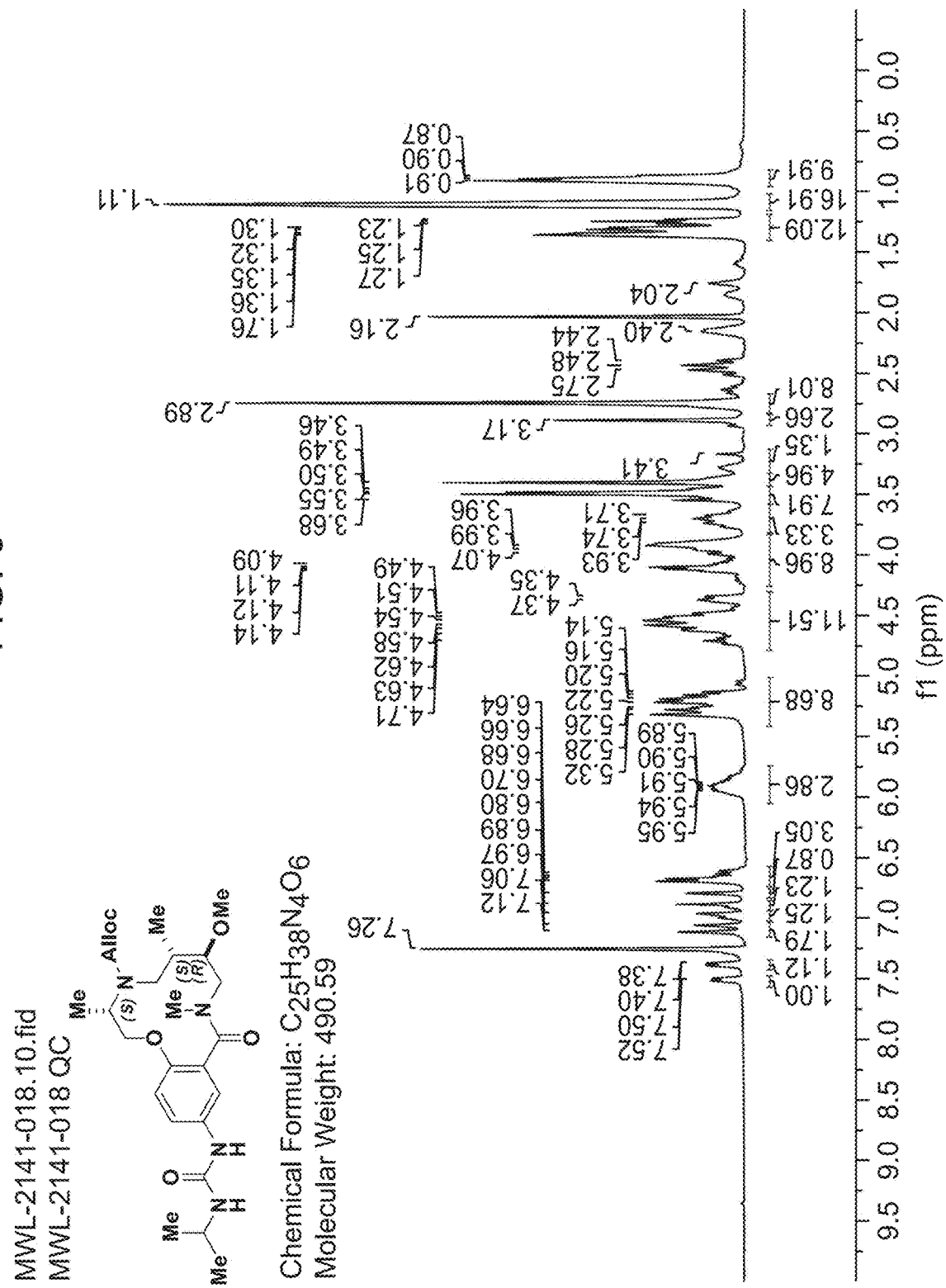
FIG. 6: Acylation of the Aniline (2141-018). Isopropyl isocyanate (0.174 ml, 1.767 mmol) was added dropwise to a stirring solution of crude aniline (2141-018b) (0.597 g, 1.472 mmol) in CH2Cl2 (Volume: 7.36 ml) and reaction was stirred at rt overnight. LC/MS showed conversion into the desired product. The solvent was evaporated and the residue was purified via ISCO (0.5-9% MeOH in CH2Cl2, 18 min); Collected fractions 40-52 to afford the product as a white solid foam. 644 mg (89% over 2 steps) $(M+H)^+$ calculated=491.29 $(M+H)^+$ measured (LC/MS)=492.73
Figure 6:
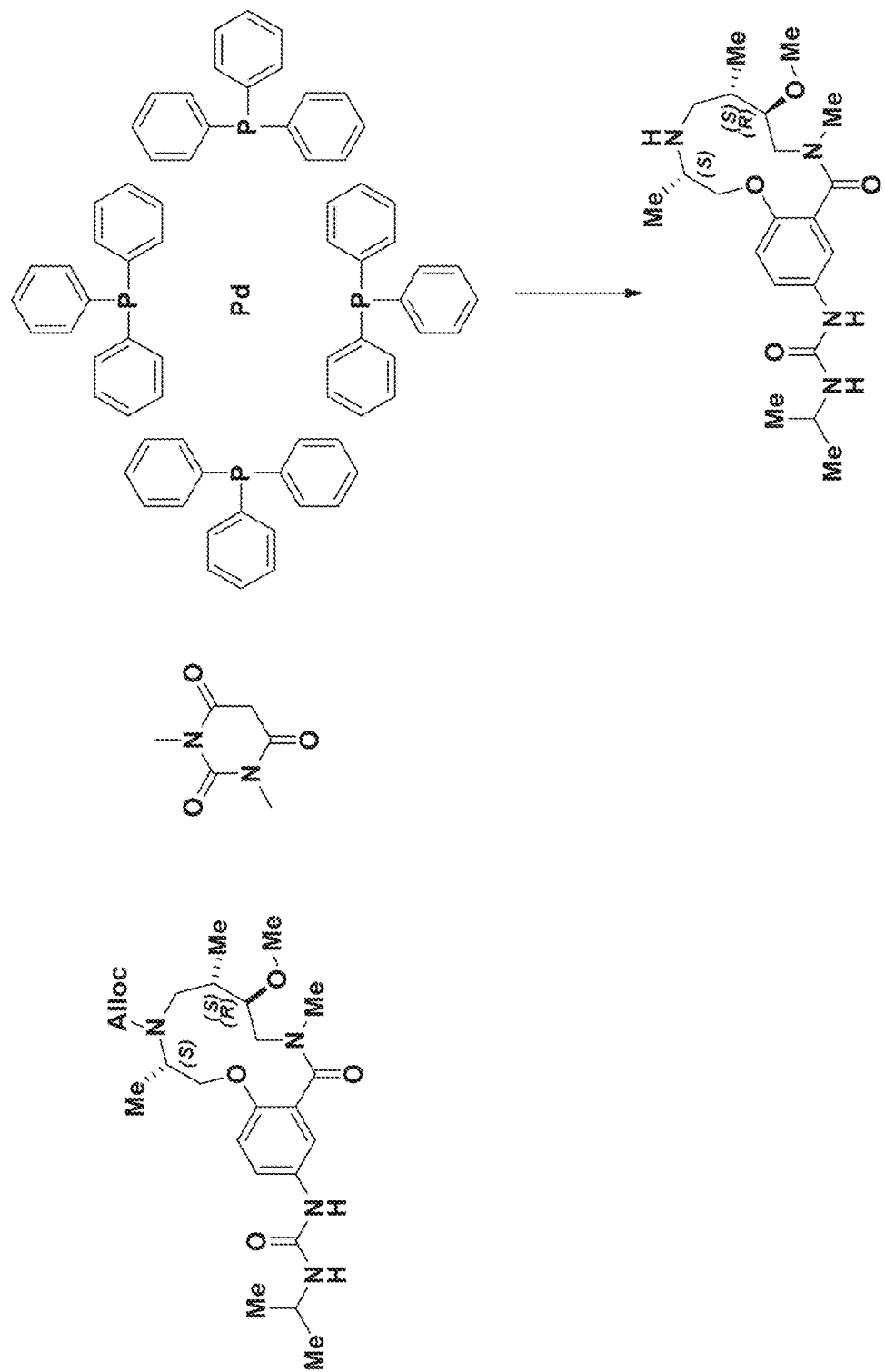
Figure 7:
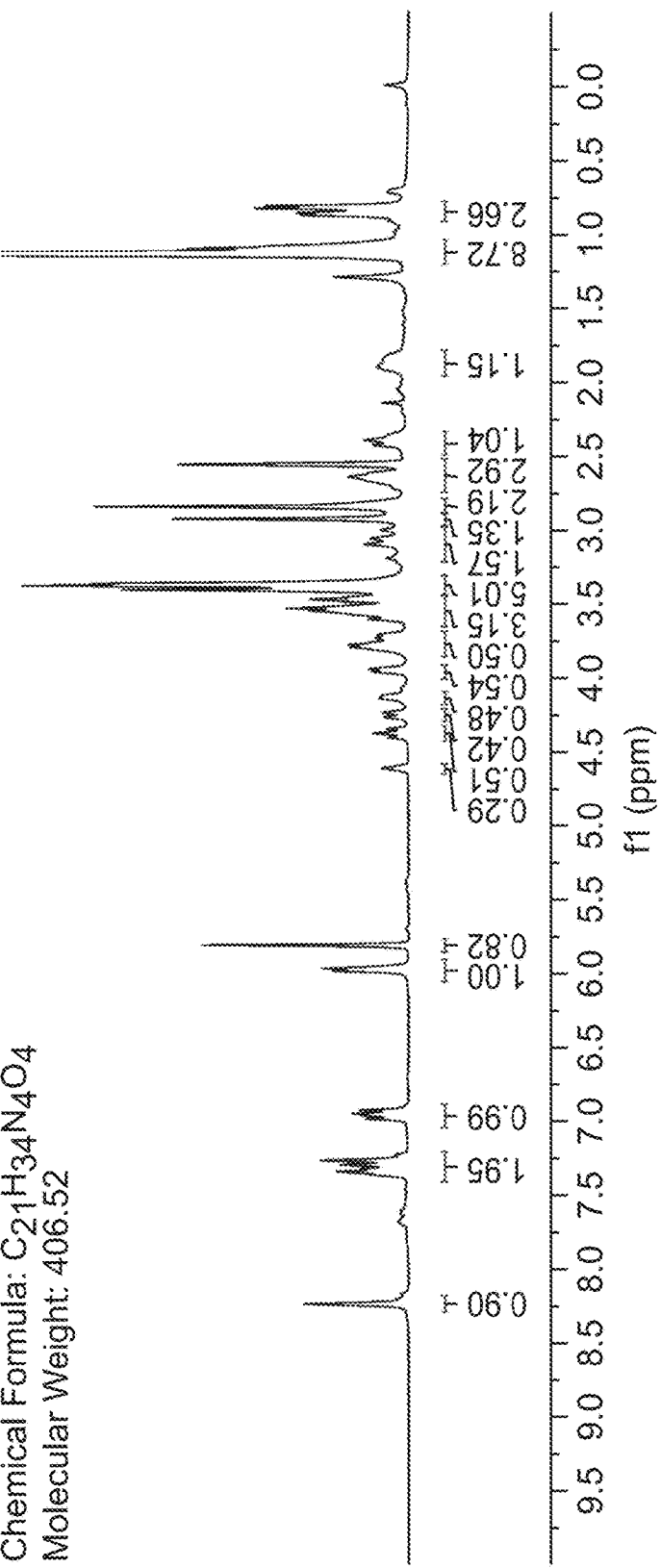
FIG. 7: Alloc deprotection (2141-022): A 100 mL round-bottomed flask was charged with a solution of Urea (2141-018) (0.625 g, 1.274 mmol) in EtOH/CH$_2$Cl$_2$ (2:1). 1,3-Dimethylbarbituricacid (0.298 g, 1.911 mmol) was added in one portion at room temperature, followed by Tetrakis (triphenylphosphine)palladium(0) (0.147 g, 0.127 mmol). The mixture was stirred at 40° C. for ~16 h (overnight) or until LC/MS demonstrated conversion into a product with the same mass. The solvents were removed in vacuo, and the crude residue was dissolved in CH$_2$Cl$_2$ and passed through a plug of acidic resin (5 equiv relative to SM) rinsing with CH$_2$Cl$_2$ (~3 column volumes). The amine was then eluted with 1M NH$_3$ in MeOH to afford sufficiently clean material from next step. $(M+H)^+$ calculated=407.27 $(M+H)^+$ measured (LC/MS)=407.56
Figure 7:
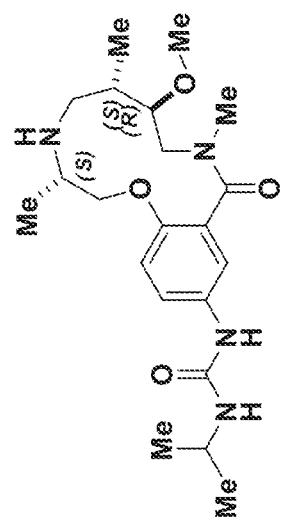
Figure 7:
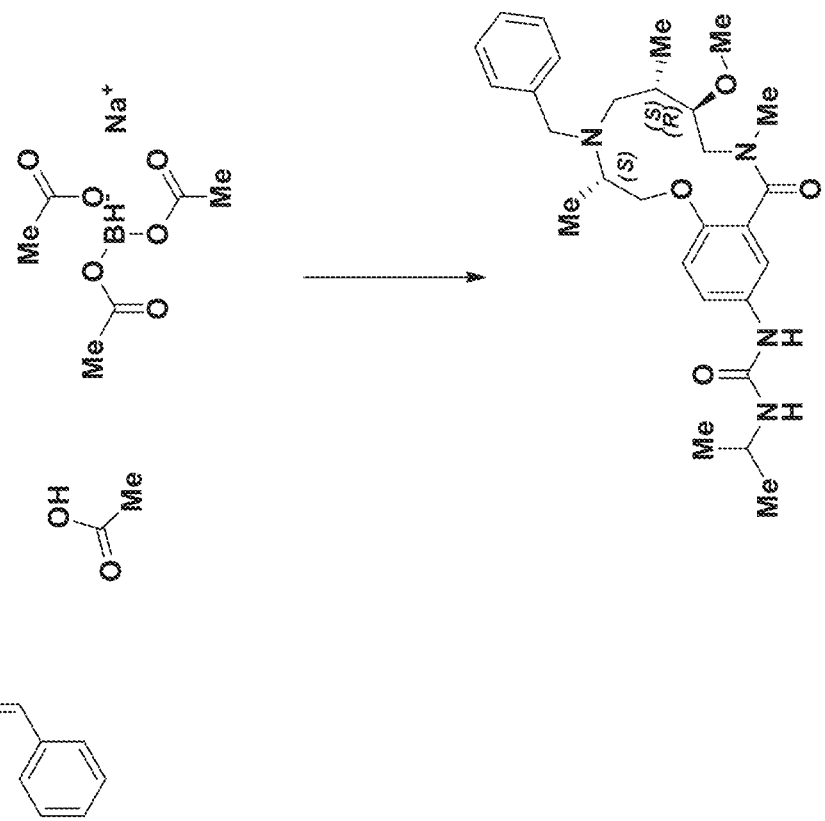
Figure 8:
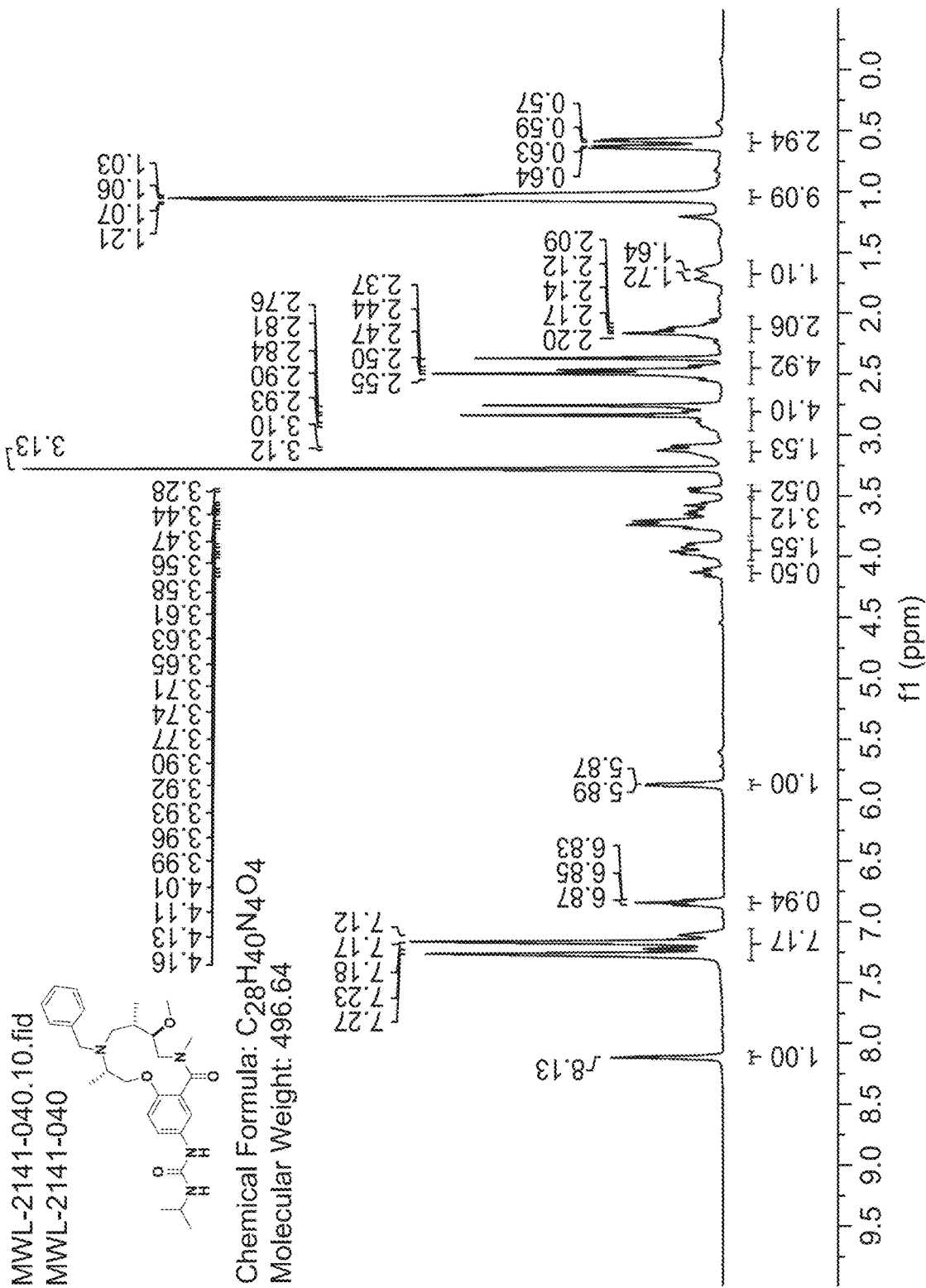
FIG. 8: BRD-K13648511: Benzaldehyde (0.090 ml, 0.886 mmol) was added to a DMF (Volume: 2.95 ml) solution of crude amine (2141-022) (0.12 g, 0.295 mmol) at rt. Acetic acid (0.017 ml, 0.295 mmol) was added and the mixture was stirred for 30 min before sodium triacetoxyhydroborate (0.250 g, 1.181 mmol) was added. The resulting mixture was stirred at rt overnight. LCMS indicates complete SM consumption. Saturated aqueous sodium bicarbonate solution was slowly added until gas evolution ceased. The reaction mixture was diluted with EtOAc and the layers were separated. The organic layer was washed with brine, dried with MgSO$_4$, filtered, and concentrated. The residue was purified via ISCO (SiO$_2$, 1-12% MeOH in CH$_2$Cl$_2$, 20 min, 254 nm); Collected fractions 47-54 to afford the product as a white solid in 23% yield (34 mg) over 2 steps. $(M+H)^+$ calculated=497.3123, $(M+H)^+$ average (3 ESI replicates)= 497.3131±1.81
Figure 8:
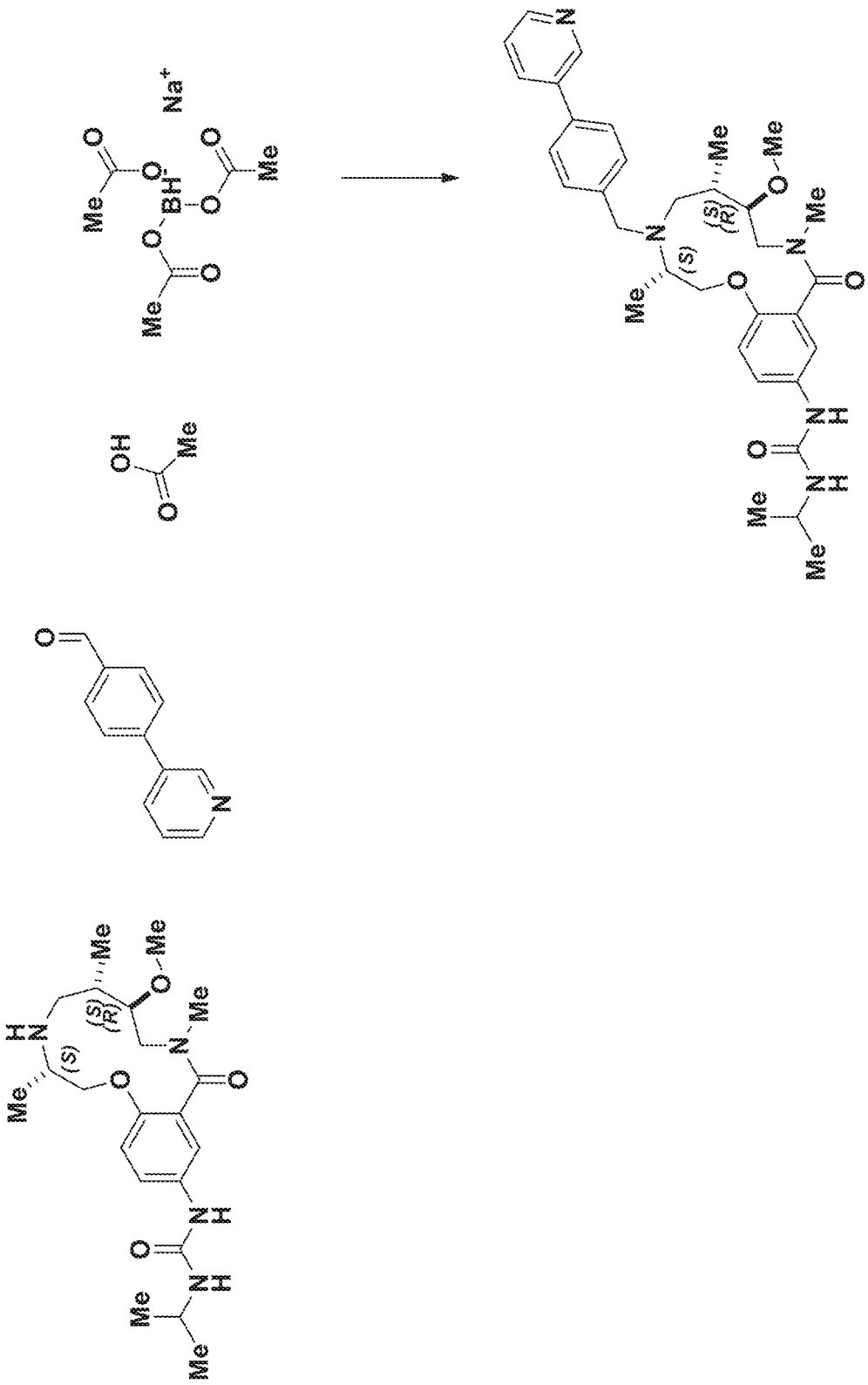
Figure 9:
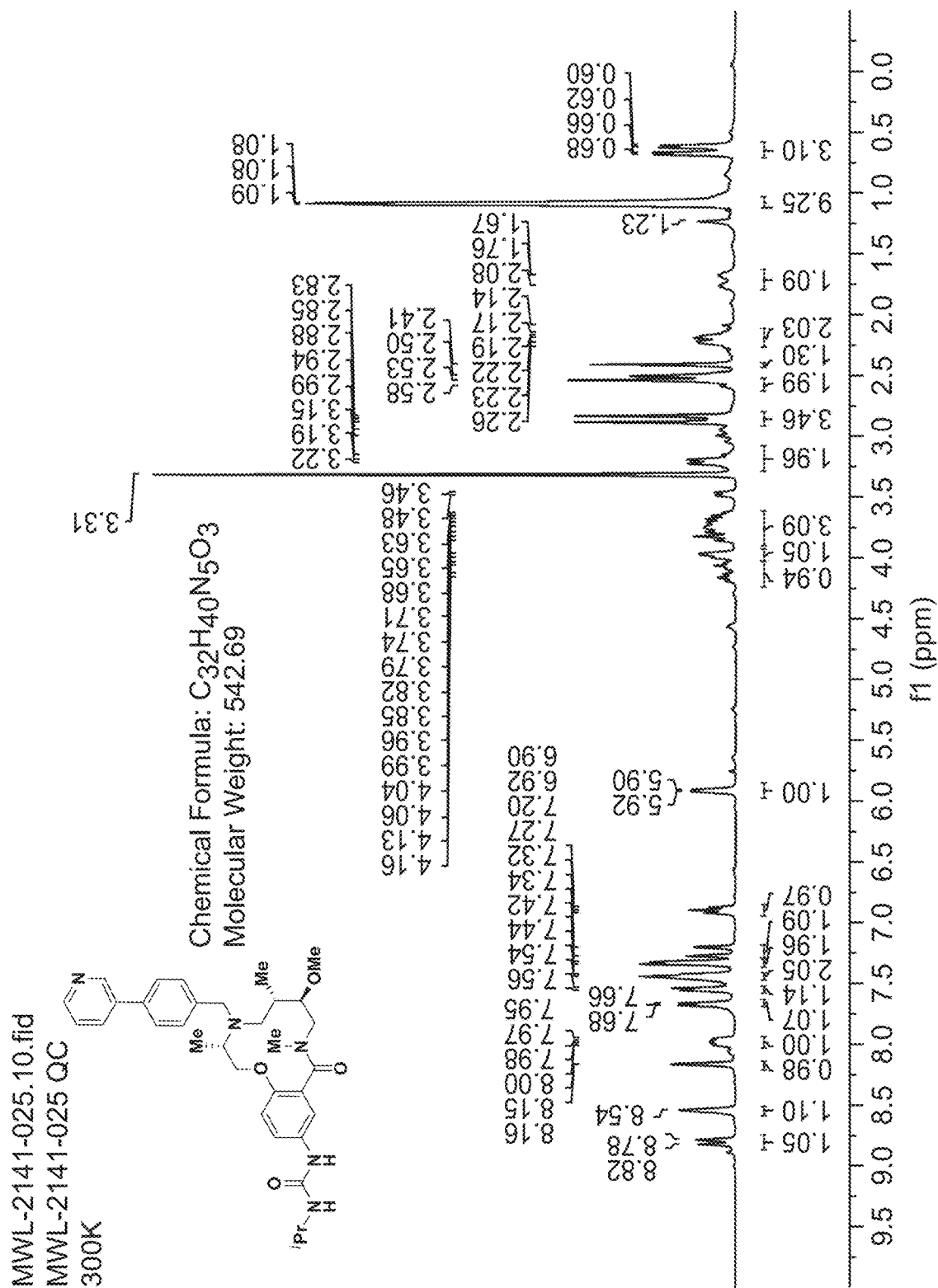
FIG. 9: BRD-K17257309: 4-(pyridin-3-yl)benzaldehyde (151 mg, 0.827 mmol) was added to a DMF (Volume: 1378 µl, Density: 0.944 g/ml) solution of Crude amine (2141-022) (112 mg, 0.276 mmol) at rt. Acetic acid (15.77 µl, 0.276 mmol) was added and the mixture was stirred for 30 min before sodium triacetoxyhydroborate (234 mg, 1.102 mmol) was added and the mixture was stirred at rt overnight or until LC/MS indicates conversion into product. Saturated aq sodium bicarbonate solution was slowly added until gas evolution ceased. The reaction mixture was diluted with EtOAc and the layers were separated. The aqueous phase was extracted with EtOAc (3×). The combined organic layers were washed with brine, dried with MgSO$_4$, filtered, and concentrated. The residue was purified via ISCO (0.5-
Figure 9:
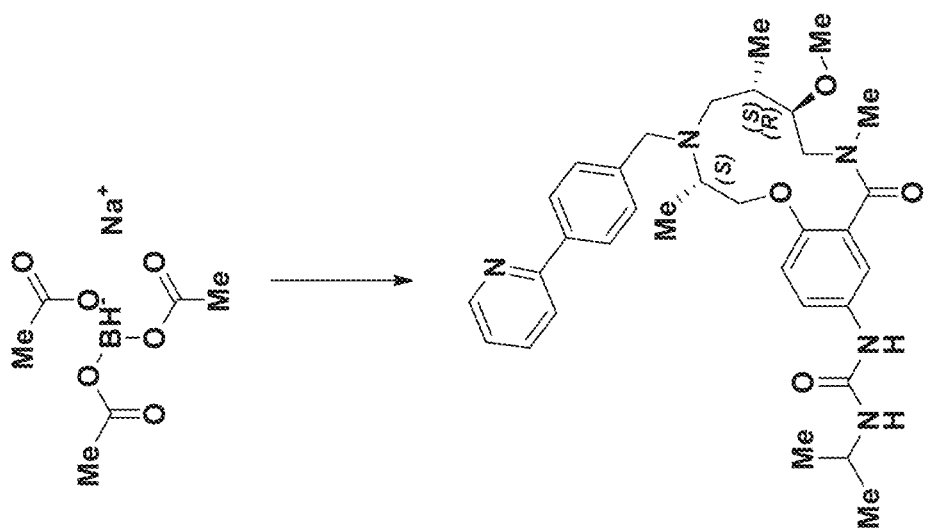
Figure 9:
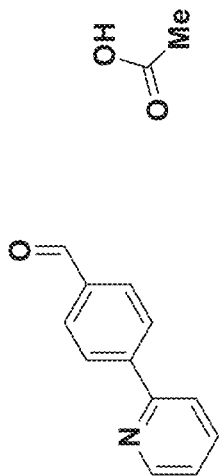
Figure 9:
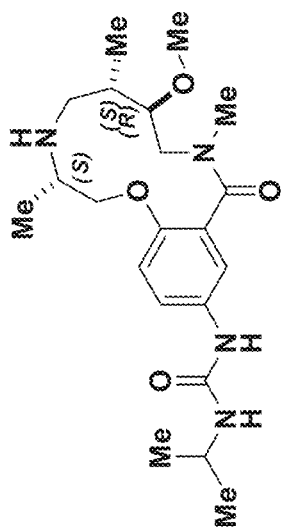

G. Validation of BAF-Mediated Transcriptional Effects:

To define how well the BAF inhibitors mimic the transcriptional profile of BAF deletion we performed RNA-Seq analysis on mESCs treated with 30 µM BRD-K98645985 or DMSO for 18 h. We found 3534 differentially regulated genes upon compound treatment (1.5-fold change, P<0.05), with 1518 up and 1916 down upon compound treatment. Comparing the gene overlap with published RNA-Seq data from Brg1 knockout in mES cells[70] leads to significant (2.3-fold enrichment over predicted, p=1.47×10$^{-33}$) overlap of gene expression (FIG. 5A). This high degree in overlap indicates that BRD-K98645985 targets similar pathways regulated by BRG1 in ES cells. The incomplete overlap could be due to off-target effects, the phenotypic difference between acute inhibition and deletion of a subunit, the possibility of the compound targeting of a subunit different than BRG1, different ES cell lines, different experimental conditions, and different analysis conditions. Further analysis of the overlapping genes shows significant enrichment of genes in pathways related to neuronal development and morphogenesis, consistent with phenotypes reported for Arid1a knockout ESCs, in particular a loss of pluripotency and a propensity for differentiation into neurons[71]. We then performed RNA-Seq analysis with Arid1a knockout ESCs and identified 1141 differentially regulated genes (1.5-fold change, P<0.05). A higher percentage of the ARID1A-regulated genes overlapped with compound treated cells (2.7-fold enrichment over predicted, p=6.55×10$^{-58}$) than BRG1-regulated genes. In addition, the canonical pathways identified for the differential genes from each dataset were the most similar between the ARID1A KO cells and BRD-K98645985 treated cells. This, in conjunction with parallel studies with screen hits in the context of ARID1A mutant cancer cell lines and ATR synergy (Chory et al. Submitted), led us to hypothesize ARID1A to be the primary target of the macrolactams.

H. Validation of ARID1A Targeting:

Based on the SAR we hypothesized that the R1 position would be amenable to linker attachment for protein target identification; however, the synthesis of analog CAM 2-64 with a single methylene addition compared to BRD-K83694683 resulted in a significant decrease in activity (FIG. 5B). Further modification with a longer linker attached to biotin in CAM 2-56 further reduced activity in a cell-based system (FIG. 5B). While CAM 2-56 may suffer from poor cell permeability due to the addition of biotin, it is unlikely that the pharmacokinetics of CAM 2-64 is significantly altered due to the addition of a single methylene onto BRD-K83694683, implying that the binding site doesn't tolerate additional bulk at R2. Nevertheless, since we observed some activity of the biotin-linked compound CAM 2-56, we used it in combination with streptavidin support for affinity purification. In accordance with reduced binding affinity of these linkered macrolactams, we saw only moderate enrichment of ARID1A from ES cell lysates (FIG. 5C, FIG. S5A Marian et al., Ibid.); however, we did observe a complete reduction of ARID1A enrichment upon preincubation of lysates with 200 µM of soluble BRD-K25923209, indicating selective binding (FIG. 5C, FIG. S5A Marian et al., Ibid.). In addition, we observed only non-specific enrichment of PBAF subunit PBRM1 and loading control LaminB1. In agreement with the compounds targeting the ARID1A-containing BAF complexes, we observed a decrease in enrichment for BAF155 and BAF47, which are subunits of both BAF and PBAF. While these experiments indicate direct binding to ARID1A, they are complicated by the decrease in affinity upon linking the compound to solid support. To circumvent the need for a derivatized scaffold for target ID, we turned to CETSA, a cell-based technique[72]. CETSA is based on the principle that the stability of a protein will be increased upon binding to a small molecule ligand, which can be visualized using immunoblot analysis after incubation of cells across a temperature gradient followed by removal of the insoluble, denatured proteins. Since ARID1A is a dedicated member of the large, 2 MDa SWI/SNF complex, changes in protein stability from binding a small molecule would be difficult to discern; however, we did observe a small but reproducible increase in ARID1A stability, but not PBRM1 or LaminB1 stability, upon compound treatment, providing further preliminary evidence that the compound binds ARID1A (FIG. 5D). The known enzymatic activity of the BAF chromatin remodeling complex is DNA-stimulated ATP hydrolysis via the BRG1 subunit; however, we observed only slight inhibition of the ATPase activity at high concentrations of compound (FIG. S5B Marian et al., Ibid.) indicating that this is not its primary mode of action. Similarly, we performed glycerol gradients to assess whether compounds affect BAF complex formation and did not observe any significant disruption to BAF complex integrity upon compound treatment (FIG. S5C Marian et al., Ibid.). When we used a sequential salt extraction to investigate the possibility of the compounds inhibiting ARID1A association with chromatin, we saw a significant and reproducible shift in ARID1A elution but not PBRM1 elution upon treatment with compound (FIG. 5E Marian et al., Ibid.). Although these shifts are small in nature, they are very reproducible between experiments and consistent with affinity shifts previously observed upon deletion of a single BAF complex subunit or mutation of a single chromatin binding domain within large BAF complexes[73].

I. Mechanism of Action in HIV Latency Reversal:

To examine the mechanism for how these BAF inhibitors might be inhibiting ARID1A-mediated repression, we used the J-Lat T-cell line models of HIV-1 latency, in which activation of transcription from the latent provirus results in GFP synthesis. We confirmed concentration dependent latency reversal upon treatment with BRD-K98645985, although at higher concentrations than in primary cells (FIG. 5F, FIG. S5D Marian et al., Ibid.)). We investigated how nucleosome occupancy at the 5'-LTR changes upon treatment with BRD-K80443127 in J-Lat 11.1 using the formaldehyde assisted isolation of regulatory elements (FAIRE) assay, which is a measure of chromatin accessibility[74]. Overnight compound treatment resulted in increased chromatin accessibility at the Nuc-1 position of the 5' LTR (FIG. 5G) mimicking the effect elicited by the siRNA knockdown of ARID1A and treatment with BAF inhibitors identified in our previous studies[43,55]. This further validates the role of the macrolactams in inhibiting BAF-mediated nucleosome positioning established during HIV-1 transcriptional repression.

IV. DISCUSSION

While the mammalian SWI/SNF chromatin remodeling complex is often referred to as a single protein complex, it is actually a heterogeneous assembly of closely related protein complexes with different biochemical and biological functions[75,76]. Several of these subcomplexes have been determined to be mis-regulated in disease, implicating subunits of SWI/SNF complexes as potential drug targets[77-78]. A significant challenge for drug development is that general inhibition of SWI/SNF chromatin remodeling function may have undesirable toxicity as many, if not most, cell types require some form of SWI/SNF chromatin remodeling for basic viability[77-79]. Further complicating matters, it is still unclear how the biochemical functions of individual subunits of chromatin remodeling complexes are related to desired phenotypes, making it difficult to design and implement biochemical screening programs. To circumvent these issues, we developed a robust high throughput phenotypic screen designed to identify small molecules that inhibit BAF-mediated transcription without affecting cellular viability. From this screen, we have identified a novel 12-membered macrolactam inhibitor with low toxicity and the ability to inhibit the transcriptional activities of the BAF complex. These BAF inhibitors (BAFi) have significant promise as an HIV-1 latency reversal agent, particularly because of their potential for clinical use in combination therapy with other currently available LRAs. Indeed, we show that BRD-K80443127 treatment efficiently triggered HIV transcription in ex vivo infected primary CD4+T cells harboring latent HIV and potentiated the effect of other latency reversal agents when used in combination. In CD4+ T cells isolated from c-ART treated virologically suppressed HIV-1 infected patients, a significant increase in cell associated HIV mRNA was observed after ex vivo treatment with BRD-K80443127 alone in one patient, while in all three patients, BRD-K80443127 treatment lead to significant potentiation of prostratin activity. The mechanism of action of BAFi's is that of de-repression, or inhibition of the HIV-1 LTR-bound repressive BAF complex. Our observed modest and variable effects in latency reversal by BRD-K80443127 alone is consistent with this notion and points to the need for larger patient cohorts in order to test the activity of this compound with robust across patient statistics. Importantly, in line with the mechanism of action of BRD-K80443127 as an LTR de-repressor, co-treatment with the PKC agonist prostratin, which is a bona fide activator of HIV transcription resulted in significant increase in cell associated HIV RNA in all patients. This is in line with recent findings that ARID1A degraders from our previous studies[55] act to increase transcriptional noise (frequency or burst) at the HIV-1 LTR promoter[80]. This points to the use for this class of compounds for inclusion in combinatorial therapy with other drugs targeting different steps in HIV transcription. Target identification and mechanistic work indicates that this inhibitor binds the ARID1A-containing BAF complexes and prevents ARID1A function at the 5' LTR of HIV-1, although the exact mechanism of compound action is still to be resolved.

V. CONCLUSION

The persistence of a pool of latently HIV-1-infected cells despite combination Anti-Retroviral Therapy (cART) treatment is the major roadblock for a cure. The BAF (mammalian SWI/SNF) chromatin remodeling complex is involved in establishing and maintaining viral latency through nucleosome positioning, making it an attractive drug target for HIV-1 latency reversal. Here we report a high throughput screen for inhibitors of BAF-mediated transcription in cells and the subsequent identification of a novel 12-membered macrolactam. This compound targets the BAF-specific subunit ARID1A to prevent nucleosomal positioning, relieving transcriptional repression of HIV-1 and reversing latency in an in vitro T cell line, an ex vivo primary cell model of HIV-1 latency, and in patient CD4+ T cells without toxicity or T cell activation. These novel macrolactams represent a new class of latency reversal agents with unique mechanism of action, and can be combined with other LRAs to improve reservoir targeting.

The BAF (SWI/SNF) chromatin remodeling complex has long been an attractive target for drug development; however, the heterogenous nature of BAF complexes, along with undefined biochemical functions for disease-related subunits has made the development of small molecule screening platforms particularly challenging. Here, we have developed a reporter cell line of BAF-mediated transcriptional repression and identified a novel macrolactam inhibitor of the BAF chromatin remodeling complex using high throughput screening. This optimized class of compounds activates the expression of BAF-repressed genes in embryonic stem cells and are similarly able to activate transcription at the in in vitro cell line models of HIV-1 latency and in primary human CD4+ T cells harboring latent HIV-1. Importantly, these compounds do not display T cell toxicity or T cell activation, which is associated with many latency reversal agents. Target identification and phenotypic analysis points to the inhibition of ARID1A-containing BAF complexes, which are selectively involved in maintaining HIV-1 latency. This study validates the strategy of targeting individual BAF subcomplexes involved in disease and identifies a novel macrolactam scaffold developed using diversity oriented synthesis. This class of compounds is a useful starting point for more potent and selective BAF inhibitors, which can be used in combination with other latency reversal agents to activate HIV-1 transcription and eliminate the latently infected cell population.

VI. REFERENCES

1. Barré-Sinoussi, F. et al. Isolation of a T-lymphotropic retrovirus from a patient at risk for acquired immune deficiency syndrome (AIDS). *Science* 220, 868-871 (1983).
2. Deeks, S. G., Lewin, S. R. & Havlir, D. V. The end of AIDS: HIV infection as a chronic disease.—PubMed—NCBI. *The Lancet* 382, 1525-1533 (2013).
3. Maartens, G., Celum, C. & Lewin, S. R. HIV infection: epidemiology, pathogenesis, treatment, and prevention. *The Lancet* 384, 258-271 (2014).
4. Finzi, D. et al. Identification of a reservoir for HIV-1 in patients on highly active antiretroviral therapy. *Science* 278, 1295-1300 (1997).
5. Finzi, D. et al. Latent infection of CD4+ T cells provides a mechanism for lifelong persistence of HIV-1, even in patients on effective combination therapy. *Nat Med* 5, 512-517 (1999).
6. Chun, T.-W. et al. Quantification of latent tissue reservoirs and total body viral load in HIV-1 infection.—PubMed—NCBI. *Nature* 387, 183-188 (1997).
7. Ruelas, D. S. & Greene, W. C. An Integrated Overview of HIV-1 Latency. *Cell* 155, 519-529 (2013).
8. Siliciano, J. D. et al. Long-term follow-up studies confirm the stability of the latent reservoir for HIV-1 in resting CD4+ T cells. *Nat Med* 9, 727-728 (2003).
9. Chun, T.-W. et al. Rebound of plasma viremia following cessation of antiretroviral therapy despite profoundly low levels of Hiv reservoir: implications for eradication. *AIDS* 24, 2803-2808 (2010).
10. Dahabieh, M., Battivelli, E. & Verdin, E. Understanding HIV Latency: The Road to an HIV Cure. *Annual review of medicine* 66, 407-421 (2015).
11. De Crignis, E. & Mahmoudi, T. The Multifaceted Contributions of Chromatin to HIV-1 Integration, Transcription, and Latency. *International Review of Cell and Molecular Biology* 328, 197-252 (2017).
12. Cillo, A. R. & Mellors, J. W. Which therapeutic strategy will achieve a cure for HIV-1?*Current Opinion in Virology* 18, 14-19 (2016).
13. Churchill, M. J., Deeks, S. G., Margolis, D. M., Siliciano, R. F. & Swanstrom, R. HIV reservoirs: what, where and how to target them. *Nature Reviews Microbiology* 14, 55-60 (2016).
14. Siliciano, J. D. & Siliciano, R. F. Recent developments in the effort to cure HIV infection: going beyond N=1. *Journal of Clinical Investigation* 126, 409-414 (2016).
15. Margolis, D. M. Towards an HIV Cure: a View of a Developing Field. *The Journal of Infectious Diseases* 215, S109-S110 (2017).
16. Martrus, G. & Altfeld, M. Immunological strategies to target HIV persistence.—PubMed—NCBI. *Current Opinion in HIV and AIDS* 11, 402-408 (2016).
17. Trautmann, L. Kill. *Current Opinion in HIV and AIDS* 11, 409-416 (2016).
18. Perreau, M., Banga, R. & Pantaleo, G. Targeted Immune Interventions for an HIV-1 Cure. PubMed—NCBI. *Trends Mol Med* (2017). doi:10.1016/j.molmed.2017.08.006
19. Brockman, M. A., Jones, R. B. & Brumme, Z. L. Challenges and Opportunities for T-Cell-Mediated Strategies to Eliminate HIV Reservoirs. *Frontiers in Immunology* 6, 692 (2015).
20. Barouch, D. H. & Deeks, S. G. Immunologic strategies for HIV-1 remission and eradication. *Science* 345, 169-174 (2014).
21. Margolis, D. M., Garcia, J. V., Hazuda, D. J. & Haynes, B. F. Latency reversal and viral clearance to cure HIV-1. *Science* 353, aaf6517-aaf6517 (2016).
22. Deeks, S. G. HIV: Shock and kill. *Nature* 487, 439-440 (2012).
23. Rasmussen, T. A., Tolstrup, M. & Segaard, O. S. Reversal of Latency as Part of a Cure for HIV-1.—PubMed—NCBI. *Trends in Microbiology* 24, 90-97 (2016).
24. Margolis, D. M. & Archin, N. M. Proviral Latency, Persistent Human Immunodeficiency Virus Infection, and the Development of Latency Reversing Agents.—PubMed—NCBI. *The Journal of Infectious Diseases* 215, S111-S118 (2017).
25. Verdin, E. DNase I-hypersensitive sites are associated with both long terminal repeats and with the intragenic enhancer of integrated human immunodeficiency virus type 1. *J Virol* 65, 6790-6799 (1991).
26. Verdin, E., Paras, P. & Van Lint, C. Chromatin disruption in the promoter of human immunodeficiency virus type 1 during transcriptional activation. *EMBO J* 12, 3249-3259 (1993).
27. Turner, A.-M. W. & Margolis, D. M. Chromatin Regulation and the Histone Code in HIV Latency. *Yale J Biol Med* 90, 229-243 (2017).
28. Mbonye, U. & Karn, J. Transcriptional control of HIV latency: cellular signaling pathways, epigenetics, happenstance and the hope for a cure.—PubMed—NCBI. *Virology* 454-455, 328-339 (2014).
29. Kumar, A., Darcis, G., Van Lint, C. & Herbein, G. Epigenetic control of HIV-1 post integration latency: implications for therapy. *Clin Epigenetics* 7, 103 (2015).
30. Van Lint, C., Bouchat, S. & Marcello, A. HIV-1 transcription and latency: an update. *Retrovirology* 10, 67 (2013).
31. Conrad, R. J. & Ott, M. Therapeutics Targeting Protein Acetylation Perturb Latency of Human Viruses. *ACS Chem. Biol.* acschembio.5b00999 (2016). doi:10.1021/acschembio.5b00999
32. Rasmussen, T. A. et al. Comparison of HDAC inhibitors in clinical development: Effect on HIV production in latently infected cells and T-cell activation. *Human Vaccines & Immunotherapeutics* 9, 993-1001 (2013).
33. Archin, N. M. et al. Administration of vorinostat disrupts HIV-1 latency in patients on antiretroviral therapy. *Nature* 487, 482-485 (2012).
34. Wei, D. G. et al. Histone Deacetylase Inhibitor Romidepsin Induces HIV Expression in CD4 T Cells from Patients on Suppressive Antiretroviral Therapy at Concentrations Achieved by Clinical Dosing. *PLoS Pathog* 10, e1004071 (2014).
35. Wightman, F. et al. Entinostat is a histone deacetylase inhibitor selective for class 1 histone deacetylases and activates HIV production from latently infected primary T cells. *AIDS* 27, 2853-2862 (2013).

36. Van Lint, C., Emiliani, S., Ott, M. & Verdin, E. Transcriptional activation and chromatin remodeling of the HIV-1 promoter in response to histone acetylation. *EMBO J* 15, 1112-1120 (1996).
37. Sheridan, P. L., Mayall, T. P., Verdin, E. & Jones, K. A. Histone acetyltransferases regulate HIV-1 enhancer activity in vitro. *Gene Dev* 11, 3327-3340 (1997).
38. Archin, N. M. et al. HIV-1 Expression Within Resting CD4+ T Cells After Multiple Doses of Vorinostat. *The Journal of Infectious Diseases* 210, 728-735 (2014).
39. Spivak, A. M. & Planelles, V. HIV-1 Eradication: Early Trials (and Tribulations). *Trends Mol Med* 22, 10-27 (2016).
40. Søgaard, O. S. et al. The Depsipeptide Romidepsin Reverses HIV-1 Latency In Vivo. *PLoS Pathog* 11, e1005142 (2015).
41. Elliott, J. H. et al. Activation of HIV transcription with short-course vorinostat in HIV-infected patients on suppressive antiretroviral therapy. *PLoS Pathog* 10, e1004473 (2014).
42. Delagrèverie, H. M., Delaugerre, C., Lewin, S. R., Deeks, S. G. & Li, J. Z. Ongoing Clinical Trials of Human Immunodeficiency Virus Latency-Reversing and Immunomodulatory Agents. *Open Forum Infect Dis* 3, ofw189 (2016).
43. Rafati, H. et al. Repressive LTR Nucleosome Positioning by the BAF Complex Is Required for HIV Latency. *Plos Biol* 9, e1001206 (2011).
44. Boese, A., Sommer, P., Holzer, D., Maier, R. & Nehrbass, U. Integrase interactor 1 (Ini1/hSNF5) is a repressor of basal human immunodeficiency virus type 1 promoter activity.—PubMed—NCBI. *J. Gen. Virol.* 90, 2503-2512 (2009).
45. Van Duyne, R. et al. Varying modulation of HTLV-1 LTR activity by BAF complexes. *Retrovirology* 8, A 180 (2011).
46. Ho, L. & Crabtree, G. R. Chromatin remodelling during development. *Nature* 463, 474-484 (2010).
47. Pulice, J. L. & Kadoch, C. Composition and Function of Mammalian SWI/SNF Chromatin Remodeling Complexes in Human Disease. *Cold Spring Harb. Symp. Quant. Biol.* 031021 (2017). doi:10.1101/sqb.2016.81.031021
48. Hodges, C., Kirkland, J. G. & Crabtree, G. R. The Many Roles of BAF (mSWI/SNF) and PBAF Complexes in Cancer. *Cold Spring Harb Perspect Med* 6, a026930 (2016).
49. Mahmoudi, T. et al. The SWI/SNF chromatin-remodeling complex is a cofactor for Tat transactivation of the HIV promoter. *J Biol Chem* 281, 19960-19968 (2006).
50. Tréand, C. et al. Requirement for SWI/SNF chromatin-remodeling complex in Tat-mediated activation of the HIV-1 promoter. *EMBO J* 25, 1690-1699 (2006).
51. Agbottah, E., Deng, L., Dannenberg, L. O., Pumfery, A. & Kashanchi, F. Effect of SWI/SNF chromatin remodeling complex on HIV-1 Tat activated transcription. *Retrovirology* 3, 48 (2006).
52. Easley, R. et al. Transcription through the HIV-1 nucleosomes: Effects of the PBAF complex in Tat activated transcription. *Virology* 405, 322-333 (2010).
53. Conrad, R. J. et al. The Short Isoform of BRD4 Promotes HIV-1 Latency by Engaging Repressive SWI/SNF Chromatin-Remodeling Complexes. *Mol Cell* 0, (2017).
54. Dykhuizen, E. C., Carmody, L. C., Tolliday, N., Crabtree, G. R. & Palmer, M. A. J. Screening for Inhibitors of an Essential Chromatin Remodeler in Mouse Embryonic Stem Cells by Monitoring Transcriptional Regulation. *Journal of Biomolecular Screening* 17, 1221-1230 (2012).
55. Stoszko, M. et al. Small Molecule Inhibitors of BAF; A Promising Family of Compounds in HIV-1 Latency Reversal. *EBioMedicine* 3, 108-121 (2016).
56. Ho, L. et al. An embryonic stem cell chromatin remodeling complex, esBAF, is an essential component of the core pluripotency transcriptional network. *Proceedings of the National Academy of Sciences* 106, 5187-5191 (2009).
57. Auld, D. S., Thorne, N., Nguyen, D.-T. & Inglese, J. A Specific Mechanism for Nonspecific Activation in Reporter-Gene Assays. *ACS Chem. Biol.* 3, 463-470 (2008).
58. Baell, J. B. & Holloway, G. A. New substructure filters for removal of pan assay interference compounds (PAINS) from screening libraries and for their exclusion in bioassays. *J Med Chem* 53, 2719-2740 (2010).
59. Fitzgerald, M. E. et al. Build/Couple/Pair Strategy for the Synthesis of Stereochemically Diverse Macrolactams via Head-to-Tail Cyclization. *ACS Comb. Sci.* 14, 89-96 (2012).
60. Over, B. et al. Structural and conformational determinants of macrocycle cell permeability. *Nat Chem Biol* 12, 1065-1074 (2016).
61. Lassen, K. G., Hebbeler, A. M., Bhattacharyya, D., Lobritz, M. A. & Greene, W. C. A Flexible Model of HIV-1 Latency Permitting Evaluation of Many Primary CD4 T-Cell Reservoirs. *PLoS ONE* 7, e30176 (2012).
62. Bosque, A. & Planelles, V. Induction of HIV-1 latency and reactivation in primary memory CD4+ T cells. *Blood* 113, 58-65 (2009).
63. Cheng, S. W. G. et al. c-MYC interacts with INI1/hSNF5 and requires the SWI/SNF complex for transactivation function. *Nat Genet* 22, 102-105 (1999).
64. Pham, L. V., Tamayo, A. T., Li, C., Bueso-Ramos, C. & Ford, R. J. An epigenetic chromatin remodeling role for NFATc1 in transcriptional regulation of growth and survival genes in diffuse large B-cell lymphomas. *Blood* 116, 3899-3906 (2010).
65. Shi, J. et al. Role of SWI/SNF in acute leukemia maintenance and enhancer-mediated Myc regulation. *Gene Dev* 27, 2648-2662 (2013).
66. Bin Guan, Wang, T.-L. & Shih, I.-M. ARID1A, a Factor That Promotes Formation of SWI/SNF-Mediated Chromatin Remodeling, Is a Tumor Suppressor in Gynecologic Cancers. *Cancer research* 71, 6718-6727 (2011).
67. Korin, Y. D., Brooks, D. G., Brown, S., Korotzer, A. & Zack, J. A. Effects of Prostratin on T-Cell Activation and Human Immunodeficiency Virus Latency. *J Virol* 76, 8118-8123 (2002).
68. DeChristopher, B. A. et al. Designed, Synthetically Accessible Bryostatin Analogues Potently Induce Activation of Latent HIV Reservoirs in vitro. *Nature Chem* 4, 705-710 (2012).
69. Laird, G. M. et al. Ex vivo analysis identifies effective HIV-1 latency-reversing drug combinations. *Journal of Clinical Investigation* 125, 1901-1912 (2015).
70. King, H. W. & Klose, R. J. The pioneer factor OCT4 requires the chromatin remodeller BRG1 to support gene regulatory element function in mouse embryonic stem cells. *eLife Sciences* 6, 380 (2017).
71. Gao, X. et al. ES cell pluripotency and germ-layer formation require the SWI/SNF chromatin remodeling component BAF250a. *Proceedings of the National Academy of Sciences* 105, 6656-6661 (2008).

72. Savitski, M. M. et al. Tracking cancer drugs in living cells by thermal profiling of the proteome. *Science* 346, 1255784-1255784 (2014).
73. Porter, E. G. & Dykhuizen, E. C. Individual Bromodomains of Polybromo-1 Contribute to Chromatin Association and Tumor Suppression in Clear Cell Renal Carcinoma. *J Biol Chem* 292, 2601-2610 (2017).
74. Giresi, P. G., Kim, J., McDaniell, R. M., Iyer, V. R. & Lieb, J. D. FAIRE (Formaldehyde-Assisted Isolation of Regulatory Elements) isolates active regulatory elements from human chromatin. *Genome Research* 17, 877-885 (2007).
75. Wu, J. I., Lessard, J. & Crabtree, G. R. Understanding the Words of Chromatin Regulation. *Cell* 136, 200-206 (2009).
76. Hargreaves, D. C. & Crabtree, G. R. ATP-dependent chromatin remodeling: genetics, genomics and mechanisms. *Cell Res* 21, 396-420 (2011).
77. Hohmann, A. F. & Vakoc, C. R. A rationale to target the SWI/SNF complex for cancer therapy. *Trends Genet.* 30, 356-363 (2014).
78. Schiaffino-Ortega, S., Balinas, C., Cuadros, M. & Medina, P. P. SWI/SNF proteins as targets in cancer therapy. *J Hematol Oncol* 7, 81 (2014).
79. Dykhuizen, E. C. et al. BAF complexes facilitate decatenation of DNA by topoisomerase IIα. *Nature* 497, 624-627 (2013).
80. Megaridis, M. R. et al. Fine-tuning of noise in gene expression with nucleosome remodeling. *APL Bioengineering* 2, 026106 (2018).
81. Stanton, B. Z. et al. Smarca4 ATPase mutations disrupt direct eviction of PRC1 from chromatin. *Nat Genet* (2016). doi:10.1038/ng.3735
82. Kadoch, C. et al. Dynamics of BAF-Polycomb complex opposition on heterochromatin in normal and oncogenic states. *Nat Genet* (2016). doi:10.1038/ng.3734
83. Miller, E. L. et al. TOP2 synergizes with BAF chromatin remodeling for both resolution and formation of facultative heterochromatin. *Nat Struct Mol Biol* 24, 344-352 (2017).
84. Livak, K. J. & Schmittgen, T. D. Analysis of relative gene expression data using real-time quantitative PCR and the 2-ΔΔCT method. *methods* (2001).
85. Bultman, S., Gebuhr, T. & Magnuson, T. A Brg1 mutation that uncouples ATPase activity from chromatin remodeling reveals an essential role for SWI/SNF-related complexes in beta-globin expression and erythroid development. *Gene Dev* 19, 2849-2861 (2005).
86. Jafari, R. et al. The cellular thermal shift assay for evaluating drug target interactions in cells. *Nature Protocols* 9, 2100-2122 (2014).
87. Anders, S. & Huber, W. Differential expression analysis for sequence count data. *Genome Biol* 11, R106 (2010).
88. Chandler, R. L. et al. Coexistent ARID1A-PIK3CA mutations promote ovarian clear-cell tumorigenesis through pro-tumorigenic inflammatory cytokine signalling. *Nat Commun* 6, 6118 (2015).
89. Ho, L. et al. esBAF facilitates pluripotency by conditioning the genome for LIF/STAT3 signalling and by regulating polycomb function. *Nat Cell Biol* 13, 903-913 (2011).
90. Robinson, M. D., McCarthy, D. J. & Smyth, G. K. edgeR: a Bioconductor package for differential expression analysis of digital gene expression data. *Bioinformatics* 26, 139-140 (2010).
91. Jordan, A., Defechereux, P. & Verdin, E. The site of HIV-1 integration in the human genome determines basal transcriptional activity and response to Tat transactivation. *The EMBO Journal* 20, 1726-1738 (2001).
92. Jordan, A., Bisgrove, D. & Verdin, E. HIV reproducibly establishes a latent infection after acute infection of T cells in vitro. *EMBO J* 22, 1868-1877 (2003).
93. BLISS, C. I. THE TOXICITY OF POISONS APPLIED JOINTLY1. *Annals of Applied Biology* 26, 585-615 (1939).

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method for reversing HIV latency in a cell, the method comprising:
   contacting a cell that is latently infected with HIV with a BAF complex modulating compound to induce HIV transcription in the cell, wherein the BAF complex modulating compound is of formula (IA):

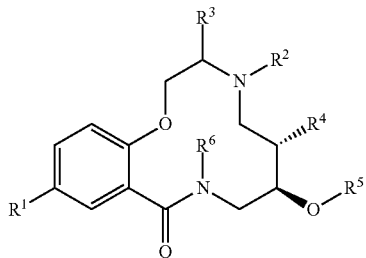

(IA)

wherein:
   $R^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;
   $R^2$ is heteroaryl-aryl-alkyl, substituted heteroaryl-aryl-alkyl, aryl-heteroaryl-alkyl, substituted aryl-heteroaryl alkyl, alkanoyl or substituted alkanoyl;
   $R^3$ to $R^6$ are each independently H, alkyl or substituted alkyl;
   or a pharmaceutically acceptable salt thereof.

2. The method of claim 1, wherein the BAF complex modulating compound specifically inhibits a BAF complex associated with HIV transcriptional repression in the cell.

3. The method of claim 1, further comprising determining the level of HIV latency and/or HIV activation in the cell.

4. The method of claim 3, wherein the determining comprises assessing a level of HIV transcription in the cell.

5. The method of claim 1, further comprising eliminating or killing the cell.

6. The method of claim 5, wherein eliminating the cell includes contacting the cell with an anti-HIV agent.

7. The method of claim 1, wherein the cell is in vitro.

8. The method of claim 1, wherein the cell is a resting CD4-positive T cell comprising replication-competent HIV.

9. The method of claim 1, wherein $R^1$ is selected from:

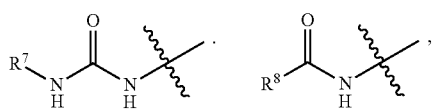

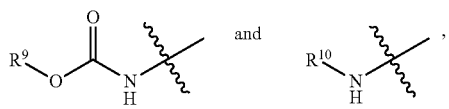

wherein:
   $R^7$, $R^8$ and $R^9$ are each independently selected from alkyl, substituted alkyl, aryl, substituted aryl, heteroaryl, and substituted heteroaryl, cycloalkyl, substituted cycloalkyl, heterocycle, substituted heterocycle; and
   $R^{10}$ is selected from H, alkyl, substituted alkyl, aryl, substituted aryl, heteroaryl, substituted heteroaryl, cycloalkyl, substituted cycloalkyl, heterocycle and substituted heterocycle.

10. The method of claim 9, wherein $R^1$ is selected from:

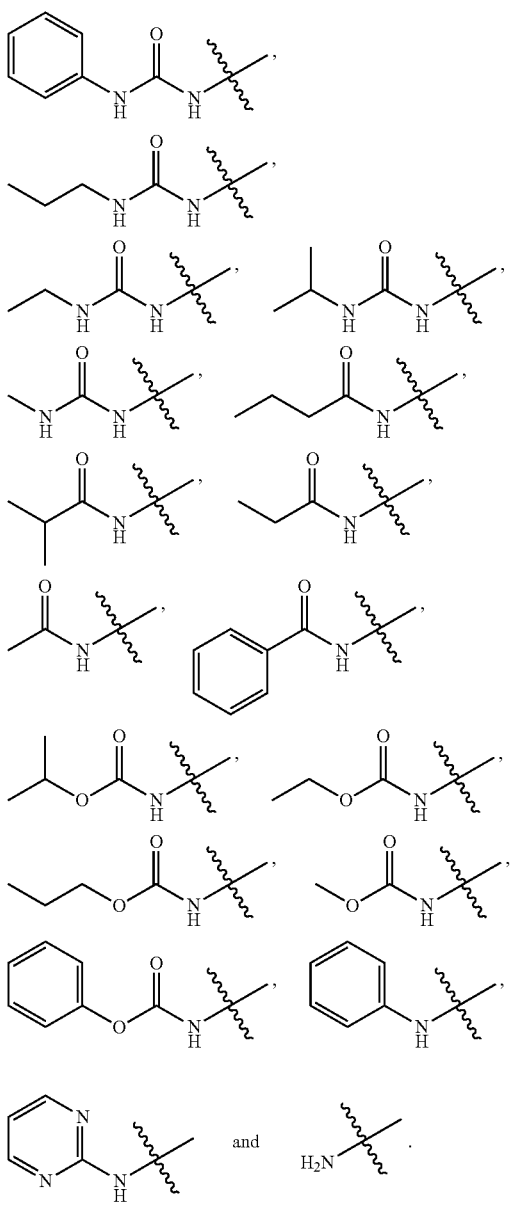

11. The method of claim 1, wherein $R^2$ is of the formula:

-L$^1$-Z(IC); or

-L$^2$-C(O)-L$^3$-R$^{11}$(ID)

wherein:

L$^1$ is an alkyl linker or a substituted alkyl linker;

L$^2$ and L$^3$ are each independently selected from a covalent bond, an alkyl linker and a substituted alkyl linker;

Z is heteroaryl-aryl, substituted heteroaryl-aryl, aryl-heteroaryl or substituted heteroaryl-aryl; and R$^{11}$ is alkyl, substituted alkyl, C$_{3-10}$ cycloalkyl, substituted C$_{3-10}$ cycloalkyl, C$_{3-10}$ heterocycle or substituted C$_{3-10}$ heterocycle.

12. The method of claim 1, wherein the BAF complex modulating compound is of formula (II):

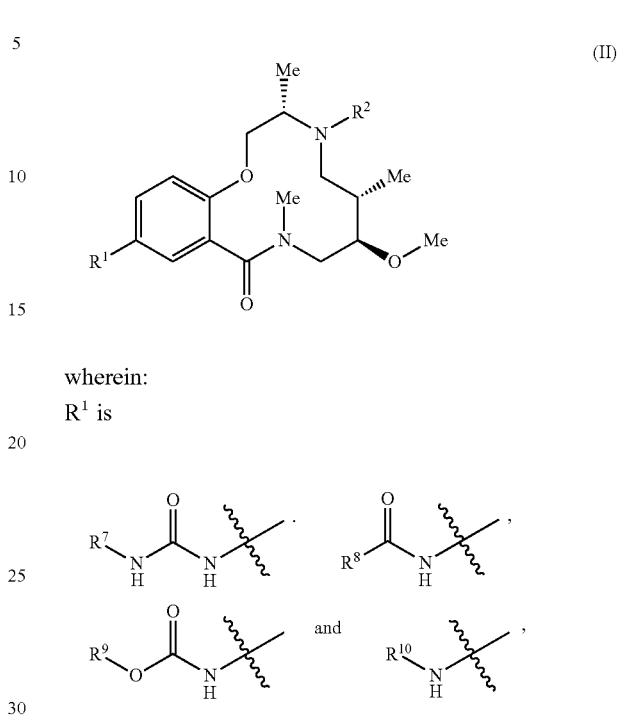

(II)

wherein:

R$^1$ is

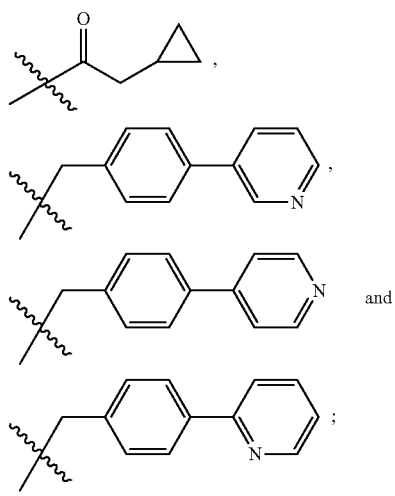

wherein:

R$^7$, R$^8$ and R$^9$ are each independently selected from, methyl, ethyl, propyl, isopropyl, butyl, sec-butyl, tert-butyl, pentyl, hexyl, aryl, substituted aryl, heteroaryl, substituted heteroaryl, cycloalkyl, substituted cycloalkyl heterocycle, and substituted heterocycle; and R$^{10}$ is selected from H, alkyl, substituted alkyl, aryl, substituted aryl, heteroaryl, substituted heteroaryl, cycloalkyl, substituted cycloalkyl, heterocycle and substituted heterocycle; and R$^2$ is selected from or a pharmaceutically acceptable salt thereof.

13. The method of claim 1, wherein the BAF complex modulating compound is of formula (III):

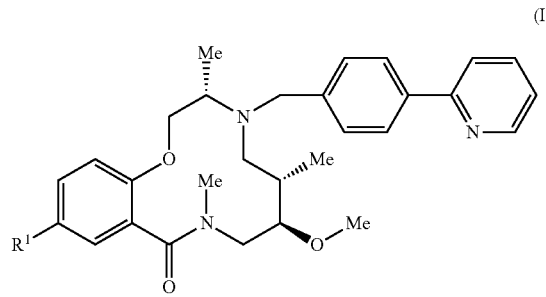
(III)

wherein:
R¹ is

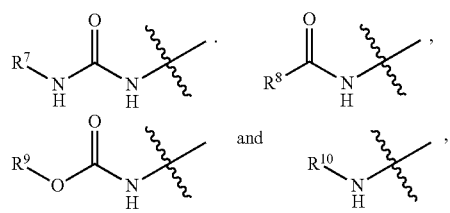

wherein:
R⁷, R⁸ and R⁹ are each independently selected from, methyl, ethyl, propyl, isopropyl, butyl, sec-butyl, tert-butyl, phenyl, hexyl, aryl, substituted aryl, heteroaryl, substituted heteroaryl, cycloalkyl substituted cycloalkyl, heterocycle, and substituted heterocycle;
R¹⁰ is selected from H, alkyl, substituted alkyl, aryl, substituted aryl, heteroaryl, substituted heteroaryl, cycloalkyl, substituted cycloalkyl, heterocycle and substituted heterocycle;
or a pharmaceutically acceptable salt thereof.

14. The method of claim 13, wherein R¹ is selected from:

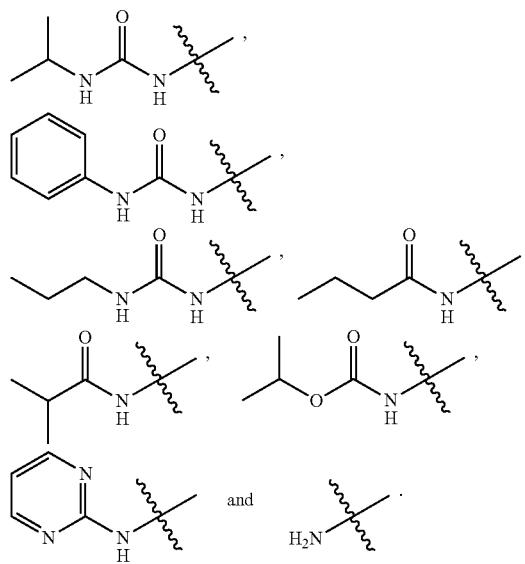

15. The method of claim 1, wherein the BAF complex modulating compound has a structure selected from:

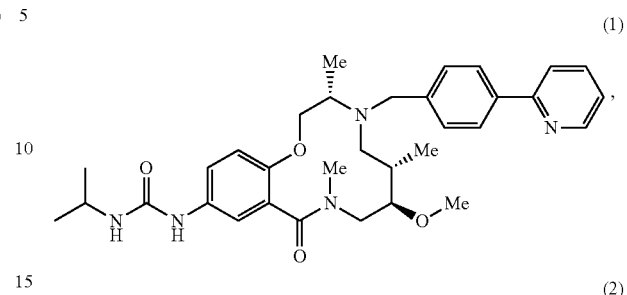
(1)

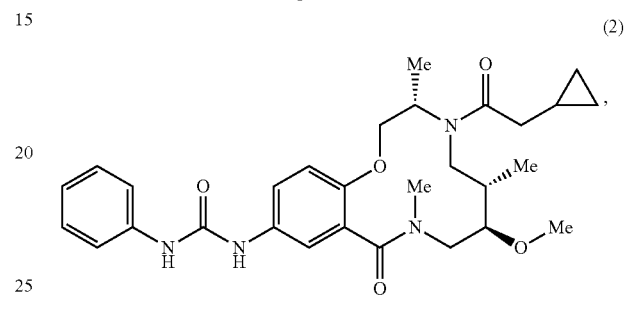
(2)

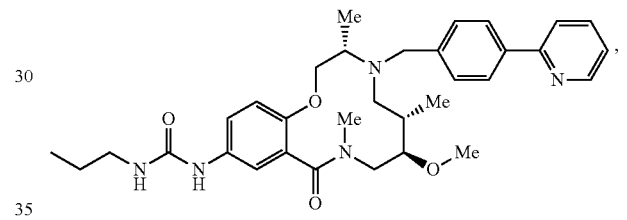
(3)

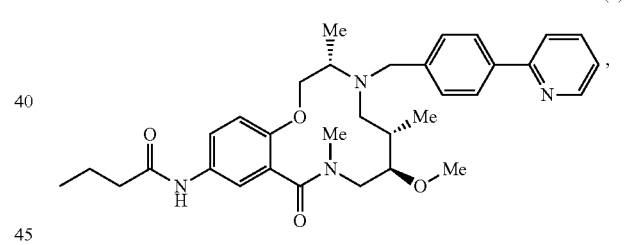
(4)

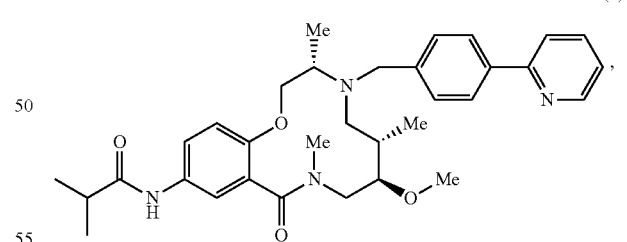
(5)

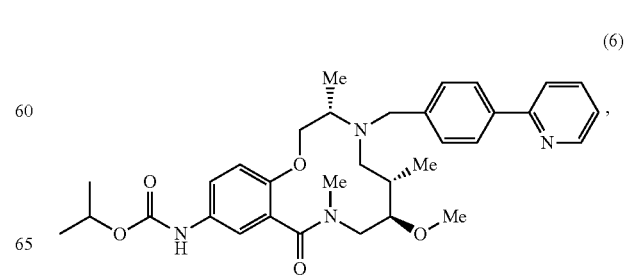
(6)

-continued (7)
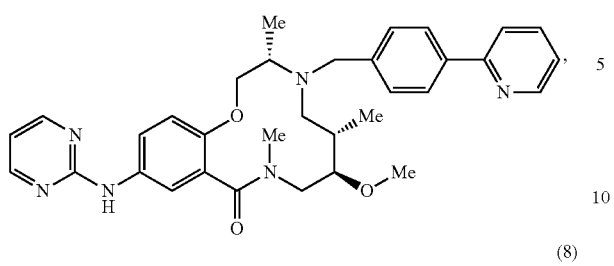

(8)
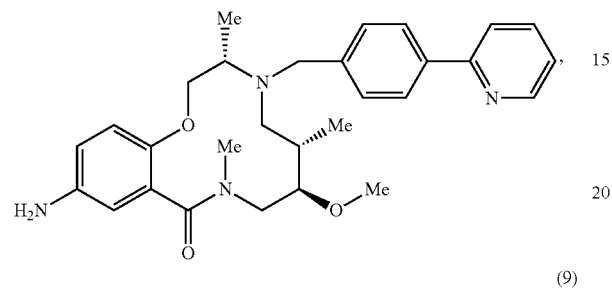

(9)
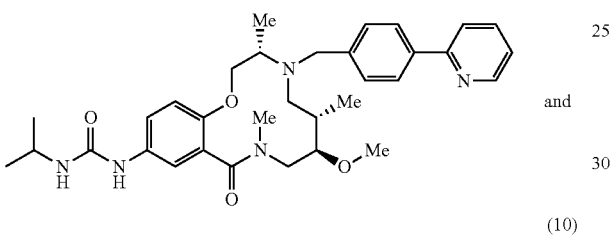

and

(10)
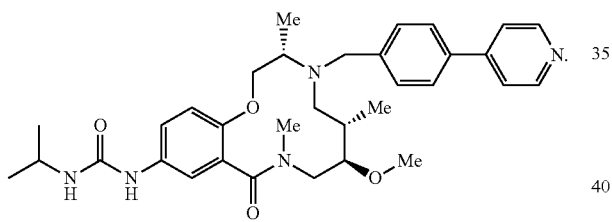

16. The method of any of claim 1, wherein the BAF complex modulating compound has the structure:

(1)
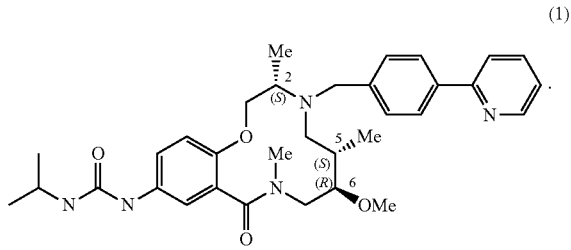

Baficillin1

17. A method of treating a subject for HIV-1 latency, the method comprising:

administering to a subject in need thereof a composition comprising a BAF complex modulating compound to induce HIV transcription in target cells in the subject, wherein the BAF complex modulating compound is of formula (IA):

(IA)
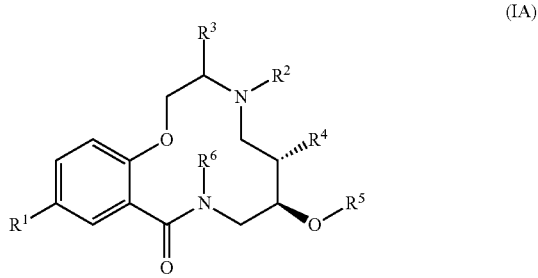

wherein:

$R^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;

$R^2$ is heteroaryl-aryl-alkyl, substituted heteroaryl-aryl-alkyl, aryl-heteroaryl-alkyl, substituted aryl-heteroaryl alkyl, alkanoyl or substituted alkanoyl;

$R^3$ to $R^6$ are each independently H, alkyl or substituted alkyl;

or a pharmaceutically acceptable salt thereof.

18. The method of claim 17, further comprising co-administering a second agent that is a HIV latency reversing agent.

19. The method of claim 17, further comprising administering an anti-HIV agent or antiretroviral therapy to the subject.

20. The method of claim 17, wherein the subject is human.

* * * * *

SEQUENCE LISTING

```
<160> NUMBER OF SEQ ID NOS: 29

<210> SEQ ID NO 1
<211> LENGTH: 20
<212> TYPE: DNA
<213> ORGANISM: Mus musculus

<400> SEQUENCE: 1
taccatgaat ggaaccagca                                          20

<210> SEQ ID NO 2
<211> LENGTH: 20
<212> TYPE: DNA
<213> ORGANISM: Mus musculus

<400> SEQUENCE: 2
aaaggaagca aactggacga                                          20

<210> SEQ ID NO 3
<211> LENGTH: 20
<212> TYPE: DNA
<213> ORGANISM: Mus musculus

<400> SEQUENCE: 3
cctggacatg ctgaagaaca                                          20

<210> SEQ ID NO 4
<211> LENGTH: 20
<212> TYPE: DNA
```

```
<213> ORGANISM: Mus musculus

<400> SEQUENCE: 4
tcccggctag ggtagatttt                                              20

<210> SEQ ID NO 5
<211> LENGTH: 22
<212> TYPE: DNA
<213> ORGANISM: Mus musculus

<400> SEQUENCE: 5
gggtgtggtg agcatcttcg ga                                           22

<210> SEQ ID NO 6
<211> LENGTH: 23
<212> TYPE: DNA
<213> ORGANISM: Mus musculus

<400> SEQUENCE: 6
ggtatgcgta ggactcgtag ggc                                          23

<210> SEQ ID NO 7
<211> LENGTH: 19
<212> TYPE: DNA
<213> ORGANISM: Mus musculus

<400> SEQUENCE: 7
tgcaccacca actgcttag                                               19

<210> SEQ ID NO 8
<211> LENGTH: 19
<212> TYPE: DNA
<213> ORGANISM: Mus musculus

<400> SEQUENCE: 8
ggatgcaggg atgatgttt                                               19

<210> SEQ ID NO 9
<211> LENGTH: 22
<212> TYPE: DNA
<213> ORGANISM: Homo sapiens

<400> SEQUENCE: 9
agcagaggaa gaccatgtgg ac                                           22

<210> SEQ ID NO 10
<211> LENGTH: 22
<212> TYPE: DNA
<213> ORGANISM: Homo sapiens

<400> SEQUENCE: 10
tttcgaccct gagagtctcc ag                                           22

<210> SEQ ID NO 11
<211> LENGTH: 18
<212> TYPE: DNA
<213> ORGANISM: Homo sapiens

<400> SEQUENCE: 11
aagccacagc atacatcc                                                18

<210> SEQ ID NO 12
<211> LENGTH: 18
```

```
<212> TYPE: DNA
<213> ORGANISM: Homo sapiens

<400> SEQUENCE: 12
gcacaagagt tccgtagc                                                   18

<210> SEQ ID NO 13
<211> LENGTH: 23
<212> TYPE: DNA
<213> ORGANISM: Homo sapiens

<400> SEQUENCE: 13
agcgtactcc aaagattcag gtt                                             23

<210> SEQ ID NO 14
<211> LENGTH: 24
<212> TYPE: DNA
<213> ORGANISM: Homo sapiens

<400> SEQUENCE: 14
atgatgctgc ttacatgtct cgat                                            24

<210> SEQ ID NO 15
<211> LENGTH: 24
<212> TYPE: DNA
<213> ORGANISM: Homo sapiens

<400> SEQUENCE: 15
ggtttattac agggacagca gaga                                            24

<210> SEQ ID NO 16
<211> LENGTH: 21
<212> TYPE: DNA
<213> ORGANISM: Homo sapiens

<400> SEQUENCE: 16
acctgccatc tgttttccat a                                               21

<210> SEQ ID NO 17
<211> LENGTH: 22
<212> TYPE: DNA
<213> ORGANISM: Homo sapiens

<400> SEQUENCE: 17
agcagaggaa gaccatgtgg ac                                              22

<210> SEQ ID NO 18
<211> LENGTH: 22
<212> TYPE: DNA
<213> ORGANISM: Homo sapiens

<400> SEQUENCE: 18
tttcgaccct gagagtctcc ag                                              22

<210> SEQ ID NO 19
<211> LENGTH: 18
<212> TYPE: DNA
<213> ORGANISM: Homo sapiens

<400> SEQUENCE: 19
aagccacagc atacatcc                                                   18

<210> SEQ ID NO 20
```

```
<211> LENGTH: 18
<212> TYPE: DNA
<213> ORGANISM: Homo sapiens

<400> SEQUENCE: 20
gcacaagagt tccgtagc                                                   18

<210> SEQ ID NO 21
<211> LENGTH: 23
<212> TYPE: DNA
<213> ORGANISM: Homo sapiens

<400> SEQUENCE: 21
agcgtactcc aaagattcag gtt                                             23

<210> SEQ ID NO 22
<211> LENGTH: 24
<212> TYPE: DNA
<213> ORGANISM: Homo sapiens

<400> SEQUENCE: 22
atgatgctgc ttacatgtct cgat                                            24

<210> SEQ ID NO 23
<211> LENGTH: 21
<212> TYPE: DNA
<213> ORGANISM: Homo sapiens

<400> SEQUENCE: 23
atctaccaca cacaaggcta c                                               21

<210> SEQ ID NO 24
<211> LENGTH: 22
<212> TYPE: DNA
<213> ORGANISM: Homo sapiens

<400> SEQUENCE: 24
gtactaactt gaagcaccat cc                                              22

<210> SEQ ID NO 25
<211> LENGTH: 20
<212> TYPE: DNA
<213> ORGANISM: Homo sapiens

<400> SEQUENCE: 25
aagtttgaca gcctcctagc                                                 20

<210> SEQ ID NO 26
<211> LENGTH: 19
<212> TYPE: DNA
<213> ORGANISM: Homo sapiens

<400> SEQUENCE: 26
cacacctccc tggaaagtc                                                  19

<210> SEQ ID NO 27
<211> LENGTH: 24
<212> TYPE: DNA
<213> ORGANISM: Homo sapiens

<400> SEQUENCE: 27
tttgcctgta ctgggtctct ctgg                                            24
```

```
<210> SEQ ID NO 28
<211> LENGTH: 21
<212> TYPE: DNA
<213> ORGANISM: Homo sapiens

<400> SEQUENCE: 28
cacaacagac gggcacacac t                                          21

<210> SEQ ID NO 29
<211> LENGTH: 36
<212> TYPE: PRT
<213> ORGANISM: Homo sapiens
<220> FEATURE:
<221> NAME/KEY: acetyl
<222> LOCATION: (1)..(1)
<220> FEATURE:
<221> NAME/KEY: amide
<222> LOCATION: (36)..(36)

<400> SEQUENCE: 29

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35
```